(12) United States Patent
Sheppard et al.

(10) Patent No.: US 8,231,866 B2
(45) Date of Patent: Jul. 31, 2012

(54) CYTOKINE PROTEIN FAMILY

(75) Inventors: Paul O. Sheppard, Granite Falls, WA (US); Brian A. Fox, Seattle, WA (US); Kevin M. Klucher, Bellevue, WA (US); David W. Taft, Kirkland, WA (US); Wayne Kindsvogel, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/353,524

(22) Filed: Jan. 19, 2012

(65) Prior Publication Data
US 2012/0142612 A1    Jun. 7, 2012

Related U.S. Application Data

(62) Division of application No. 13/028,101, filed on Feb. 15, 2011, now Pat. No. 8,124,065, which is a division of application No. 12/890,408, filed on Sep. 24, 2010, now Pat. No. 7,910,313, which is a division of application No. 12/630,571, filed on Dec. 3, 2009, now Pat. No. 7,829,076, which is a division of application No. 11/868,170, filed on Oct. 5, 2007, now Pat. No. 7,655,222, which is a division of application No. 11/539,093, filed on Oct. 5, 2006, now abandoned, which is a division of application No. 11/266,626, filed on Nov. 3, 2005, now abandoned, which is a division of application No. 10/127,816, filed on Apr. 19, 2002, now Pat. No. 7,038,032.

(60) Provisional application No. 60/285,424, filed on Apr. 20, 2001, provisional application No. 60/285,408, filed on Apr. 20, 2001, provisional application No. 60/286,482, filed on Apr. 25, 2001, provisional application No. 60/341,050, filed on Oct. 22, 2001, provisional application No. 60/341,105, filed on Oct. 22, 2001.

(51) Int. Cl.
*A61K 38/00* (2006.01)
*A61K 45/00* (2006.01)
*C07K 14/00* (2006.01)

(52) U.S. Cl. ........ 424/85.1; 424/85.2; 530/351; 514/1.1
(58) Field of Classification Search .................. None
See application file for complete search history.

(56) References Cited

U.S. PATENT DOCUMENTS

| | | | |
|---|---|---|---|
| 6,927,040 B2 | 8/2005 | Sheppard et al. |
| 7,038,032 B2 | 5/2006 | Sheppard et al. |
| 7,135,170 B2 | 11/2006 | Klucher et al. |
| 7,157,559 B2 | 1/2007 | Brady et al. |
| 7,241,870 B2 | 7/2007 | Sheppard et al. |
| 7,252,969 B2 | 8/2007 | Sheppard et al. |
| 7,253,261 B2 | 8/2007 | Sheppard et al. |
| 7,351,689 B2 | 4/2008 | Doyle et al. |
| 7,445,773 B2 | 11/2008 | Sheppard et al. |
| 7,445,913 B2 | 11/2008 | Sheppard et al. |
| 7,446,172 B2 | 11/2008 | Sheppard et al. |
| 7,455,993 B2 | 11/2008 | Sheppard et al. |
| 7,462,467 B2 | 12/2008 | Sheppard et al. |
| 7,468,423 B2 | 12/2008 | Brady et al. |
| 7,479,542 B2 | 1/2009 | Brady et al. |
| 7,485,699 B2 | 2/2009 | Sheppard et al. |
| 7,485,700 B2 | 2/2009 | Sheppard et al. |
| 7,485,701 B2 | 2/2009 | Brady et al. |
| 7,485,702 B2 | 2/2009 | Brady et al. |
| 7,495,077 B2 | 2/2009 | Brady et al. |
| 7,495,078 B2 | 2/2009 | Brady et al. |
| 7,495,079 B2 | 2/2009 | Brady et al. |
| 7,498,154 B2 | 3/2009 | Sheppard et al. |
| 7,514,536 B2 | 4/2009 | Brady et al. |
| 7,517,961 B2 | 4/2009 | Brady et al. |
| 7,544,779 B2 | 6/2009 | Brady et al. |
| 7,582,450 B2 | 9/2009 | Brady et al. |
| 7,588,918 B2 | 9/2009 | Brady et al. |
| 7,588,919 B2 | 9/2009 | Brady et al. |
| 7,595,174 B2 | 9/2009 | Brady et al. |
| 7,608,427 B2 | 10/2009 | Brady et al. |
| 7,608,428 B2 | 10/2009 | Brady et al. |
| 7,629,148 B2 | 12/2009 | Brady et al. |
| 7,629,149 B2 | 12/2009 | Brady et al. |
| 7,638,305 B2 | 12/2009 | Brady et al. |
| 7,655,222 B2 | 2/2010 | Sheppard et al. |
| 7,655,223 B2 | 2/2010 | Sheppard et al. |
| 7,662,589 B2 | 2/2010 | Brady et al. |
| 7,662,590 B2 | 2/2010 | Brady et al. |
| 7,662,927 B2 | 2/2010 | Sheppard et al. |
| 7,727,518 B2 | 6/2010 | Brady et al. |
| 7,829,076 B2 | 11/2010 | Sheppard et al. |
| 7,833,520 B2 | 11/2010 | Sheppard et al. |
| 2008/0279816 A1 | 11/2008 | Brady et al. |
| 2010/0104531 A1 | 4/2010 | Brady et al. |
| 2011/0165121 A1 | 7/2011 | Hausman et al. |
| 2011/0300101 A1 | 12/2011 | Klucher et al. |

FOREIGN PATENT DOCUMENTS

| | | |
|---|---|---|
| EP | 0 032 134 | 7/1981 |
| WO | 00/37110 | 6/2000 |
| WO | 00/55324 | 9/2000 |
| WO | 02/20569 | 3/2002 |
| WO | 02/092762 | 11/2002 |
| WO | 03/066002 | 8/2003 |

OTHER PUBLICATIONS

Kotenko et al., "IFN-Is mediate antiviral protection through a distinct class II cytokine receptor complex," Nature Immunology 4(1):69-77, 2003.
Sheppard et al., "IL-28, Il-29 and their class II cytokine receptor IL-28R," Nature Immunology 4(1):63-68, 2003.
University Calif. Santa Cruz Genome Browser—Chromosome 19, Apr. 20, 2001.

(Continued)

*Primary Examiner* — Christine J Saoud
*Assistant Examiner* — Jegatheesan Seharaseyon
(74) *Attorney, Agent, or Firm* — Bing Hai

(57) ABSTRACT

The present invention relates to polynucleotide and polypeptide molecules for zcyto20, zcyto21, zcyto22, zycto24, and zcyto25 proteins which are most closely related to interferon-α at the amino acid sequence level. The receptor for this protein family is a class II cytokine receptor. The present invention includes methods of reducing viral infections and increasing monocyte counts. The present invention also includes antibodies to the zcyto20 polypeptides, and methods of producing the polynucleotides and polypeptides.

4 Claims, No Drawings

OTHER PUBLICATIONS

University Calif Santa Cruz Genome Browser Database—Aug. 6, 2001, Accession No. C19001210.
University Calif. Santa Cruz Genome Browser Database—Aug. 6, 2001, Accession No. C19001212.
University Calif. Santa Cruz Genome Browser Database—Aug. 6, 2001, Accession No. C19001213.
University Calif. Santa Cruz Genome Browser Database—Dec. 22, 2001, Accession No. C19001260.
University Calif. Santa Cruz Genome Browser Database—Dec. 22, 2001, Accession No. C19001256.
University Calif. Santa Cruz Genome Browser Database—Dec. 22, 2001, Accession No. C19001257.
Ensembl Contig. View Sanger Institute—Apr. 19, 2001, Accession No. AC011445.
Ensembl Contig. View Sanger Institute—Apr. 18, 2001, Accession No. AC018477.
Adams et al., "3,400 expressed sequence tags identify diversity of transcripts from human brain," Nat. Genet. 4:256-267, 1993.
GenBank Submission XP-002202436, Oct. 12, 2000.
GenBank Submission XP-002202437, Dec. 12, 1999.
Kindsvogel et al., "Novel Interferon-Like Cytokines not Recognized by the Type I Interferon Receptor," J. Interferon Cytokine Res. 22(1):S-48, 2002.
Database EMBL Sequence Library EBI-Hinxton, Oct. 8, 1999, Acc. No. AC011445. (XP-002328024).
Brack et al., "Molecular analysis of the human interferon-a gene family," Gene 15:379-394, 1981.
Burge et al., "Prediction of Complete Gene Structures in Human Genomic DNA," J. Mol. Biol. 268:78-94, 1997.
Vilcek, "Novel interferons," Nature Immunology 4(1):8-9, 2003.
Xie et al., Journal of Biological Chemistry, 275(40): 31335-31339, 2000.
Sheppard, U.S. Appl. No. 12/352,454, filed Jan. 12, 2009.
Sheppard et al., U.S. Appl. No. 12/890,408, filed Sep. 24, 2010.
Emison, E.S., U.S. Appl. No. 61/449,418 (Mar. 4, 2011).

CYTOKINE PROTEIN FAMILY

REFERENCE TO RELATED APPLICATIONS

The present application is divisional of U.S. patent application Ser. No. 13/028,101, filed Feb. 15, 2011, which is a divisional of U.S. patent application Ser. No. 12/890,408, filed Sep. 24, 2010, now U.S. Pat. No. 7,910,313, which is a divisional of U.S. patent application Ser. No. 12/630,571, now U.S. Pat. No. 7,829,076, filed Dec. 3, 2009, which is a divisional of U.S. patent application Ser. No. 11/868,170, now U.S. Pat. No. 7,655,222, filed Oct. 5, 2007, which is a divisional of U.S. patent application Ser. No. 11/539,093, filed Oct. 5, 2006, abandoned, which is a divisional of U.S. patent application Ser. No. 11/266,626, filed Nov. 3, 2005, abandoned, which is a divisional of U.S. patent application Ser. No. 10/127,816, now U.S. Pat. No. 7,038,032, filed Apr. 19, 2002, which claims the benefit of U.S. Patent Application Ser. No. 60/285,424, filed Apr. 20, 2001, U.S. Patent Application Ser. No. 60/285,408, filed Apr. 20, 2001, U.S. Patent Application Ser. No. 60/286,482, filed Apr. 25, 2001, U.S. Patent Application Ser. No. 60/341,050, filed Oct. 22, 2001, U.S. Patent Application Ser. No. 60/341,105, filed Oct. 22, 2001, and U.S. patent application Ser. No. 09/895,834, filed Jun. 29, 2001, now U.S. Pat. No. 6,927,040, all of which are herein incorporated by reference.

BACKGROUND OF THE INVENTION

Cellular differentiation of multicellular organisms is controlled by hormones and polypeptide growth factors. These diffusable molecules allow cells to communicate with each other and act in concert to form tissues and organs, and to repair and regenerate damaged tissue. Examples of hormones and growth factors include the steroid hormones, parathyroid hormone, follicle stimulating hormone, the interferons, the interleukins, platelet derived growth factor, epidermal growth factor, and granulocyte-macrophage colony stimulating factor, among others.

Hormones and growth factors influence cellular metabolism by binding to receptor proteins. Certain receptors are integral membrane proteins that bind with the hormone or growth factor outside the cell, and that are linked to signaling pathways within the cell, such as second messenger systems. Other classes of receptors are soluble intracellular molecules.

Cytokines generally stimulate proliferation or differentiation of cells of the hematopoietic lineage or participate in the immune and inflammatory response mechanisms of the body. Examples of cytokines which affect hematopoiesis are erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

Cytokines play important roles in the regulation of hematopoiesis and immune responses, and can influence lymphocyte development. The human class II cytokine family includes interferon-α (IFN-α) subtypes, interferon-β (IFN-β), interferon-γ (IFN-γ), IL-10, IL-19 (U.S. Pat. No. 5,985,614), MDA-7 (Jiang et al., *Oncogene* 11, 2477-2486, (1995)), IL-20 (Jiang et al., *Oncogene* 11, 2477-2486, (1995)), IL-22 (Xie et al., *J. Biol. Chem.* 275, 31335-31339, (2000)), and AK-155 (Knappe et al., *J. Virol.* 74, 3881-3887, (2000)). Most cytokines bind and transduce signals through either Class I or Class II cytokine receptors. Members of human class II cytokine receptor family include interferon-αR1 (IFN-αR1), interferon-γ-R2 (IFN-γ-R2), interferon-γ R1 (IFN-γ R1), interferon-γR2 (IFN-γR2), IL-10R (Liu et al., *J. Immunol.* 152, 1821-1829, (1994)), CRF2-4 (Lutfalla et al. *Genomics* 16, 366-373, (1993)), IL-20Rβ (Blumberg et al., *Cell* 104, 9-19, (2001)) (also known as zcytor7 (U.S. Pat. No. 5,945,511) and CRF2-8 (Kotenko et al., *Oncogene* 19, 2557-2565, (2000)), IL-20R13 (Blumberg et al., ibid, (2001)) (also known as DIRS1 (PCT WO 99/46379)), IL-22RA1 (IL-22 receptor-α1, submitted to HUGO for approval) (also known as IL-22R (Xie et al., *J. Biol. Chem.* 275, 31335-31339, (2000)), zcytor11 (U.S. Pat. No. 5,965,704) and CRF2-9 (Kotenko et al., *Oncogene* 19, 2557-2565, (2000)), and tissue factor.

Class II cytokine receptors are typically heterodimers composed of two distinct receptor chains, the α and β receptor subunits (Stahl et al., *Cell* 74, 587-590, (1993)). In general, the α subunits are the primary cytokine binding proteins, and the β subunits are required for formation of high affinity binding sites, as well as for signal transduction. An exception is the IL-20 receptor in which both subunits are required for IL-20 binding (Blumberg et al., ibid, (2001)).

The class II cytokine receptors are identified by a conserved cytokine-binding domain of about 200 amino acids (D200) in the extracellular portion of the receptor. This cytokine-binding domain is comprised of two fibronectin type III (FnIII) domains of approximately 100 amino acids each (Bazan J. F. *Proc. Natl. Acad. Sci. USA* 87, 6934-6938, (1990); Thoreau et al., *FEBS Lett.* 282, 16-31, (1991)). Each FnIII domain contains conserved Cys, Pro, and Trp residues that determine a characteristic folding pattern of seven β-strands similar to the constant domain of immunoglobulins (Uze et al., *J. Interferon Cytokine Res.* 15, 3-26, (1995)). The conserved structural elements of the class II cytokine receptor family make it possible to identify new members of this family on the basis of primary amino acid sequence homology. Previously we have successfully identified two new members of class II cytokine receptor family, zcytor7 (U.S. Pat. No. 5,945,511) (also known as IL-20R a (Blumberg et al., ibid, (2001)) and zcytor11 (U.S. Pat. No. 5,965,704) (also known as IL-22R (Blumberg et al., ibid, (2001)), using this approach. Identification of additional novel members of the class II cytokine receptor family is of interest because cytokines play a vital role in regulating biological responses.

IL-22, also known as IL-TIF (IL-10-related T cell-derived inducible factor) (Dumoutier et al., *J. Immunology* 164, 1814-1819, (2000)), is a recently described IL-10 homologue. Mouse IL-22 was originally identified as a gene induced by IL-9 in T cells and mast cells in vitro (Dumoutier et al., *J. Immunology* 164, 1814-1819, (2000)). Acute phase reactant induction activity was observed in mouse liver upon IL-22 injection, and IL-22 expression was rapidly induced after lipopolysaccharide (LPS) injection, suggesting that IL-22 contributes to the inflammatory response in vivo (Dumoutier et al., *Proc. Natl. Acad. Sci. U.S.A.* 97, 10144-10149, (2000)).

The interleukins are a family of cytokines that mediate immunological responses, including inflammation. The interleukins mediate a variety of inflammatory pathologies. Central to an immune response is the T cell, which produce many cytokines and adaptive immunity to antigens. Cytokines produced by the T cell have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Of particular interest, from a therapeutic standpoint, are the interferons (reviews on interferons are provided by De Maeyer and De Maeyer-Guignard, "Interferons," in *The Cytokine Handbook*, 3rd Edition, Thompson (ed.), pages 491-516 (Academic Press Ltd. 1998), and by Walsh, *Biopharmaceuticals: Biochemistry and Biotechnology*, pages 158-188 (John Wiley & Sons 1998)). Interferons exhibit a variety of biological activities, and are useful for the treatment of certain autoimmune diseases, particular cancers, and the enhancement of the immune response against infectious agents, including viruses, bacteria, fungi, and protozoa. To date, six forms of interferon have been identified, which have been classified into two major groups. The so-called "type I" interferons include interferon-α, interferon-β, interferon-ω, interferon-δ, and interferon-τ. Currently, interferon-γ and one subclass of interferon-α are the only type II interferons.

Type I interferons, which are thought to be derived from the same ancestral gene, have retained sufficient similar structure to act by the same cell surface receptor. The α-chain of the human interferon-α/β receptor comprises an extracellular N-terminal domain, which has the characteristics of a class II cytokine receptor. Interferon-γ does not share significant homology with the type I interferons or with the type II interferon-α subtype, but shares a number of biological activities with the type I interferons.

In humans, at least 16 non-allelic genes code for different subtypes of interferon-α, while interferons β and ω are encoded by single genes. Type I interferon genes are clustered in the short arm of chromosome 9. Unlike typical structural human genes, interferon-α, interferon-β, and interferon-ω lack introns. A single gene for human interferon-γ is localized on chromosome 12 and contains three introns. To date, interferon-τ has been described only in cattle and sheep, while interferon-6 has been described only in pigs.

Clinicians are taking advantage of the multiple activities of interferons by using the proteins to treat a wide range of conditions. For example, one form of interferon-α has been approved for use in more than 50 countries for the treatment of medical conditions such as hairy cell leukemia, renal cell carcinoma, basal cell carcinoma, malignant melanoma, AIDS-related Kaposi's sarcoma, multiple myeloma, chronic myelogenous leukemia, non-Hodgkin's lymphoma, laryngeal papillomatosis, mycosis fungoides, condyloma acuminate, chronic hepatitis B, hepatitis C, chronic hepatitis D, and chronic non-A, non-B/C hepatitis. The U.S. Food and Drug Administration has approved the use of interferon-β to treat multiple sclerosis, a chronic disease of the nervous system. Interferon-γ is used to treat chronic granulomatous diseases, in which the interferon enhances the patient's immune response to destroy infectious bacterial, fungal, and protozoal pathogens. Clinical studies also indicate that interferon-γ may be useful in the treatment of AIDS, leishmaniasis, and lepromatous leprosy.

The demonstrated in vivo activities of the cytokine family illustrate the enormous clinical potential of, and need for, other cytokines, cytokine agonists, and cytokine antagonists. The present invention addresses these needs by providing a new cytokine that stimulates cells of the hematopoietic cell lineage, as well as related compositions and methods.

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussemeyer et al., *Proc. Natl. Acad. Sci. USA* 82:7952-4, 1985), substance P, Flag™ peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of $<10^9$ $M^{-1}$.

The term "complements of a polynucleotide molecule" denotes a polynucleotide molecule having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e. invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention includes a genus of polynucleotide and polypeptide molecules that have functional and structural similarity to the interferons. In this new family, which includes molecules designated zcyto20 (SEQ ID NOS: 1 and 2), zcyto21 (SEQ ID NOS:4 and 5), zcyto22 (SEQ ID NOS:6 and 7), zcyto24 (SEQ ID NOS:8 and 9), zcyto25 (SEQ ID NOS: 10 and 11), zcyto20, 21, and 22 are human sequences and zcyto24 and 25 are mouse sequences. Homology within the family at the nucleotide and amino acid levels is shown in Table 1, ranging from approximately 72% to 98% at the nucleotide level, and 51% to 97% at the amino acid level.

TABLE 1

| | | \multicolumn{6}{c}{nucleotide sequence identity} | | | | | |
|---|---|---|---|---|---|---|---|
| | | zcyto20 | zcyto22 | zcyto21 | zcyto24 | zcyto25 | rat |
| protein | zcyto20 | 100 | 98.2 | 72.9 | 74.0 | 72.1 | 73.4 |
| sequence | zcyto22 | 96.0 | 100 | 73.0 | 73.9 | 71.9 | 72.9 |
| identity | zcyto21 | 66.5 | 67.5 | 100 | 64.9 | 62.9 | 64.6 |
| | zcyto24 | 62.7 | 63.7 | 51.7 | 100 | 97.2 | 90.3 |
| | zcyto25 | 59.8 | 60.8 | 48.8 | 93.6 | 100 | 88.4 |

Table 2 is an illustration of the sequence identity between zcyto20, zcyto21, zcyto22, IFNα, IFNβ, IFNγ, and IL10 at the amino acid level.

TABLE 2 amino acid sequence identity

| | Zcyto20 | Zcyto22 | Zcyto21 | IFNα | IFNβ | IFNγ | IL10 |
|---|---|---|---|---|---|---|---|
| Zcyto20 | 100 | | | | | | |
| Zcyto21 | 81 | 100 | | | | | |
| Zcyto22 | 96 | 74 | 100 | | | | |
| IFNα | 17 | 16 | 17 | 100 | | | |
| IFNβ | 14 | 13 | 14 | 31 | 100 | | |
| IFNγ | 4 | 4 | 4 | 7 | 5 | 100 | |
| IL10 | 13 | 12 | 14 | 7 | 5 | 8 | 100 |

All the members of the family have been shown to bind to the same class II cytokine receptor, designated zcytor19 receptor. Furthermore, certain biological activities have been shown to be exhibited by each molecule in the family. These activities include, for example, antiviral activities and increasing circulating myeloid cell levels. While not wanting to be bound by theory, these molecules appear to all signal through zcytor19 receptor via the same pathway.

Zcyto20 gene encodes a polypeptide of 205 amino acids, as shown in SEQ ID NO:2. The signal sequence for Zcyto20 can be predicted as comprising amino acid residue 1 (Met) through amino acid residue 21 (Ala) of SEQ ID NO:2. The mature peptide for Zcyto20 begins at amino acid residue 22 (Val).

Zcyto21 gene encodes a polypeptide of 200 amino acids, as shown in SEQ ID NO:5. The signal sequence for Zcyto21 can be predicted as comprising amino acid residue 1 (Met) through amino acid residue 19 (Ala) of SEQ ID NO:5. The mature peptide for Zcyto21 begins at amino acid residue 20 (Gly). Zcyto21 has been described in PCT application WO 02/02627.

Zcyto22 gene encodes a polypeptide of 205 amino acids, as shown in SEQ ID NO:7. The signal sequence for Zcyto22 can be predicted as comprising amino acid residue 1 (Met) through amino acid residue 21 (Ala) of SEQ ID NO:7. The mature peptide for Zcyto22 begins at amino acid residue 22 (Val).

Zcyto24 gene encodes a polypeptide of 202 amino acids, as shown in SEQ ID NO:9. Zcyto24 secretory signal sequence comprises amino acid residue 1 (Met) through amino acid residue 28 (Ala) of SEQ ID NO:9. An alternative site for cleavage of the secretory signal sequence can be found at amino acid residue 24 (Thr). The mature polypeptide comprises amino acid residue 29 (Asp) to amino acid residue 202 (Val).

Zcyto25 gene encodes a polypeptide of 202 amino acids, as shown in SEQ ID NO:11. Zcyto25 secretory signal sequence comprises amino acid residue 1 (Met) through amino acid residue 28 (Ala) of SEQ ID NO:11. An alternative site for cleavage of the secretory signal sequence can be found at amino acid residue 24 (Thr). The mature polypeptide comprises amino acid residue 29 (Asp) to amino acid residue 202 (Val).

The Zcyto20, Zcyto21 and Zcyto22 genes have been mapped to human chromosome 19q13.13. Based on the discovery of these genes, this region of chromosome 19 has been identified as comprising a cluster of interferon-like genes. Further indication that this is new family of genes is identification of a syntenic cluster of genes on the mouse chromosome 7, zcyto24 (SEQ ID NO: 8) and zcyto25 (SEQ ID NO: 10).

As described below, the present invention provides isolated polypeptides having an amino acid sequence that is at least 70%, at least 80%, or at least 90%, 95%, 96%, 97%, 98% or 99% identical to either amino acid residues 22 to 205 of SEQ ID NO:2 or amino acid residues 1 to 205 of SEQ ID NO:2, or some fragment thereof. The present invention also includes a polypeptide that further comprises a signal secretory sequence that resides in an amino-terminal position relative to the first amino acid sequence, wherein the signal secretory sequence comprises amino acid residues 1 to 21 of the amino acid sequence of SEQ ID NO:2.

In another embodiment, the present invention provides isolated polypeptides having an amino acid sequence that is at least 70%, at least 80%, or at least 90%, 95%, 96%, 97%, 98% or 99% identical to either amino acid residues 22 to 205 of SEQ ID NO:7 or amino acid residues 1 to 205 of SEQ ID NO:7. The present invention also includes a polypeptide that further comprises a signal secretory sequence that resides in an amino-terminal position relative to the first amino acid sequence, wherein the signal secretory sequence comprises amino acid residues 1 to 21 of the amino acid sequence of SEQ ID NO:7.

In general, cytokines, like erythropoietin (EPO), are predicted to have a four-alpha helix structure, with helices A, C and D being most important in ligand-receptor interactions, and are more highly conserved among members of the family. However, the interferons (INF), and interferon-alpha and interferon-tau in particular, are characterized as six helix bundles. EPO helix A is equivalent to helix A of zcyto20; EPO helix B is equivalent to helix C of zcyto20; EPO helix C is equivalent to helix D of zcyto20, and EPO helix D is equivalent to helix F of zcyto20. Thus, the loop between the AB loop, and CD loop of EPO is expanded in zcyto20 to contain short helices B and E of zcyto20. The helical structures of zcyto20, zcyto21, zcyto22, zcyto24 and zcyto25 are similar to the six-helix structure found in the interferons. Boundaries of secondary structures in proteins are generally defined in accordance with a range of PHI and PSI angles of the protein chain backbone from a 3-dimensional model of the protein. Models may be constructed from, for example, x-ray crystallography or NMR data, or homology modeling based on a solved structure. Depending on techniques used, including conditions for crystal formation and flexible NMR solution structure determination, boundaries of these secondary structures may be slightly altered. Thus, those skilled in the art will recognize that the helical boundaries, and secondary structures in general, depending on the environment, may shift by as much as 2, 3, 4, or more residues, but helical regions are essentially as described below. (See, Brandon and Tooze, *Introduction to Protein Structure*, Garland Publishing Co, inc. New York, 1991; Anderson, et. al., *Structure*, 10(2):175-84. 2002.)

Zcyto20 helices are predicted as follow: helix A is defined by amino acid residues 52 (Ala) to 66 (Leu); helix B by amino acid residues 78 (Arg) to 87 (Val); helix C by amino acid residues 91 (Pro) to 108 (Thr); helix D by amino acid residues 116 (Val) to 138 (Ser); helix E by amino acid residues 151 (Thr) to 172 (Lys); and helix F by amino acid residues 177 (Gly) to 197 (Cys); as shown in SEQ ID NO: 2. Four cysteine residues are conserved between Zcyto20, Zcyto21, and INF-α. In addition, Zcyto20 has 3 additional cysteines. The cysteine at amino acid residue 204, may form an intermolecular disulfide bond, in particular to form homodimers with additional Zcyto20 molecules. Further analysis of Zcyto20 based on multiple alignments predicts that cysteines at amino acid residues 37 and 136; 69 and 197; and 71 and 178 (as shown in SEQ ID NO: 2) will form intramolecular disulfide bonds. The corresponding polynucleotides encoding the Zcyto20 polypeptide regions, domains, motifs, residues and sequences described herein are as shown in SEQ ID NO:1.

Zcyto21 helices are predicted as follows: helix A is defined by amino acid residues 49 (Ser) to 63 (Leu); helix B by amino acid residues 76 (Asn) to 84 (Val); helix C by amino acid residues 89 (Val) to 104 (Ala); helix D by amino acid residues 111 (Glu) to 133 (Gln); helix E by amino acid residues 137 (Thr) to 158 (Lys); and helix F by amino acid residues 163 (Gly) to 189 (Leu); as shown in SEQ ID NO: 5. The cysteine residues are conserved between Zcyto21, Zcyto21, and INF-α, and may form an intermolecular disulfide bond, in particular to form homodimers with additional Zcyto21 molecules. Further analysis of Zcyto21 based on multiple alignments predicts that cysteines at amino acid residues 34 and 131, and 68 and 164, will form intramolecular disulfide bonds. The cysteine at residue 190 is free, and may form an intermolecular disulfide association. The corresponding polynucleotides encoding the Zcyto21 polypeptide regions, domains, motifs, residues and sequences described herein are as shown in SEQ ID NO:4.

Zcyto22 helices are predicted as follow: helix A is defined by amino acid residues 52 (Ala) to 66 (Leu); helix B by amino acid residues 78 (Arg) to 87 (Val); helix C by amino acid residues 91 (Pro) to 108 (Thr); helix D by amino acid residues 116 (Val) to 138 (Ser); helix E by amino acid residues 151 (Thr) to 172 (Lys); and helix F by amino acid residues 177 (Gly) to 197 (Cys); as shown in SEQ ID NO: 7. Four cysteine residues are conserved between Zcyto22, Zcyto21, and INF-α. In addition, Zcyto22 has 3 additional cysteines. The cysteine at amino acid residue 204, may form an intermolecular disulfide bond, in particular to form homodimers with additional Zcyto22 molecules. Further analysis of Zcyto22 based on multiple alignments predicts that cysteines at amino acid residues 37 and 136; 69 and 197; and 71 and 178 (as shown in SEQ ID NO: 7) will form intramolecular disulfide bonds. The corresponding polynucleotides encoding the Zcyto22 polypeptide regions, domains, motifs, residues and sequences described herein are as shown in SEQ ID NO:6.

Conserved cysteines for zcyto24 are shown at residues 44, 78, 141, and 175 of SEQ ID NO: 9. Further analysis of zcyto24 based on multiple alignments predicts that disulfide bonds will be formed between cysteines at amino acid residues 44 and 141; 78 and 175; (as shown in SEQ ID NO: 9). The corresponding polynucleotides encoding the zcyto24 polypeptide regions, domains, motifs, residues and sequences described herein are as shown in SEQ ID NO:9. The predicted helices in zcyto24 (as shown in SEQ ID NO:9) are: residues 59-73 (helix A); residues 85-94 (helix 13); residues 98-115 (helix C); residues 121-143 (helix D); residues 147-169 (helix E); residues 174-194 (helix F).

Conserved cysteines for zcyto25 are shown at residues 44, 78, 141, and 175 of SEQ ID NO: 11. Further analysis of zcyto25 based on multiple alignments predicts that disulfide bonds will be formed between cysteines at amino acid residues 44 and 141; 78 and 175; (as shown in SEQ ID NO: 11). The corresponding polynucleotides encoding the zcyto25 polypeptide regions, domains, motifs, residues and sequences described herein are as shown in SEQ ID NO:11. The predicted helices in zcyto25 (as shown in SEQ ID NO:11) are: residues 59-73 (helix A); residues 85-94 (helix B); residues 98-115 (helix C); residues 121-143 (helix D); residues 147-169 (helix E); residues 174-194 (helix F).

Detailed mutational analysis of murine IL-2 (Zurawski et al., *EMBO J.* 12:5113-5119, 1993) shows residues in helices A and C are important for binding to IL-2Rβ; critical residues are $Asp_{34}$, $Asn_{99}$, and $Asn_{103}$. Multiple residues within murine IL-2 loop A/B and helix B are important for IL-2Rα binding, while only a single residue, $Gln_{141}$ in helix D, is vital for binding with IL-2Rα. Similarly, helices A and C are sites of interaction between IL-4 and IL-4Rα (the structurally similar to IL-2Rα), and residues within helix D are vital for IL-2Rα interaction (Wang et al., *Proc. Natl. Acad. Sci. USA* 94:1657-1662, 1997; Kruse et al., *EMBO J.* 11:3237-3244, 1992). In particular, the mutation $Tyr_{124}$ to Asp in human IL-4 creates an antagonist, which binds with IL-4Rα but not IL-2Rα and therefore cannot signal (Kruse et al. ibid. 1992).

Four-helical bundle cytokines are also grouped by the length of their component helices. "Long-helix" form cytokines generally consist of between 24-30 residue helices, and include IL-6, ciliary neutrotrophic factor (CNTF), leukemia inhibitory factor (LIF) and human growth hormone (hGH). "Short-helix" form cytokines generally consist of between 18-21 residue helices and include IL-2, IL-4 and GM-CSF. Studies using CNTF and IL-6 demonstrated that a CNTF helix can be exchanged for the equivalent helix in IL-6, conferring CTNF-binding properties to the chimera. Thus, it appears that functional domains of four-helical cytokines are determined on the basis of structural homology, irrespective of sequence identity, and can maintain functional integrity in a chimera (Kallen et al., *J. Biol. Chem.* 274:11859-11867, 1999). Therefore, the helical domains of zcyto20, zcyto21, zcyto22, zcyto24 and zcyto25 will be useful for preparing chimeric fusion molecules, particularly with other interferons to determine and modulate receptor binding specificity. Of particular interest are fusion proteins that combine helical and loop domains from interferons and cytokines such as INF-α, IL-10, human growth hormone.

Zcyto20, zcyto21, zcyto22, zcyto24 and zcyto25 have been shown to form a complex with the orphan receptor designated zcytor19. Zcytor19 is described in a commonly assigned patent application PCT/US01/44808. Zcyto22, zcyto21, and zcyto24 have been shown to bind or signal through zcytor19 as well, further supporting that zcyto20, zcyto21, zcyto22, zcyto24 and zcyto25 are members of the same family of cytokines. Zcytor19 receptor is a class II cytokine receptor. Class II cytokine receptors usually bind to four-helix-bundle cytokines. For example, interleukin-10 and the interferons bind receptors in this class (e.g., interferon-gamma receptor, alpha and beta chains and the interferon-alpha/beta receptor alpha and beta chains).

Class II cytokine receptors are characterized by the presence of one or more cytokine receptor modules (CRM) in their extracellular domains. Other class II cytokine receptors include zcytor11 (commonly owned U.S. Pat. No. 5,965,704), CRF2-4 (Genbank Accession No. Z17227), IL-10R (Genbank Accession No.s U00672 and NM_001558), DIRS1, zcytor7 (commonly owned U.S. Pat. No. 5,945,511), and tissue factor. Zcytor19, like all known class II receptors except interferon-alpha/beta receptor alpha chain, has only a single class II CRM in its extracellular domain Analysis of a human cDNA clone encoding Zcytor19 (SEQ ID NO:26) revealed an open reading frame encoding 520 amino acids (SEQ ID NO:27) comprising a secretory signal sequence (residues 1 (Met) to 20 (Gly) of SEQ ID NO:27) and a mature zcytor19 cytokine receptor polypeptide (residues 21 (Arg) to 520 (Arg) of SEQ ID NO:27) an extracellular ligand-binding domain of approximately 206 amino acid residues (residues 21 (Arg) to 226 (Asn) of SEQ ID NO:27), a transmembrane domain of approximately 23 amino acid residues (residues 227 (Trp) to 249 (Trp) of SEQ ID NO:27), and an intracellular domain of approximately 271 amino acid residues (residues 250 (Lys) to 520 (Arg) of SEQ ID NO:27). Within the extracellular ligand-binding domain, there are two fibronectin type III domains and a linker region. The first fibronectin type III domain comprises residues 21 (Arg) to 119 (Tyr) of SEQ ID NO:27, the linker comprises residues 120 (Leu) to 124 (Glu) of SEQ ID NO:27, and the second fibronectin type III domain comprises residues 125 (Pro) to 223 (Pro) of SEQ ID NO:27. Thus, a polypeptide comprising amino acids 21 (Arg) to 223 (Pro) of SEQ ID NO:27 is considered a ligand binding fragment. In addition as typically conserved in class II receptors, there are conserved Tryptophan residues comprising residues 43 (Trp) and 68 (Trp) as shown in SEQ ID NO:27, and conserved Cysteine residues at positions 74, 82, 195, 217 of SEQ ID NO:27.

In addition, a human cDNA clone encoding a Zcytor19 variant with a 30 amino acid deletion was identified. This zcytor19 variant (as shown in SEQ ID NO:23) comprises an open reading frame encoding 491 amino acids (SEQ ID NO:24) comprising a secretory signal sequence (residues 1 (Met) to 20 (Gly) of SEQ ID NO:24) and a mature zcytor19 cytokine receptor polypetide (residues 21 (Arg) to 491 (Arg) of SEQ ID NO:24) an extracellular ligand-binding domain of approximately 206 amino acid residues (residues 21 (Arg) to 226 (Asn) of SEQ ID NO:24, a transmembrane domain of approximately 23 amino acid residues (residues 227 (Trp) to 249 (Trp) of SEQ ID NO:24), and an intracellular domain of approximately 242 amino acid residues (residues 250 (Lys) to 491 (Arg) of SEQ ID NO:24). Within the extracellular ligand-binding domain, there are two fibronectin type III domains and a linker region. The first fibronectin type III domain comprises residues 21 (Arg) to 119 (Tyr) of SEQ ID NO:24, the linker comprises residues 120 (Leu) to 124 (Glu) of SEQ ID NO:24, and the second fibronectin type III domain is short, and comprises residues 125 (Pro) to 223 (Pro) of SEQ ID NO:24. Thus, a polypeptide comprising amino acids 21 (Arg) to 223 (Pro) of SEQ ID NO:24 is considered a ligand binding fragment. In addition as typically conserved in class II receptors, there are conserved Tryptophan residues comprising residues 43 (Trp) and 68 (Trp) as shown in SEQ ID NO:24, and conserved Cysteine residues at positions 74, 82, 195, 217 of SEQ ID NO:24.

A truncated soluble form of the zcytor19 receptor mRNA appears to be naturally expressed. Analysis of a human cDNA clone encoding the truncated soluble Zcytor19 (SEQ ID NO:28) revealed an open reading frame encoding 211 amino acids (SEQ ID NO:29) comprising a secretory signal sequence (residues 1 (Met) to 20 (Gly) of SEQ ID NO:29) and a mature truncated soluble zcytor19 receptor polypetide (residues 21 (Arg) to 211 (Ser) of SEQ ID NO:29) a truncated extracellular ligand-binding domain of approximately 143 amino acid residues (residues 21 (Arg) to 163 (Trp) of SEQ ID NO:29), no transmembrane domain, but an additional domain of approximately 48 amino acid residues (residues 164 (Lys) to 211 (Ser) of SEQ ID NO:29). Within the truncated extracellular ligand-binding domain, there are two fibronectin type III domains and a linker region. The first fibronectin type 111 domain comprises residues 21 (Arg) to 119 (Tyr) of SEQ ID NO:29, the linker comprises residues 120 (Leu) to 124 (Glu) of SEQ ID NO:29, and the second fibronectin type III domain comprises residues 125 (Pro) to 163 (Trp) of SEQ ID NO:29. Thus, a polypeptide comprising amino acids 21 (Arg) to 163 (Trp) of SEQ ID NO:29 is considered a ligand binding fragment. In addition as typically conserved in class II receptors, there are conserved Tryptophan residues comprising residues 43 (Trp) and 68 (Trp) as shown in SEQ ID NO:29, and conserved Cysteine residues in this truncated soluble form of the zcytor19 receptor are at positions 74, and 82 of SEQ ID NO:29.

Zcytor19 receptor is a member of the same receptor subfamily as the class II cytokine receptors, and receptors in this subfamily may associate to form homodimers that transduce a signal. Several members of the subfamily (e.g., receptors that bind interferon, IL-10, IL-19, and IL-TIF) combine with a second subunit (termed a β-subunit) to bind ligand and transduce a signal. However, in many cases, specific β-subunits associate with a plurality of specific cytokine receptor subunits. For example, class II cytokine receptors, such as, zcytor11 (U.S. Pat. No. 5,965,704) and CRF2-4 receptor heterodimerize to bind the cytokine IL-TIF (See, WIPO publication WO 00/24758; Dumontier et al., *J. Immunol.* 164: 1814-1819, 2000; Spencer, S D et al., *J. Exp. Med.* 187:571-578, 1998; Gibbs, V C and Pennica *Gene* 186:97-101, 1997 (CRF2-4 cDNA); Xie, M H et al., *J. Biol. Chem.* 275: 31335-31339, 2000). IL-10β receptor is believed to be synonymous with CRF2-4 (Dumoutier, L. et al., *Proc. Nat'l. Acad. Sci.* 97:10144-10149, 2000; Liu Y et al, *J. Immunol.* 152; 1821-1829, 1994 (IL-10R cDNA). Therefore, one could expect that zcyto20, zcyto21, zcyto22, zcyto24 and zcyto25 would bind either monomeric, homodimeric, heterodimeric and multimeric zcytor19 receptors. Experimental evidence has identified CRF2-4 (SEQ ID NOS: 40 and 41) as the putative binding partner for zcytor19 which provides further support that zcyto20, zcyto21, zcyto22, zcyto24 and zcyto25 play an important role in the immunomodulatory system, affecting physiologies such as the innate immune system and the inflammatory response system.

Localizing the expression of a receptor for a ligand/receptor pair may have significance for identifying the target cell or tissue at which the ligand acts. This is particularly useful when the receptor/ligand complex involves a heterodimeric receptor in which one of the subunits is expressed widely and another the of the subunits is expressed in a limited manner, either spatially or temporally restricted. Using in situ hybridization expression of zcytor19 has been identified in a skin carcinoma sample, where the cancerous granular epithelium was strongly positive, while no positive signal is observed in normal skin. Other tissues identified as expressing zcytor19 included fetal liver, where signal was observed in a mixed population of mononuclear cells in sinusoid spaces; in lung expression was observed in type II alveolar epithelium; and in macrophage-like mononuclear cells in the interstitial tissue. Northern analysis of zcytor19 identified expression of a ~4.5 kb transcript which was in greatest in heart, skeletal muscle, pancreas, and prostate tissue, in addition to in the Burkitt's lymphoma (RAJI) cell line and SW-480 colorectal carcinoma cell line.

The present invention provides polynucleotide molecules, including DNA and RNA molecules, that encode the zcyto20, zcyto21, zcyto22, zcyto24, and zcyto25 polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zcyto20 polypeptide of SEQ ID NO:2. Those skilled in the art will recognize that the degenerate sequence of SEQ ID NO:3 also provides all RNA sequences encoding SEQ ID NO:2 by substituting U for T. Thus, zcyto20 polypeptide-encoding polynucleotides comprising nucleotide 1 or 64 to nucleotide 615 of SEQ ID NO:3 and their RNA equivalents are contemplated by the present invention. Table 3 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

SEQ ID NO:46 is a degenerate DNA sequence that encompasses all DNAs that encode the zcyto22 polypeptide of SEQ ID NO:7. Those skilled in the art will recognize that the degenerate sequence of SEQ ID NO:46 also provides all RNA sequences encoding SEQ ID NO:7 by substituting U for T. Thus, zcyto22 polypeptide-encoding polynucleotides comprising nucleotide 1 or 64 to nucleotide 615 of SEQ ID NO:46 and their RNA equivalents are contemplated by the present invention. Table 3 sets forth the one-letter codes used within SEQ ID NO:46 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

TABLE 3

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 4.

TABLE 4

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |

TABLE 4-continued

| Amino Acid | One Letter Code | Codons | Degenerate Codon |
|---|---|---|---|
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B |  | RAY |
| Glu\|Gln | Z |  | SAR |
| Any | X |  | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2 and SEQ ID NO:7. Variant sequences can be readily tested for functionality as described herein.

One of ordinary skill in the art will also appreciate that different species can exhibit "preferential codon usage." In general, see, Grantham, et al., *Nuc. Acids Res.* 8:1893-912, 1980; Haas, et al. *Curr. Biol.* 6:315-24, 1996; Wain-Hobson, et al., *Gene* 13:355-64, 1981; Grosjean and Fiers, *Gene* 18:199-209, 1982; Holm, *Nuc. Acids Res.* 14:3075-87, 1986; Ikemura, *J. Mol. Biol.* 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 3). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NOS:3 and 46 serves as a template for optimizing expression of polynucleotides in various cell types and species commonly used in the art and disclosed herein. Sequences containing preferential codons can be tested and optimized for expression in various species, and tested for functionality as disclosed herein.

As previously noted, the isolated polynucleotides of the present invention include DNA and RNA. Methods for preparing DNA and RNA are well known in the art. In general, RNA is isolated from a tissue or cell that produces large amounts of zcyto20, zcyto21, zcyto22, zcyto24 and zcyto25 RNA. Such tissues and cells are identified by Northern blotting (Thomas, *Proc. Natl. Acad. Sci. USA* 77:5201, 1980), or by screening conditioned medium from various cell types for activity on target cells or tissue. Once the activity or RNA producing cell or tissue is identified, total RNA can be prepared using guanidinium isothiocyanate extraction followed by isolation by centrifugation in a CsCl gradient (Chirgwin et al., *Biochemistry* 18:52-94, 1979). Poly (A)$^+$ RNA is prepared from total RNA using the method of Aviv and Leder (*Proc. Natl. Acad. Sci. USA* 69:1408-12, 1972). Complementary DNA (cDNA) is prepared from poly(A)$^+$ RNA using known methods. In the alternative, genomic DNA can be isolated. Polynucleotides encoding zcyto20, zcyto21, zcyto22, zcyto24 and zcyto25 polypeptides are then identified and isolated by, for example, hybridization or PCR.

A full-length clones encoding zcyto20, zcyto21, zcyto22, zcyto24 and zcyto25 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to Zcytor19 receptor fragments, or other specific binding partners.

The present invention further provides counterpart polypeptides and polynucleotides from other species (orthologs). These species include, but are not limited to mammalian, avian, amphibian, reptile, fish, insect and other vertebrate and invertebrate species. Of particular interest are zcyto20, zcyto21, zcyto22, zcyto24 and zcyto25 polypeptides from other mammalian species, including murine, porcine, ovine, bovine, canine, feline, equine, and other primate polypeptides. Orthologs of human zcyto20, zcyto21, and zcyto22 can be cloned using information and compositions provided by the present invention in combination with conventional cloning techniques. For example, a cDNA can be cloned using mRNA obtained from a tissue or cell type that expresses zcyto20, zcyto21, and zcyto22 as disclosed herein. Suitable sources of mRNA can be identified by probing Northern blots with probes designed from the sequences disclosed herein. A library is then prepared from mRNA of a positive tissue or cell line. Zcyto20-, zcyto21-, and zcyto22- encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zcyto20sequence disclosed herein. Within an additional method, the cDNA library can be used to transform or transfect host cells, and expression of the cDNA of interest can be detected with an antibody to zcyto20 polypeptide, binding studies or activity assays. Similar techniques can also be applied to the isolation of genomic clones.

Those skilled in the art will recognize that the sequence disclosed in SEQ ID NOS:1, 4, and 6, respectively, represent single alleles of human zcyto20, zcyto21, and zcyto22 bands, and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, 4 and 6, including those containing silent mutations and those in which mutations result in amino acid sequence changes, are within the scope of the present invention, as are proteins which are allelic variants of SEQ ID NO:2, 5, and 7. cDNAs generated from alternatively spliced mRNAs, which retain the properties of the zcyto20, zcyto21, and zcyto22 polypeptides, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The present invention also provides reagents which will find use in diagnostic applications. For example, the zcyto20, zcyto21, and zcyto22 genes, probes comprising zcyto20, zcyto21, and zcyto22 DNA or RNA or a subsequence thereof can be used to determine if the zcyto20, zcyto21, and zcyto22 gene is present on a human chromosome, such as chromosome 19, or if a gene mutation has occurred. Zcyto20, zcyto21, and zcyto22 are located at the q13.13 region of chromosome 19. Detectable chromosomal aberrations at the zcyto20, zcyto21, and zcyto22 gene locus include, but are not limited to, aneuploidy, gene copy number changes, loss of heterogeneity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

For example, Delague et al., (Am. J. Hum. Genet. 67: 236-243, 2000) identified that Charcot-Marie-Tooth disease is localized to 19q13.1-13.3 (Delague et al., Am. J. Hum. Genet. 67: 236-243, 2000).

A diagnostic could assist physicians in determining the type of disease and appropriate associated therapy, or assistance in genetic counseling. As such, the inventive anti-zcyto20 antibodies, polynucleotides, and polypeptides can be used for the detection of zcyto20 polypeptide, mRNA or anti-zcyto20 antibodies, thus serving as markers and be directly used for detecting or genetic diseases or cancers, as described herein, using methods known in the art and described herein. Further, zcyto20, zcyto21, and zcyto22 polynucleotide probes can be used to detect abnormalities or genotypes associated with chromosome 19q13.13 deletions and translocations associated with human diseases or other translocations involved with malignant progression of tumors or other 19q13.13 mutations, which are expected to be involved in chromosome rearrangements in malignancy; or in other cancers. Similarly, zcyto20 polynucleotide probes can be used to detect abnormalities or genotypes associated with chromosome 19q13.13 trisomy and chromosome loss associated with human diseases or spontaneous abortion. Thus, zcyto20, zcyto21, and zcyto22 polynucleotide probes can be used to detect abnormalities or genotypes associated with these defects.

In general, the diagnostic methods used in genetic linkage analysis, to detect a genetic abnormality or aberration in a patient, are known in the art. Analytical probes will be generally at least 20 nt in length, although somewhat shorter probes can be used (e.g., 14-17 nt). PCR primers are at least 5 nt in length, preferably 15 or more, more preferably 20-30 nt. For gross analysis of genes, or chromosomal DNA, a zcyto20 polynucleotide probe may comprise an entire exon or more. Exons are readily determined by one of skill in the art by comparing zcyto20, zcyto21, and zcyto22 sequences (SEQ ID NOS:1, 4, and 6, respectively) with the genomic DNA for zcyto20, zcyto21, and zcyto22. In general, the diagnostic methods used in genetic linkage analysis, to detect a genetic abnormality or aberration in a patient, are known in the art. Most diagnostic methods comprise the steps of (a) obtaining a genetic sample from a potentially diseased patient, diseased patient or potential non-diseased carrier of a recessive disease allele; (b) producing a first reaction product by incubating the genetic sample with a zcyto20 polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zcyto20 polynucleotide probe wherein the polynucleotide will hybridize to the complementary polynucleotide sequence of the first reaction; and (iv) comparing the visualized first reaction product to a second control reaction product of a genetic sample from wild type patient. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zcyto20 genetic locus, and the like, are indicative of a genetic abnormality, genetic aberration, or allelic difference in comparison to the normal wild type control. Controls can be from unaffected family members, or unrelated individuals, depending on the test and availability of samples. Genetic samples for use within the present invention include genomic DNA, mRNA, and cDNA isolated form any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1, the complement of SEQ ID NO:1, or an RNA equivalent thereof. Such methods of showing genetic linkage analysis to human disease phenotypes are well known in the art. For reference to PCR based methods in diagnostics see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zcyto20, zcyto21, and zcyto22 locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998)). Direct analysis of an zcyto20 gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Within embodiments of the invention, isolated zcyto20-encoding nucleic acid molecules can hybridize under stringent conditions to nucleic acid molecules having the nucleotide sequence of SEQ ID NO:1, to nucleic acid molecules having the nucleotide sequence of nucleotides 64 to 618 of SEQ ID NO:1, or to nucleic acid molecules having a nucleotide sequence complementary to SEQ ID NO:1. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Within embodiments of the invention, isolated zcyto22-encoding nucleic acid molecules can hybridize under stringent conditions to nucleic acid molecules having the nucleotide sequence of SEQ ID NO:6, to nucleic acid molecules having the nucleotide sequence of nucleotides 64 to 618 of SEQ ID NO:6, or to nucleic acid molecules having a nucleotide sequence complementary to SEQ ID NO:6.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The $T_m$, of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases.

It is well within the abilities of one skilled in the art to adapt these conditions for use with a particular polynucleotide hybrid. The $T_m$, for a specific target sequence is the temperature (under defined conditions) at which 50% of the target sequence will hybridize to a perfectly matched probe sequence. Those conditions which influence the $T_m$ include, the size and base pair content of the polynucleotide probe, the ionic strength of the hybridization solution, and the presence of destabilizing agents in the hybridization solution. Numerous equations for calculating $T_m$ are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated $T_m$. For smaller probes, <50 base pairs, hybridization is typically carried out at the $T_m$ or 5-10° C. below the calculated $T_m$. This allows for the maximum rate of hybridization for DNA-DNA and DNA-RNA hybrids.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant zcyto20, zcyto21, and zcyto22 polypeptides hybridize with a nucleic acid molecule having the nucleotide sequence of SEQ ID NOS:1, 4, and 6, respectively (or its complement) under stringent washing conditions, in which the wash stringency is equivalent to 0.5×-2×SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. In other words, nucleic acid molecules encoding a variant zcyto20 polypeptide hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated zcyto20, zcyto21, zcyto22, zcyto24 and zcyto25 polypeptides that have a substantially similar sequence identity to the polypeptides of SEQ ID NOS:2, 5, 7, 9, 11, respectively, or their orthologs. The term "substantially similar sequence identity" is used herein to denote polypeptides comprising at least 70%, at least 80%, at least 90%, at least 95%, or greater than 95% sequence identity to the sequences shown in SEQ ID NOS:2, 5, 7, 9, 11, respectively, or their orthologs. The present invention also includes polypeptides that comprise an amino acid sequence having at least 70%, at least 80%, at least 90%, at least 95% or greater than 95%, 96%, 97%, 98%, 99% sequence identity to the sequence of amino acid residues 1 to 205 or 21 to 205 of SEQ ID NO:2 or SEQ ID NO:7. The present invention further includes nucleic acid molecules that encode such polypeptides. Methods for determining percent identity are described below.

The present invention also contemplates variant zcyto20, zcyto21, and zcyto22 nucleic acid molecules that can be identified using two criteria: a determination of the similarity between the encoded polypeptide with the amino acid sequence of SEQ ID NOS:2, 5, 7, 9, 11, respectively, and/or a hybridization assay, as described above. Such zcyto20 variants include nucleic acid molecules: (1) that hybridize with a nucleic acid molecule having the nucleotide sequence of SEQ ID NOS:1, 4, 6, 8, 10, respectively (or its complement) under stringent washing conditions, in which the wash stringency is equivalent to 0.5×-2×SSC with 0.1% SDS at 55-65° C.; or (2) that encode a polypeptide having at least 70%, at least 80%, at least 90%, at least 95% or greater than 95% sequence identity to the amino acid sequence of SEQ ID NO:2. Alternatively, zcyto20, zcyto21, zcyto22, zcyto24 and zcyto25 variants can be characterized as nucleic acid molecules: (1) that hybridize with a nucleic acid molecule having the nucleotide sequence of SEQ ID NOS:1, 4, 6, 8, 10, respectively (or its complement) under highly stringent washing conditions, in which the wash stringency is equivalent to 0.1×-0.2×SSC with 0.1% SDS at 50-65° C.; and (2) that encode a polypeptide having at least 70%, at least 80%, at least 90%, at least 95% or greater than 95% sequence identity to the amino acid sequence of SEQ ID NOS:2, 5, 7, 9, 11, respectively.

Percent sequence identity is determined by conventional methods. See, for example, Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 4 (amino acids are indicated by the standard one-letter codes).

Total number of identical matches
——————×100
[length of the longer sequence plus the
number of gaps introduced into the longer
sequence in order to align the two sequences]

TABLE 5

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |

TABLE 5-continued

|   | A  | R  | N  | D  | C  | Q  | E  | G  | H  | I  | L  | K  | M  | F  | P  | S  | T  | W  | Y  | V |
|---|----|----|----|----|----|----|----|----|----|----|----|----|----|----|----|----|----|----|----|---|
| S | 1  | -1 | 1  | 0  | -1 | 0  | 0  | 0  | -1 | -2 | -2 | 0  | -1 | -2 | -1 | 4  |    |    |    |   |
| T | 0  | -1 | 0  | -1 | -1 | -1 | -1 | -2 | -2 | -1 | -1 | -1 | -1 | -2 | -1 | 1  | 5  |    |    |   |
| W | -3 | -3 | -4 | -4 | -2 | -2 | -3 | -2 | -2 | -3 | -2 | -3 | -1 | 1  | -4 | -3 | -2 | 11 |    |   |
| Y | -2 | -2 | -2 | -3 | -2 | -1 | -2 | -3 | 2  | -1 | -1 | -2 | -1 | 3  | -3 | -2 | -2 | 2  | 7  |   |
| V | 0  | -3 | -3 | -3 | -1 | -2 | -2 | -3 | -3 | 3  | 1  | -2 | 1  | -1 | -2 | -2 | 0  | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zcyto20. The FASTA algorithm is described by Pearson and Lipman, Proc. Nat'l Acad. Sci. USA 85:2444 (1988), and by Pearson, Meth. Enzymol. 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then restored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Preferred parameters for FASTA analysis are: ktup-1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variant zcyto20, zcyto21, and zcyto22 polypeptides or polypeptides with substantially similar sequence identity are characterized as having one or more amino acid substitutions, deletions or additions. These changes are preferably of a minor nature, that is conservative amino acid substitutions (see Table 5) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 154 to 235 amino acid residues that comprise a sequence that is at least 70%, preferably at least 90%, and more preferably 95%, 96%, 97%, 98%, 99% or more identical to the corresponding region of SEQ ID NO:2. Polypeptides comprising affinity tags can further comprise a proteolytic cleavage site between the zcyto20, zcyto21, zcyto22, zcyto24 and zcyto25 polypeptide and the affinity tag. Preferred such sites include thrombin cleavage sites and factor Xa cleavage sites.

TABLE 6

| Conservative amino acid substitutions | |
|---|---|
| Basic: | arginine |
|  | lysine |
|  | histidine |
| Acidic: | glutamic acid |
|  | aspartic acid |
| Polar: | glutamine |
|  | asparagine |
| Hydrophobic: | leucine |
|  | isoleucine |
|  | valine |
| Aromatic: | phenylalanine |
|  | tryptophan |
|  | tyrosine |
| Small: | glycine |
|  | alanine |
|  | serine |
|  | threonine |
|  | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, Current Opin. Struct. Biol. 5:372-376, 1995 and Cordes et al., Current Opin. Struct. Biol. 6:3-10, 1996). In general, when designing modifications to molecules or identifying specific fragments determination of structure will be accompanied by evaluating activity of modified molecules.

Amino acid sequence changes are made in zcyto20, zcyto21, zcyto22, zcyto24 and zcyto25 polypeptides so as to minimize disruption of higher order structure essential to biological activity. For example, where the zcyto20, zcyto21, zcyto22, zcyto24 and zcyto25 polypeptide comprises one or more helices, changes in amino acid residues will be made so as not to disrupt the helix geometry and other components of the molecule where changes in conformation abate some critical function, for example, binding of the molecule to its binding partners. The effects of amino acid sequence changes can be predicted by, for example, computer modeling as disclosed above or determined by analysis of crystal structure (see, e.g., Lapthorn et al., Nat. Struct. Biol. 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the zcyto20 protein sequence as shown in SEQ ID NO:2 can be generated (Hopp et al., *Proc. Natl. Acad. Sci.* 78:3 824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in zcyto20, hydrophilic regions include amino acid residues 169 (Glu) to 174 (Glu) of SEQ ID NO: 2, amino acid residues 54 (Lys) to 59 (Ala) of SEQ ID NO: 2, amino acid residues 53 (Phe) to 58 (Asp) of SEQ ID NO: 2, amino acid residues 168 (Gln) to 173 (Lys) of SEQ ID NO: 2, and amino acid residues 154 (Pro) to 159 (Arg) of SEQ ID NO: 2.

A Hopp/Woods hydrophilicity profile of the zcyto22 protein sequence as shown in SEQ ID NO:7 can be generated (Hopp et al., *Proc. Natl. Acad. Sci.* 78:3824-3828, 1981; Hopp, *J. Immun Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in zcyto22, hydrophilic regions include amino acid residues 169 (Glu) to 174 (Glu) of SEQ ID NO: 7, amino acid residues 54 (Lys) to 59 (Ala) of SEQ ID NO: 7, amino acid residues 53 (Phe) to 58 (Asp) of SEQ ID NO: 7, amino acid residues 168 (Gln) to 173 (Lys) of SEQ ID NO: 7, and amino acid residues 154 (Pro) to 159 (Arg) of SEQ ID NO: 7.

Those skilled in the art will recognize that hydrophilicity or hydrophobicity will be taken into account when designing modifications in the amino acid sequence of a zcyto20, zcyto21, zcyto22, zcyto24 and zcyto25 polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp.

The identities of essential amino acids can also be inferred from analysis of sequence similarity between INF-α and members of the family of zcyto20, zcyto21, zcyto22, zcyto24 and zcyto25 (as shown in Tables 1 and 2). Using methods such as "FASTA" analysis described previously, regions of high similarity are identified within a family of proteins and used to analyze amino acid sequence for conserved regions. An alternative approach to identifying a variant polynucleotide on the basis of structure is to determine whether a nucleic acid molecule encoding a potential variant zcyto20, zcyto21, zcyto22, zcyto24, and zcyto25 gene can hybridize to a nucleic acid molecule having the nucleotide sequence of SEQ ID NOS:1, 4, 6, 8, or 10 as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological or biochemical activity as disclosed below to identify amino acid residues that are critical to the activity of the molecule. See also, Hilton et al., *J. Biol. Chem.* 271:4699 (1996).

The present invention also includes functional fragments of zcyto20, zcyto21, zcyto22, zcyto24 and zcyto25 polypeptides and nucleic acid molecules encoding such functional fragments. A "functional" zcyto20, zcyto21, zcyto22, zcyto24 and zcyto25 or fragment thereof as defined herein is characterized by its proliferative or differentiating activity, by its ability to induce or inhibit specialized cell functions, or by its ability to bind specifically to an anti-zcyto20, zcyto21, zcyto22, zcyto24 and zcyto25 antibody or zcytor19 receptor (either soluble or immobilized). As previously described herein, zcyto20, zcyto21, zcyto22, zcyto24 and zcyto25 polypeptides are characterized by a six-helical-bundle. Thus, the present invention further provides fusion proteins encompassing: (a) polypeptide molecules comprising one or more of the helices described above; and (b) functional fragments comprising one or more of these helices. The other polypeptide portion of the fusion protein may be contributed by another helical-bundle cytokine or interferon, such as INF-α, or by a non-native and/or an unrelated secretory signal peptide that facilitates secretion of the fusion protein.

The zcyto20, zcyto21, zcyto22, zcyto24 and zcyto25 polypeptides of the present invention, including full-length polypeptides, biologically active fragments, and fusion polypeptides can be produced according to conventional techniques using cells into which have been introduced an expression vector encoding the polypeptide. As used herein, "cells into which have been introduced an expression vector" include both cells that have been directly manipulated by the introduction of exogenous DNA molecules and progeny thereof that contain the introduced DNA. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zcyto20, zcyto21, zcyto22, zcyto24 and zcyto25 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zcyto20, zcyto21, zcyto22, zcyto24 and zcyto25 polypeptide into the secretory pathway of a host cell, a secretory signal sequence (also known as a leader sequence, prepro sequence or pre sequence) is provided in the expression vector. The secretory signal sequence may be that of zcyto20, zcyto21, zcyto22, zcyto24 and zcyto25, or may be derived from another secreted protein (e.g., t-PA; see, U.S. Pat. No. 5,641,655) or synthesized de novo. The secretory signal sequence is operably linked to the zcyto20, zcyto21, zcyto22, zcyto24 and zcyto25 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells can be used as hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981; Graham and Van der Eb, *Virology* 52:456, 1973), electroporation (Neumann et al., *EMBO J.* 1:841-845, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59-72, 1977) and Chinese hamster ovary (e.g. CHO-K1, ATCC No. CCL 61; or CHO DG44, Chasin et al., *Som. Cell. Molec. Genet.* 12:555, 1986) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, Manassas, Va. USA under accession numbers 98669 and 98668, respectively, and derivatives thereof.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. In an alternative method, adenovirus vector-infected 293 cells can be grown as adherent cells or in suspension culture at relatively high cell density to produce significant amounts of protein (See Garnier et al., *Cytotechnol.* 15:145-55, 1994). With either protocol, an expressed, secreted heterologous protein can be repeatedly isolated from the cell culture supernatant, lysate, or membrane fractions depending on the disposition of the expressed protein in the cell. Within the infected 293 cell production protocol, non-secreted proteins can also be effectively obtained.

Insect cells can be infected with recombinant baculovirus, commonly derived from *Autographa californica* nuclear polyhedrosis virus (AcNPV) according to methods known in the art. Within a preferred method, recombinant baculovirus is produced through the use of a transposon-based system described by Luckow et al. (*J. Virol.* 67:4566-4579, 1993). This system, which utilizes transfer vectors, is commercially available in kit form (Bac-to-Bac™ kit; Life Technologies, Rockville, Md.). The transfer vector (e.g., pFastBac1™; Life Technologies) contains a Tn7 transposon to move the DNA encoding the protein of interest into a baculovirus genome maintained in *E. coli* as a large plasmid called a "bacmid." See, Hill-Perkins and Possee, *J. Gen. Virol.* 71:971-976, 1990; Banning et al., *J. Gen. Viral.* 75:1551-1556, 1994; and Chazenbalk and Rapoport, *J. Biol. Chem.* 270:1543-1549, 1995. In addition, transfer vectors can include an in-frame fusion with DNA encoding a polypeptide extension or affinity tag as disclosed above. Using techniques known in the art, a transfer vector containing a zcyto20-, zcyto21-, zcyto22-, zcyto24- and zcyto25-encoding sequence is transformed into *E. coli* host cells, and the cells are screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, such as Sf9 cells. Recombinant virus that expresses zcyto20, zcyto21, zcyto22, zcyto24 and zcyto25 protein is subsequently produced. Recombinant viral stocks are made by methods commonly used the art.

For protein production, the recombinant virus is used to infect host cells, typically a cell line derived from the fall armyworm, *Spodoptera frugiperda* (e.g., Sf9 or Sf21 cells) or *Trichoplusia ni* (e.g., High Five™ cells; Invitrogen, Carlsbad, Calif.). See, for example, U.S. Pat. No. 5,300,435. Serum-free media are used to grow and maintain the cells. Suitable media formulations are known in the art and can be obtained from commercial suppliers. The cells are grown up from an inoculation density of approximately $2$-$5 \times 10^5$ cells to a density of $1$-$2 \times 10^6$ cells, at which time a recombinant viral stock is added at a multiplicity of infection (MOI) of 0.1 to 10, more typically near 3. Procedures used are generally known in the art.

Other higher eukaryotic cells can also be used as hosts, including plant cells and avian cells. The use of *Agrobacte-*

*rium rhizogenes* as a vector for expressing genes in plant cells has been reviewed by Sinkar et al., *J. Biosci. (Bangalore)* 11:47-58, 1987.

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha, Schizosaccharomyces pombe, Kluyveromyces lactis, Kluyveromyces fragilis, Ustilago maydis, Pichia pastoris, Pichia methanolica, Pichia guillermondii* and *Candida maltosa* are known in the art. See, for example, Gleeson et al., *J. Gen. Microbial.* 132:3459-3465, 1986; Cregg, U.S. Pat. No. 4,882,279; and Raymond et al., *Yeast* 14, 11-23, 1998. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533. Production of recombinant proteins in *Pichia methanolica* is disclosed in U.S. Pat. Nos. 5,716,808, 5,736,383, 5,854,039, and 5,888,768.

Prokaryotic host cells, including strains of the bacteria *Escherichia coli, Bacillus* and other genera are also useful host cells within the present invention. Techniques for transforming these hosts and expressing foreign DNA sequences cloned therein are well known in the art (see, e.g., Sambrook et al., ibid.). When expressing a zcyto20, zcyto21, zcyto22, zcyto24 and zcyto25 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. Liquid cultures are provided with sufficient aeration by conventional means, such as shaking of small flasks or sparging of fermentors.

It is preferred to purify the polypeptides and proteins of the present invention to $\geq 80\%$ purity, more preferably to $\geq 90\%$ purity, even more preferably $\geq 95\%$ purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide or protein is substantially free of other polypeptides or proteins, particularly those of animal origin.

Expressed recombinant zcyto20, zcyto21, zcyto22, zcyto24 and zcyto25 proteins (including chimeric polypeptides and multimeric proteins) are purified by conventional protein purification methods, typically by a combination of chromatographic techniques. See, in general, *Affinity Chromatography Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321-1325, 1988. Proteins comprising a glu-glu tag can be purified by immunoaffinity chromatography according to conventional procedures. See, for example, Grussenmeyer et al., ibid. Maltose binding protein fusions are purified on an amylose column according to methods known in the art.

Zcyto20, zcyto21, zcyto22, zcyto24 and zcyto25 polypeptides can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989. In vitro synthesis is particularly advantageous for the preparation of smaller polypeptides.

Using methods known in the art, zcyto20, zcyto21, zcyto22, zcyto24 and zcyto25 proteins can be prepared as monomers or multimers; glycosylated or non-glycosylated; pegylated or non-pegylated; and may or may not include an initial methionine amino acid residue.

Target cells for use in zcyto20, zcyto21, zcyto22, zcyto24 and zcyto25 activity assays include, without limitation, vascular cells (especially endothelial cells and smooth muscle cells), hematopoietic (myeloid and lymphoid) cells, liver cells (including hepatocytes, fenestrated endothelial cells, Kupffer cells, and Ito cells), fibroblasts (including human dermal fibroblasts and lung fibroblasts), fetal lung cells, articular synoviocytes, pericytes, chondrocytes, osteoblasts, and prostate epithelial cells. Endothelial cells and hematopoietic cells are derived from a common ancestral cell, the hemangioblast (Choi et al., *Development* 125:725-732, 1998).

Zcyto20, zcyto21, zcyto22, zcyto24 and zcyto25 proteins of the present invention are characterized by their activity, that is, modulation of the proliferation, differentiation, migration, adhesion, or metabolism of responsive cell types. Biological activity of zcyto20, zcyto21, zcyto22, zcyto24 and zcyto25 proteins is assayed using in vitro or in vivo assays designed to detect cell proliferation, differentiation, migration or adhesion; or changes in cellular metabolism (e.g., production of other growth factors or other macromolecules). Many suitable assays are known in the art, and representative assays are disclosed herein. Assays using cultured cells are most convenient for screening, such as for determining the effects of amino acid substitutions, deletions, or insertions. However, in view of the complexity of developmental processes (e.g., angiogenesis, wound healing), in vivo assays will generally be employed to confirm and further characterize biological activity. Certain in vitro models, such as the three-dimensional collagen gel matrix model of Pepper et al. (*Biochem. Biophys. Res. Comm.* 189:824-831, 1992), are sufficiently complex to assay histological effects. Assays can be performed using exogenously produced proteins, or may be carried out in vivo or in vitro using cells expressing the polypeptide(s) of interest. Assays can be conducted using zcyto20 proteins alone or in combination with other growth factors, such as members of the VEGF family or hematopoietic cytokines (e.g., EPO, TPO, G-CSF, stem cell factor). Representative assays are disclosed below.

Activity of zcyto20, zcyto21, zcyto22, zcyto24 and zcyto25 proteins can be measured in vitro using cultured cells or in vivo by administering molecules of the claimed invention to an appropriate animal model. Assays measuring cell proliferation or differentiation are well known in the art. For example, assays measuring proliferation include such assays as chemosensitivity to neutral red dye (Cavanaugh et al., *Investigational New Drugs* 8:347-354, 1990), incorporation of radiolabelled nucleotides (as disclosed by, e.g., Raines and Ross, *Methods Enzymol.* 109:749-773, 1985; Wahl et al., *Mol. Cell. Biol.* 8:5016-5025, 1988; and Cook et al., Analytical Biochem. 179:1-7, 1989), incorporation of 5-bromo-2'-deoxyuridine (BrdU) in the DNA of proliferating cells (Porstmann et al., *J. Immunol. Methods* 82:169-179, 1985), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988). Differentiation can be assayed using suitable precursor cells that can be induced to differentiate into a more mature phenotype. Assays measuring differentiation include, for example, measuring cell-surface markers associated with stage-specific expression of a tissue, enzymatic activity, functional activity or morphological changes (Watt, *FASEB,* 5:281-284, 1991; Francis, *Differentiation* 57:63-75, 1994; Raes, *Adv. Anim. Cell Biol. Technol. Bioprocesses,* 161-171, 1989; all incorporated herein by reference).

Zcyto20, zcyto21, zcyto22, zcyto24 and zcyto25 activity may also be detected using assays designed to measure zcyto20-, zcyto21-, zcyto22-, zcyto24- and zcyto25-induced production of one or more additional growth factors or other macromolecules. Preferred such assays include those for determining the presence of hepatocyte growth factor (HGF), epidermal growth factor (EGF), transforming growth factor alpha (TGFα), interleukin-6 (IL-6), VEGF, acidic fibroblast growth factor (aFGF), angiogenin, and other macromolecules produced by the liver. Suitable assays include mitogenesis assays using target cells responsive to the macromolecule of interest, receptor-binding assays, competition binding assays, immunological assays (e.g., ELISA), and other formats known in the art. Metalloprotease secretion is measured from treated primary human dermal fibroblasts, synoviocytes and chondrocytes. The relative levels of collagenase, gelatinase and stromalysin produced in response to culturing in the presence of a zcyto20, zcyto21, zcyto22, zcyto24 and zcyto25 protein is measured using zymogram gels (Loita and Stetler-Stevenson, *Cancer Biology* 1:96-106, 1990). Procollagen/collagen synthesis by dermal fibroblasts and chondrocytes in response to a test protein is measured using $^3$H-proline incorporation into nascent secreted collagen. $^3$H-labeled collagen is visualized by SDS-PAGE followed by autoradiography (Unemori and Amento, *J. Biol. Chem.* 265: 10681-10685, 1990). Glycosaminoglycan (GAG) secretion from dermal fibroblasts and chondrocytes is measured using a 1,9-dimethylmethylene blue dye binding assay (Farndale et al., *Biochim. Biophys. Acta* 883:173-177, 1986). Collagen and GAG assays are also carried out in the presence of IL-1α or TGF-α to examine the ability of zcyto20 protein to modify the established responses to these cytokines.

Certain members of the protein family comprising zcyto20, zcyto21, zcyto22, zcyto24 and zcyto25 have been shown to increase circulating monocyte numbers in vivo. Monocyte activation is important in both innate and adaptive immunity. For example, activation of monocytes has been shown to stimulate antigen presentation by several mechanisms. Antigen presentation promotes activation and proliferation of T-cells, both cytotoxic and helper T cells. The maturation and activation dendritic cells also promotes activation of T cells and both innate and adaptive immunity. Increases in activated monocytes and macrophages have also been shown to increase cytolytic activity. Therefore, zcyto20, zcyto21, zcyto22, zcyto24 and zcyto25 will be useful as an anti-infectious agent, enhancing innate, cell-mediated and humoral immune responses. Increases in ICAM staining in CD14+ monocytes was seen suggesting that zcyto20, zcyto21, zcyto22, zcyto24 and zcyto25 play a role in monocyte activation. While data show that family members promote an anti-viral response to virus, bacteria and parasites may also be affected.

Monocyte activation assays are carried out (1) to look for the ability of zcyto20, zcyto21, zcyto22, zcyto24 and zcyto25 proteins to further stimulate monocyte activation, and (2) to examine the ability of zcyto20, zcyto21, zcyto22, zcyto24 and zcyto25 proteins to modulate attachment-induced or endotoxin-induced monocyte activation (Fuhlbrigge et al., *J. Immunol.* 138: 3799-3802, 1987). IL-1α and TNFα levels produced in response to activation are measured by ELISA (Biosource, Inc. Camarillo, Calif.). Monocyte/macrophage cells, by virtue of CD14 (LPS receptor), are exquisitely sensitive to endotoxin, and proteins with moderate levels of endotoxin-like activity will activate these cells.

Increased levels of monocytes suggest that zcyto20, zcyto21, zcyto22, zcyto24 and zcyto25 may have a direct effect on myeloid progenitor cells in the bone marrow. Increasing differentiation of myeloid progenitor cells to monocytes is essential in restoring immunocompetency, for example, after chemotherapy. Thus, administration of zcyto20, zcyto21, zcyto22, zcyto24 and zcyto25 to patients receiving chemotherapy could promote their recovery and ability to resist infection commonly associated with chemotherapy regimens. Thus, methods for expanding the numbers of monocytes or monocyte progenitor cells by either culturing bone marrow or peripheral blood cells with the molecules of the present invention such that there is an increase in the monocyte or monocyte progenitor cells for achieving this effect in vitro or ex vivo. The present invention also provides for the in vivo administration of the molecules of the present invention to a mammal needing increased monocyte or monocyte progenitor cells. Increased monocyte and monocyte progenitor cells can be measured using methods well known to clinicians, physicians, and other persons skilled the art. Monocyte cells are included in the myeloid lineage of hematopoietic cells, so affects on other cells in that lineage would not be unusual. For example, when a factor facilitates the differentiation or proliferation of one type of cell in the myeloid or lymphoid lineage, this can affect production of other cells with a common progenitor or stem cell.

Hematopoietic activity of zcyto20, zcyto21, zcyto22, zcyto24 and zcyto25 proteins can be assayed on various hematopoietic cells in culture. Preferred assays include primary bone marrow colony assays and later stage lineage-restricted colony assays, which are known in the art (e.g., Holly et al., WIPO Publication WO 95/21920). Marrow cells plated on a suitable semi-solid medium (e.g., 50% methylcellulose containing 15% fetal bovine serum, 10% bovine serum albumin, and 0.6% PSN antibiotic mix) are incubated in the presence of test polypeptide, then examined microscopically for colony formation. Known hematopoietic factors are used as controls. Mitogenic activity of zcyto20, zcyto21, zcyto22, zcyto24 and zcyto25 polypeptides on hematopoietic cell lines can be measured as disclosed above.

Cell migration is assayed essentially as disclosed by Kähler et al. (*Arteriosclerosis, Thrombosis, and Vascular Biology* 17:932-939, 1997). A protein is considered to be chemotactic if it induces migration of cells from an area of low protein concentration to an area of high protein concentration. A typical assay is performed using modified Boyden chambers with a polystryrene membrane separating the two chambers (Transwell; Corning Costar Corp.). The test sample, diluted in medium containing 1% BSA, is added to the lower chamber of a 24-well plate containing Transwells. Cells are then placed on the Transwell insert that has been pretreated with 0.2% gelatin. Cell migration is measured after 4 hours of incubation at 37° C. Non-migrating cells are wiped off the top of the Transwell membrane, and cells attached to the lower face of the membrane are fixed and stained with 0.1% crystal violet. Stained cells are then extracted with 10% acetic acid and absorbance is measured at 600 nm. Migration is then calculated from a standard calibration curve. Cell migration can also be measured using the matrigel method of Grant et al. ("Angiogenesis as a component of epithelial-mesenchymal interactions" in Goldberg and Rosen, *Epithelial-Mesenchymal Interaction in Cancer*, Birkhäuser Verlag, 1995, 235-248; Baatout, *Anticancer Research* 17:451-456, 1997).

Cell adhesion activity is assayed essentially as disclosed by LaFleur et al. (*J. Biol. Chem.* 272:32798-32803, 1997). Briefly, microtiter plates are coated with the test protein, non-specific sites are blocked with BSA, and cells (such as smooth muscle cells, leukocytes, or endothelial cells) are plated at a density of approximately $10^4$-$10^5$ cells/well. The wells are incubated at 37° C. (typically for about 60 minutes), then non-adherent cells are removed by gentle washing. Adhered cells are quantitated by conventional methods (e.g., by staining with crystal violet, lysing the cells, and determining the optical density of the lysate). Control wells are coated with a known adhesive protein, such as fibronectin or vitronectin.

The activity of zcyto20, zcyto21, zcyto22, zcyto24 and zcyto25 proteins can be measured with a silicon-based biosensor microphysiometer that measures the extracellular acidification rate or proton excretion associated with receptor binding and subsequent physiologic cellular responses. An exemplary such device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell et al., *Science* 257:1906-1912, 1992; Pitchford et al., *Meth. Enzymol.* 228: 84-108, 1997; Arimilli et al., *J. Immunol. Meth.* 212:49-59, 1998; and Van Liefde et al., *Eur. J. Pharmacol.* 346:87-95, 1998. The microphysiometer can be used for assaying adherent or non-adherent eukaryotic or prokaryotic cells. By measuring extracellular acidification changes in cell media over time, the microphysiometer directly measures cellular responses to various stimuli, including zcyto20, zcyto21, zcyto22, zcyto24 and zcyto25 proteins, their agonists, and antagonists. Preferably, the microphysiometer is used to measure responses of a zcyto20-, zcyto21-, zcyto22-, zcyto24- and zcyto25-responsive eukaryotic cell, compared to a control eukaryotic cell that does not respond to zcyto20, zcyto21, zcyto22, zcyto24 and zcyto25 polypeptide. Zcyto20-, zcyto21-, zcyto22-, zcyto24- and zcyto25-responsive eukaryotic cells comprise cells into which a receptor for zcyto20, zcyto21, zcyto22, zcyto24 and zcyto25 has been transfected, thereby creating a cell that is responsive to zcyto20, zcyto21, zcyto22, zcyto24 and zcyto25, as well as cells naturally responsive to zcyto20, zcyto21, zcyto22, zcyto24 and zcyto25. Differences, measured by a change, for example, an increase or diminution in extracellular acidification, in the response of cells exposed to zcyto20, zcyto21, zcyto22, zcyto24 and zcyto25 polypeptide, relative to a control not exposed to zcyto20, zcyto21, zcyto22, zcyto24 and zcyto25, are a direct measurement of zcyto20-, zcyto21-, zcyto22-, zcyto24- and zcyto25-modulated cellular responses. Moreover, such zcyto20-, zcyto21-, zcyto22-, zcyto24- and zcyto25-modulated responses can be assayed under a variety of stimuli. The present invention thus provides methods of identifying agonists and antagonists of zcyto20, zcyto21, zcyto22, zcyto24 and zcyto25 proteins, comprising providing cells responsive to a zcyto20, zcyto21, zcyto22, zcyto24 and zcyto25 polypeptide, culturing a first portion of the cells in the absence of a test compound, culturing a second portion of the cells in the presence of a test compound, and detecting a change, for example, an increase or diminution, in a cellular response of the second portion of the cells as compared to the first portion of the cells. The change in cellular response is shown as a measurable change in extracellular acidification rate. Culturing a third portion of the cells in the presence of a zcyto20, zcyto21, zcyto22, zcyto24 and zcyto25 protein and the absence of a test compound provides a positive control for the zcyto20-, zcyto21-, zcyto22-, zcyto24- and zcyto25-responsive cells and a control to compare the agonist activity of a test compound with that of the zcyto20, zcyto21, zcyto22, zcyto24 and zcyto25 polypeptide. Antagonists of zcyto20, zcyto21, zcyto22, zcyto24 and zcyto25 can be identified by exposing the cells to zcyto20, zcyto21, zcyto22, zcyto24 and zcyto25 protein in the presence and absence of the test compound, whereby a reduction in zcyto20-, zcyto21-, zcyto22-, zcyto24- and zcyto25-stimulated activity is indicative of antagonist activity in the test compound.

Expression of zcyto20, zcyto21, zcyto22, zcyto24 and zcyto25 polynucleotides in animals provides models for further study of the biological effects of overproduction or inhibition of protein activity in vivo. Zcyto20-, zcyto21-, zcyto22-, zcyto24- and zcyto25-encoding polynucleotides and antisense polynucleotides can be introduced into test animals, such as mice, using viral vectors or naked DNA, or transgenic animals can be produced.

One in vivo approach for assaying proteins of the present invention utilizes viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acids. For review, see Becker et al., *Meth. Cell Biol.* 43:161-89, 1994; and Douglas and Curiel, *Science & Medicine* 4:44-53, 1997. The adenovirus system offers several advantages. Adenovirus can (i) accommodate relatively large DNA inserts; (ii) be grown to high-titer; (iii) infect a broad range of mammalian cell types; and (iv) be used with many different promoters including ubiquitous, tissue specific, and regulatable promoters. Because adenoviruses are stable in the bloodstream, they can be administered by intravenous injection.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621-14624, 1988; Wu et al., *J. Biol. Chem.* 267:963-967, 1992; and Johnston and Tang, *Meth. Cell Biol.* 43:353-365, 1994.

Transgenic mice, engineered to express a zcyto20, zcyto21, zcyto22, zcyto24 and zcyto25 gene, and mice that exhibit a complete absence of zcyto20, zcyto21, zcyto22, zcyto24 and zcyto25 gene function, referred to as "knockout mice" (Snouwaert et al., *Science* 257:1083, 1992), can also be generated (Lowell et al., *Nature* 366:740-742, 1993). These mice can be employed to study the zcyto20, zcyto21, zcyto22, zcyto24 and zcyto25 gene and the protein encoded thereby in an in vivo system. Transgenic mice are particularly useful for investigating the role of zcyto20, zcyto21, zcyto22, zcyto24 and zcyto25 proteins in early development in that they allow the identification of developmental abnormalities or blocks resulting from the over- or underexpression of a specific factor. See also, Maisonpierre et al., *Science* 277:55-60, 1997 and Hanahan, *Science* 277:48-50, 1997. Preferred promoters for transgenic expression include promoters from metallothionein and albumin genes.

A loss of normal inhibitory control of muscle contraction has been associated with damage or perturbation of selected gamma-aminobutryric acid-secreting neurons. For example, Stiff Man Syndrome exhibit remarkable stiffness of musculature, believed to be mediated through interference of the functioning of their gamma-aminobutyric acid (GABA) producing neurons. Other related neuromuscular disorders include myotonia, metabolic myopathies, Isaac's syndrome, dystonia, and tetanic spasms (Valldeoriola, *J. Neurol* 246: 423-431, 1999).

Similarly, direct measurement of zcyto20, zcyto21, zcyto22, zcyto24 and zcyto25 polypeptide, or its loss of expression in a tissue can be determined in a tissue or cells as they undergo tumor progression. Increases in invasiveness and motility of cells, or the gain or loss of expression of zcyto20, zcyto21, zcyto22, zcyto24 and zcyto25 in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zcyto20, zcyto21, zcyto22, zcyto24 and zcyto25 expression. For example, appearance or disappearance of polypeptides that regulate cell motility can be used to aid diagnosis and prognosis of prostate cancer (Banyard, J. and Zetter, B. R., *Cancer and Metast. Rev.* 17:449-458, 1999). As an effector of cell motility, or as a liver-specific marker, zcyto20, zcyto21, zcyto22, zcyto24 and zcyto25 gain or loss of expression may serve as a diagnostic for brain and other cancers. Moreover, analogous to the prostate specific antigen (PSA), increased levels of zcyto20, zcyto21, zcyto22, zcyto24 and zcyto25 polypeptides, or anti-zcyto20, anti-zcyto21, anti-zcyto22, anti-zcyto24 and anti-zcyto25 antibodies in a patient, relative to a normal control can be indicative of brain and other cancers (See, e.g., Mulders, TMT, et al., *Eur. J. Surgical Oncol.* 16:37-41, 1990). Strong zcyto20, zcyto21, zcyto22, zcyto24 and zcyto25 expression in tissue not normally found to express the polynucleotides would serve as a diagnostic of an abnormality in the cell or tissue type, of invasion or metastasis of cancerous liver tissue into non-liver tissue, and could aid a physician in directing further testing or investigation, or aid in directing therapy.

In addition, zcyto20, zcyto21, zcyto22, zcyto24 and zcyto25 polynucleotide probes, anti-zcyto20, zcyto21, zcyto22, zcyto24 and zcyto25 antibodies, and detection the presence of zcyto20, zcyto21, zcyto22, zcyto24 and zcyto25 polypeptides in tissue can be used to assess whether brain or other tissue found to normally express zcyto20, zcyto21, zcyto22, zcyto24 and zcyto25 is present, for example, after surgery involving the excision of a diseased or cancerous liver or neuronal tissue. As such, the polynucleotides, polypeptides, and antibodies of the present invention can be used as an aid to determine whether all tissue is excised after surgery, for example, after surgery for brain and other cancers. In such instances, it is especially important to remove all potentially diseased tissue to maximize recovery from the cancer, and to minimize recurrence. Preferred embodiments include fluorescent, radiolabeled, or calorimetrically labeled anti-zcyto20 antibodies and zcyto20, zcyto21, zcyto22, zcyto24 and zcyto25 polypeptide binding partners, that can be used histologically or in situ.

Moreover, the activity and effect of zcyto20, zcyto21, zcyto22, zcyto24 and zcyto25 on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6 mouse, that are readily cultured and manipulated in vitro. Tumors resulting from implantation of either of these cell lines are capable of metastasis to the lung in C57BL6 mice. The Lewis lung carcinoma model has recently been used in mice to identify an inhibitor of angiogenesis (O'Reilly M S, et al. *Cell* 79: 315-328,1994). C57BL6/J mice are treated with an experimental agent either through daily injection of recombinant protein, agonist or antagonist or a one-time injection of recombinant adenovirus. Three days following this treatment, $10^5$ to $10^6$ cells are implanted under the dorsal skin. Alternatively, the cells themselves may be infected with recombinant adenovirus, such as one expressing zcyto20, zcyto21, zcyto22, zcyto24 or zcyto25, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 mm$^3$ in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., zcyto20, zcyto21, zcyto22, zcyto24 or zcyto25, on the ability of the tumor to recruit vasculature and undergo metastasis can thus be assessed. In addition, aside from using adenovirus, the implanted cells can be transiently transfected with zcyto20, zcyto21, zcyto22, zcyto24 or zcyto25. Use of stable zcyto20, zcyto21, zcyto22, zcyto24 and zcyto25 transfectants as well as use of induceable promoters to activate zcyto20, zcyto21, zcyto22, zcyto24 and zcyto25 expression in vivo are known in the art and can be used in this system to assess zcyto20 induction of metastasis. Moreover, purified zcyto20, zcyto21, zcyto22, zcyto24 and zcyto25 or zcyto20-, zcyto21-, zcyto22-, zcyto24- and zcyto25-conditioned media can be directly injected in to this mouse model, and hence be used in this system. For general reference see, O'Reilly M S, et al. *Cell* 79:315-328, 1994; and Ruscian D, et al. Murine Models of Liver Metastasis. *Invasion Metastasis* 14:349-361, 1995.

Antisense methodology can be used to inhibit zcyto20 gene transcription to examine the effects of such inhibition in vivo. Polynucleotides that are complementary to a segment of a zcyto20-, zcyto21-, zcyto22-, zcyto24- and zcyto25-encoding polynucleotide (e.g., a polynucleotide as set forth in SEQ ID NO:1) are designed to bind to zcyto20-, zcyto21-, zcyto22-, zcyto24- and zcyto25-encoding mRNA and to inhibit translation of such mRNA. Such antisense oligonucleotides can also be used to inhibit expression of zcyto20, zcyto21, zcyto22, zcyto24 and zcyto25 polypeptide-encoding genes in cell culture.

Most cytokines as well as other proteins produced by activated lymphocytes play an important biological role in cell differentiation, activation, recruitment and homeostasis of cells throughout the body. Zcyto20, zcyto21, zcyto22, zcyto24 and zcyto25 and inhibitors of their activity are expected to have a variety of therapeutic applications. These therapeutic applications include treatment of diseases which require immune regulation, including autoimmune diseases such as rheumatoid arthritis, multiple sclerosis, myasthenia gravis, systemic lupus erythematosis, and diabetes. Zcyto20, zcyto21, zcyto22, zcyto24 and zcyto25 may be important in the regulation of inflammation, and therefore would be useful in treating rheumatoid arthritis, asthma and sepsis. There may be a role of zcyto20, zcyto21, zcyto22, zcyto24 and zcyto25 in mediating tumorgenesis, whereby a zcyto20, zcyto21, zcyto22, zcyto24 and zcyto25 antagonist would be useful in the treatment of cancer. Zcyto20, zcyto21, zcyto22, zcyto24 and zcyto25 may be useful in modulating the immune system, whereby zcyto20, zcyto21, zcyto22, zcyto24 and zcyto25 and zcyto20, zcyto21, zcyto22, zcyto24 and zcyto25 antagonists may be used for reducing graft rejection, preventing graft-vs-host disease, boosting immunity to infectious diseases, treating immunocompromised patients (e.g., HIV$^+$ patients), or in improving vaccines.

Members of the protein family of the present invention have been shown to have an antiviral effect that is similar to interferon-α. Interferon has been approved in the United States for treatment of autoimmune diseases, condyloma acuminatum, chronic hepatitis C, bladder carcinoma, cervical carcinoma, laryngeal papillomatosis, fungoides mycosis, chronic hepatitis B, Kaposi's sarcoma in patients infected with human immunodeficiency virus, malignant melanoma, hairy cell leukemia, and multiple sclerosis. In addition, zcyto20, zcyto21, zcyto22, zcyto24 and zcyto25 may be used to treat forms of arteriosclerosis, such as atherosclerosis, by inhibiting cell proliferation. Accordingly, the present invention contemplates the use of proteins, polypeptides, and peptides having zcyto20 activity to treat such conditions, as well as to treat retinopathy. The present invention also contemplates the use of proteins, polypeptides, and peptides having zcyto20, zcyto21, zcyto22, zcyto24 and zcyto25 activity to treat lymphoproliferative disorders, including B-cell lymphomas, chronic lymphocytic leukemia, acute lymphocytic leukemia, Non-Hodkin's lymphomas, multiple myeloma, acute myelocytic leukemia, chronic myelocytic leukemia.

Interferons have also been shown to induce the expression of antigens by cultured cells (see, for example, Auth et al., *Hepatology* 18:546 (1993), Guadagni et al., *Int. J. Biol. Markers* 9:53 (1994), Girolomoni et al., *Eur. J. Immunol.* 25:2163 (1995), and Maciejewski et al., *Blood* 85:3183 (1995). This activity enhances the ability to identify new tumor associated antigens in vitro. Moreover, the ability of interferons to augment the level of expression of human tumor antigens indicates that interferons can be useful in an adjuvant setting for immunotherapy or enhance immunoscintigraphy using anti-tumor antigen antibodies (Guadagni et al., *Cancer Immunol. Immunother.* 26:222 (1988); Guadagni et al., *Int. J. Biol. Markers* 9:53 (1994)). Thus, the present invention includes the use of proteins, polypeptides and peptides having zcyto20, zcyto21, zcyto22, zcyto24 and zcyto25 activity as an adjuvant for immunotherapy or to improve immunoscintigraphy using anti-tumor antigen antibodies.

Methods for detection and diagnosis of viral infections are well known to those skilled in the art. The exact method used for measuring a reduction in virus in response to administration of molecules of the present invention will be dependent upon the patient, type of viral infection, and the like. For example, methods include, but are not limited to, measuring changes in CD4 cell counts, serologic tests, measuring the DNA of the virus and RNA of the virus by conventional and real-time quantitative polymerase chain reaction assays, viral induced antibody levels, immunofluorescence and enzyme-linked immunosorbant assays, cytopathic effects, and histology.

Moreover, zcyto20, zcyto21, zcyto22, zcyto24 and zcyto25 may bind CD4 or another leukocyte receptor and exhibit antiviral effects, for example, against human immunodeficiency virus (HIV) or human T-cell lymphotropic virus (HTLV). Alternatively, zcyto20 polypeptide may compete for a viral receptor or co-receptor to block viral infection. Zcyto20 may be given parentally to prevent viral infection or to reduce ongoing viral replication and re-infection (Gayowski, T. et al., *Transplantation* 64:422-426, 1997). Thus, zcyto20 may be used as an antiviral therapeutic, for example, for viral leukemias (HTLV), AIDS (HIV), or gastrointestinal viral infections caused by, for example, rotavirus, calicivirus (e.g., Norwalk Agent) and certain strains of pathogenic adenovirus, Hepatitis B and C.

Zcyto20, zcyto21, zcyto22, zcyto24 and zcyto25 can also be used to treat myocarditis, a disorder that arises when the heart is involved in an inflammatory process. The infiltration of lymphocytes and myocytolysis is thought to result after infection by virus, bacteria, fungi or parasites (see, for example, Brodison et al., *J. Infection* 37:99 (1998)). Zcyto20, zcyto21, zcyto22, zcyto24 and zcyto25 can be injected intravenously or subcutaneously to treat infections associated with myocarditis. Zcyto20, zcyto21, zcyto22, zcyto24 and zcyto25 can also be administered intravenously as an immunoregulatory cytokine in the treatment of autoimmune myocarditis. Interferon dosages can be extrapolated using a autoimmune model of myocarditis in the A/L mouse (Donermeyer, et al., *J. Exp. Med.* 182:1291 (1995)).

Exogenous administration of interferon-r in sheep increases the pregnancy rate (Aggarwal, *Human Cytokines III*, (Blackwell Science 1997)). As described herein, Zcyto20 mRNA is expressed in placenta. Accordingly, the present invention includes the use of zcyto20, zcyto21, zcyto22, zcyto24 and zcyto25, such as the disclosed human zcyto20, zcyto21, and zcyto22, to promote and protect growth of the fetus. As an illustration, zcyto20, zcyto21, and zcyto22 can be used to protect a developing fetus from viral infection (e.g., human immunodeficiency virus, human papilloma virus, and the like). In addition, zcyto20, zcyto21, zcyto22, zcyto24 and zcyto25 can be used to promote in vitro fertilization.

Recent reports have highlighted the role of type I interferons in the prevention of viral-induced diabetes by inducing a strong antiviral state in pancreatic beta cells early during viral infection (Flodstroem et al., *Nature Immunology* 3, 373-382 (2002)). This prevents the loss of beta cells due to viral-induced cell death and autoimmunity that accompanies it. Zcyto20, 21 and 22 also induce an antiviral state in cells that express their receptor, zcytor19. Zcytor19 is highly expressed in pancreatic tissue and therefore zcyto20-22 may play a role in prevention of viral-induced diabetes due to beta cell death. In addition, the role of type I interferons in prevention of viral-induced diabetes may be extended to other viral-induced autoimmune diseases and therefore, zcyto20-22 may also play a role in prevention of other diseases such as muscular sclerosis, lupus, and viral-induced autoimmune diseases in tissues that express the zcyto20-22 receptor, zcytor19.

Chronic systemic expression of type I interferons has also been associated with the pathogenesis of type I diabetes. Given the similarity of type I interferons to zcyto20-22 in regards to biological activity and gene induction, chronic systemic expression of zcyto20, 21, or 22 might also play a role in the pathogenesis of type I diabetes. Therefore, an inhibitor of zcyto20-22 activity in the pancreas might be beneficial in prevention of type I diabetes.

Zcyto20, zcyto21, zcyto22, zcyto24 and zcyto25 polypeptides can be administered alone or in combination with other vasculogenic or angiogenic agents, including VEGF. When using zcyto20, zcyto21, zcyto22, zcyto24 and zcyto25 in combination with an additional agent, the two compounds can be administered simultaneously or sequentially as appropriate for the specific condition being treated.

Zcyto20, zcyto21, zcyto22, zcyto24 and zcyto25 will be useful in treating tumorgenesis, and therefore would be useful in the treatment of cancer. A zcyto20 inhibition of anti-IgM stimulated normal B-cells and a similar effect is observed in B-cell tumor lines suggest that there may be therapeutic benefit in treating patients with the zcyto20, zcyto21, zcyto22, zcyto24 and zcyto25 in order to induce the B cell tumor cells into a less proliferative state. The ligand could be administered in combination with other agents already in use including both conventional chemotherapeutic agents as well as immune modulators such as interferon alpha. Alpha/beta interferons have been shown to be effective in treating some leukemias and animal disease models, and the growth inhibitory effects of interferon-alpha and zcyto20 may be additive for B-cell tumor-derived cell lines.

The present invention provides a method of reducing proliferation of a neoplastic B or T cells comprising administering to a mammal with a B or T cell neoplasm an amount of a composition of zcyto20 sufficient to reduce proliferation of the neoplastic B or T cells. Zcyto20, zcyto21, zcyto22, zcyto24 and zcyto25 stimulation of lytic NK cells from marrow progenitors and the proliferation of T-cells following activation of the antigen receptors would enhance treatment for patients receiving allogenic marrow transplants, and therefore, zcyto20, zcyto21, zcyto22, zcyto24 and zcyto25 will enhance the generation of anti-tumor responses, with or without the infusion of donor lymphocytes.

In another aspect, the present invention provides a method of reducing proliferation of a neoplastic B or T cells comprising administering to a mammal with a B or T cell neoplasm an amount of a composition of zcyto20 antagonist sufficient to reducing proliferation of the neoplastic B or T cells. Furthermore, the zcyto20 antagonist can be a ligand/toxin fusion protein.

A zcyto20-, zcyto21-, zcyto22-, zcyto24- and zcyto25-saporin fusion toxin may be employed against a similar set of leukemias and lymphomas, extending the range of leukemias that can be treated with zcyto20, zcyto21, zcyto22, zcyto24 and zcyto25. Fusion toxin mediated activation of the zcyto20 receptor provides two independent means to inhibit the growth of the target cells, the first being identical to the effects seen by the ligand alone, and the second due to delivery of the toxin through receptor internalization.

For pharmaceutical use, zcyto20, zcyto21, zcyto22, zcyto24 and zcyto25 proteins are formulated for topical or parenteral, particularly intravenous or subcutaneous, delivery according to conventional methods. In general, pharmaceutical formulations will include a zcyto20, zcyto21, zcyto22, zcyto24 and zcyto25 polypeptide in combination with a pharmaceutically acceptable vehicle, such as saline, buffered saline, 5% dextrose in water, or the like. Formulations may further include one or more excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. Zcyto20, zcyto21, zcyto22, zcyto24 and zcyto25 will preferably be used in a concentration of about 10 to 100 µg/ml of total volume, although concentrations in the range of 1 ng/ml to 1000 µg/ml may be used. For topical application, such as for the promotion of wound healing, the protein will be applied in the range of 0.1-10 µg/cm$^2$ of wound area, with the exact dose determined by the clinician according to accepted standards, taking into account the nature and severity of the condition to be treated, patient traits, etc. Determination of dose is within the level of ordinary skill in the art. Dosing is daily or intermittently over the period of treatment. Intravenous administration will be by bolus injection or infusion over a typical period of one to several hours. Sustained release formulations can also be employed. In general, a therapeutically effective amount of zcyto20 is an amount sufficient to produce a clinically significant change in the treated condition, such as a clinically significant change in hematopoietic or immune function, a significant reduction in morbidity, or a significantly increased histological score.

Zcyto20, zcyto21, zcyto22, zcyto24 and zcyto25 proteins, agonists, and antagonists are useful for modulating the expansion, proliferation, activation, differentiation, migration, or metabolism of responsive cell types, which include both primary cells and cultured cell lines. Of particular interest in this regard are hematopoietic cells, mesenchymal cells (including stem cells and mature myeloid and lymphoid cells), endothelial cells, smooth muscle cells, fibroblasts, hepatocytes, neural cells and embryonic stem cells. Zcyto20, zcyto21, zcyto22, zcyto24 and zcyto25 polypeptides are added to tissue culture media for these cell types at a concentration of about 10 pg/ml to about 100 ng/ml. Those skilled in the art will recognize that zcyto20 proteins can be advantageously combined with other growth factors in culture media.

Within the laboratory research field, zcyto20, zcyto21, zcyto22, zcyto24 and zcyto25 proteins can also be used as molecular weight standards or as reagents in assays for determining circulating levels of the protein, such as in the diagnosis of disorders characterized by over- or under-production of zcyto20 protein or in the analysis of cell phenotype.

Zcyto20, zcyto21, zcyto22, zcyto24 and zcyto25 proteins can also be used to identify inhibitors of their activity. Test compounds are added to the assays disclosed above to identify compounds that inhibit the activity of zcyto20 protein. In addition to those assays disclosed above, samples can be tested for inhibition of zcyto20 activity within a variety of assays designed to measure receptor binding or the stimulation/inhibition of zcyto20-, zcyto21-, zcyto22-, zcyto24- and zcyto25-dependent cellular responses. For example, zcyto20-, zcyto21-, zcyto22-, zcyto24- and zcyto25-responsive cell lines can be transfected with a reporter gene construct that is responsive to a zcyto20-, zcyto21-, zcyto22-, zcyto24- and zcyto25-stimulated cellular pathway. Reporter gene constructs of this type are known in the art, and will generally comprise a zcyto20-, zcyto21-, zcyto22-, zcyto24- and zcyto25-activated serum response element (SRE) operably linked to a gene encoding an assayable protein, such as luciferase. Candidate compounds, solutions, mixtures or extracts are tested for the ability to inhibit the activity of zcyto20, zcyto21, zcyto22, zcyto24 and zcyto25 on the target cells as evidenced by a decrease in zcyto20, zcyto21, zcyto22, zcyto24 and zcyto25 stimulation of reporter gene expression. Assays of this type will detect compounds that directly block zcyto20, zcyto21, zcyto22, zcyto24 and zcyto25 binding to cell-surface receptors, as well as compounds that block processes in the cellular pathway subsequent to receptor-ligand binding. In the alternative, compounds or other samples can be tested for direct blocking of zcyto20, zcyto21, zcyto22, zcyto24 and zcyto25 binding to receptor using zcyto20, zcyto21, zcyto22, zcyto24 and zcyto25 tagged with a detectable label (e.g., $^{125}$I, biotin, horseradish peroxidase, FITC, and the like). Within assays of this type, the ability of a test sample to inhibit the binding of labeled zcyto20, zcyto21, zcyto22, zcyto24 and zcyto25 to the receptor is indicative of inhibitory activity, which can be confirmed through secondary assays. Receptors used within binding assays may be cellular receptors or isolated, immobilized receptors.

As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Antibodies are defined to be specifically binding if they bind to a zcyto20, zcyto21, zcyto22, zcyto24 and zcyto25 polypeptide or protein with an affinity at least 10-fold greater than the binding affinity to control (non-zcyto20, zcyto21, zcyto22, zcyto24 and zcyto25) polypeptide or protein. The affinity of a monoclonal antibody can be readily determined by one of ordinary skill in the art (see, for example, Scatchard, *Ann. NY Acad. Sci.* 51: 660-672, 1949).

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, Fla., 1982, which is incorporated herein by reference). Of particular interest are generating antibodies to hydrophilic antigenic sites which include, for example, amino acid residues 169 (Glu) to 174 (Glu) of SEQ ID NO: 2, amino acid residues 54 (Lys) to 59 (Ala) of SEQ ID NO: 2, amino acid residues 53 (Phe) to 58 (Asp) of SEQ ID NO: 2, amino acid residues 168 (Gln) to 173 (Lys) of SEQ ID NO: 2, and amino acid residues 154 (Pro) to 159 (Arg) of SEQ ID NO: 2. For example, in zcyto22, hydrophilic regions include amino acid residues 169 (Glu) to 174 (Glu) of SEQ ID NO: 7, amino acid residues 54 (Lys) to 59 (Ala) of SEQ ID NO: 7, amino acid residues 53 (Phe) to 58 (Asp) of SEQ ID NO: 7, amino acid residues 168 (Gln) to 173 (Lys) of SEQ ID NO: 7, and amino acid residues 154 (Pro) to 159 (Arg) of SEQ ID NO: 7 would be useful. As would be evident to one of ordinary skill in the art, polyclonal antibodies can be generated from a variety of warm-blooded animals such as horses, cows, goats, sheep, dogs, chickens, rabbits, mice, and rats. The immunogenicity of a zcyto20, zcyto21, zcyto22, zcyto24 and zcyto25 polypeptide may be increased through the use of an adjuvant such as alum (aluminum hydroxide) or Freund's complete or incomplete adjuvant. Polypeptides useful for immunization also include fusion polypeptides, such as fusions of a zcyto20, zcyto21, zcyto22, zcyto24 and zcyto25 polypeptide or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

Alternative techniques for generating or selecting antibodies include in vitro exposure of lymphocytes to zcyto20, zcyto21, zcyto22, zcyto24 and zcyto25 polypeptides, and selection of antibody display libraries in phage or similar vectors (e.g., through the use of immobilized or labeled zcyto20, zcyto21, zcyto22, zcyto24 and zcyto25 polypeptide). Human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

A variety of assays known to those skilled in the art can be utilized to detect antibodies which specifically bind to zcyto20, zcyto21, zcyto22, zcyto24 and zcyto25 polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to zcyto20, zcyto21, zcyto22, zcyto24 and zcyto25 may be used for affinity purification of the protein, within diagnostic assays for determining circulating levels of the protein; for detecting or quantitating soluble zcyto20, zcyto21, zcyto22, zcyto24 and zcyto25 polypeptide as a marker of underlying pathology or disease; for immunolocalization within whole animals or tissue sections, including immunodiagnostic applications; for immunohistochemistry; and as antagonists to block protein activity in vitro and in vivo. Antibodies to zcyto20, zcyto21, zcyto22, zcyto24 and zcyto25 may also be used for tagging cells that express zcyto20, zcyto21, zcyto22, zcyto24 and zcyto25; for affinity purification of zcyto20, zcyto21, zcyto22, zcyto24 and zcyto25 polypeptides and proteins; in analytical methods employing FACS; for screening expression libraries; and for generating anti-idiotypic antibodies. Antibodies can be linked to other compounds, including therapeutic and diagnostic agents, using known methods to provide for targeting of those compounds to cells expressing receptors for zcyto20, zcyto21, zcyto22, zcyto24 and zcyto25. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies of the present invention may also be directly or indirectly conjugated to drugs, toxins, radionuclides and the like, and these conjugates used for in vivo diagnostic or therapeutic applications (e.g., inhibition of cell proliferation). See, in general, Ramakrishnan et al., *Cancer Res.* 56:1324-1330, 1996.

Polypeptides and proteins of the present invention can be used to identify and isolate receptors. Zcyto20, zcyto21, zcyto22, zcyto24 and zcyto25 receptors may be involved in growth regulation in the liver, blood vessel formation, and other developmental processes. For example, zcyto20, zcyto21, zcyto22, zcyto24 and zcyto25 proteins and polypeptides can be immobilized on a column, and membrane preparations run over the column (as generally disclosed in *Immobilized Affinity Ligand Techniques*, Hermanson et al., eds., Academic Press, San Diego, Calif., 1992, pp. 195-202). Proteins and polypeptides can also be radiolabeled (*Methods Enzymol., vol.* 182, "Guide to Protein Purification", M. Deutscher, ed., Academic Press, San Diego, 1990, 721-737) or photoaffinity labeled (Brunner et al., *Ann. Rev. Biochem.* 62:483-514, 1993 and Fedan et al., *Biochem. Pharmacol.* 33:1167-1180, 1984) and used to tag specific cell-surface proteins. In a similar manner, radiolabeled zcyto20 proteins and polypeptides can be used to clone the cognate receptor in binding assays using cells transfected with an expression cDNA library.

Zcyto20, zcyto21, zcyto22, zcyto24 and zcyto25 polypeptides can also be used to teach analytical skills such as mass spectrometry, circular dichroism, to determine conformation, especially of the four alpha helices, x-ray crystallography to determine the three-dimensional structure in atomic detail, nuclear magnetic resonance spectroscopy to reveal the structure of proteins in solution. For example, a kit containing the zcyto20, zcyto21, zcyto22, zcyto24 and zcyto25 can be given to the student to analyze. Since the amino acid sequence would be known by the instructor, the protein can be given to the student as a test to determine the skills or develop the skills of the student, the instructor would then know whether or not the student has correctly analyzed the polypeptide. Since every polypeptide is unique, the educational utility of zcyto20 would be unique unto itself.

The antibodies which bind specifically to zcyto20, zcyto21, zcyto22, zcyto24 and zcyto25 can be used as a teaching aid to instruct students how to prepare affinity chromatography columns to purify zcyto20, zcyto21, zcyto22, zcyto24 and zcyto25, cloning and sequencing the polynucleotide that encodes an antibody and thus as a practicum for teaching a student how to design humanized antibodies. The zcyto20, zcyto21, zcyto22, zcyto24 and zcyto25 gene, polypeptide, or antibody would then be packaged by reagent companies and sold to educational institutions so that the students gain skill in art of molecular biology. Because each gene and protein is unique, each gene and protein creates unique challenges and learning experiences for students in a lab practicum. Such educational kits containing the ZCYTO20 gene, polypeptide, or antibody are considered within the scope of the present invention.

In summary, the present invention provides an isolated polypeptide that has at least 80% or 95% or 100% identity to a polypeptide selected from the group consisting: (a) a polypeptide comprising an amino acid sequence as shown in SEQ ID NO:2 from amino acid residue 22 to amino acid residue 205; (b) a polypeptide comprising an amino acid sequence as shown in SEQ ID NO: 7 from amino acid residue 22 to amino acid residue 205; (c) a polypeptide comprising an amino acid sequence as shown in SEQ ID NO: 9 from amino acid residue 29 to amino acid residue 202; and (d) a polypeptide comprising an amino acid sequence as shown in SEQ ID NO: 11 from amino acid residue 29 to amino acid residue 202.

In another embodiment, the isolated polypeptide binds a receptor as shown in SEQ ID NOS: 24, 27 or 29 as a monomeric or homodimeric receptor or SEQ ID NOS: 24, 27 or 29 in combination with SEQ ID NO:41 as a heterodimeric receptor.

In another aspect, the present invention includes an isolated polypeptide comprising an amino acid sequence as shown in SEQ ID NO:2 from amino acid residue 22 to amino acid residue 205 or as shown in SEQ ID NO:2 from amino acid residue 1 to amino acid residue 205.

In another aspect, the present invention includes an isolated polypeptide comprising an amino acid sequence as shown in SEQ ID NO:7 from amino acid residue 22 to amino acid residue 205 or as shown in SEQ ID NO:7 from amino acid residue 1 to amino acid residue 205.

In another aspect, the present invention includes an isolated polypeptide comprising an amino acid sequence as shown in SEQ ID NO: 9 from amino acid residue 29 to amino acid residue 202 or as shown in SEQ ID NO:9 from amino acid residue 1 to amino acid residue 202.

In another aspect, the present invention includes an isolated polypeptide comprising an amino acid sequence as shown in SEQ ID NO: 11 from amino acid residue 29 to amino acid residue 202 or as shown in SEQ ID NO: 11 from amino acid residue 1 to amino acid residue 202.

In another aspect, the present invention includes an isolated polypeptide that is at least 14 contiguous amino acids of SEQ ID NO:2 from amino acid residue 22 to amino acid residue 205 or as shown in SEQ ID NO:2 from amino acid residue 1 to amino acid residue 205, wherein said polypeptide stimulates an antigenic response in a mammal.

In another aspect, the present invention includes an isolated polypeptide that is at least 14 contiguous amino acids of SEQ ID NO:7 from amino acid residue 22 to amino acid residue 205 or as shown in SEQ ID NO:7 from amino acid residue 1 to amino acid residue 205, wherein said polypeptide stimulates an antigenic response in a mammal.

In another aspect, the present invention includes an isolated polypeptide that is at least 14 contiguous amino acids of SEQ ID NO: 9 from amino acid residue 29 to amino acid residue 202 or as shown in SEQ ID NO:9 from amino acid residue 1 to amino acid residue 202, wherein said polypeptide stimulates an antigenic response in a mammal.

In another aspect, the present includes an isolated polypeptide that is at least 14 contiguous amino acids of SEQ ID NO: 11 from amino acid residue 29 to amino acid residue 202 or as shown in SEQ ID NO: 11 from amino acid residue 1 to amino acid residue 202, wherein said polypeptide stimulates an antigenic response in a mammal.

The present invention includes pharmaceutical compositions comprising the polypeptides described herein, in pharmaceutically acceptable vehicles.

The present invention also includes fusion proteins comprising the polypeptides described herein.

In other aspects, the present invention includes an isolated polynucleotide that encodes a polypeptide, wherein the nucleic acid molecule is selected from the group consisting of: (a) a polynucleotide comprising the nucleotide sequence of SEQ ID NO:3, (b) a polynucleotide that remains hybridized following stringent wash conditions to a polynucleotide consisting of the nucleotide sequence of nucleotides 64 to 618 of SEQ ID NO:1, or the complement of the nucleotide sequence of nucleotides 64 to 618 of SEQ ID NO:1.

In another embodiment, the isolated polynucleotide that encodes a polypeptide, wherein the nucleic acid molecule is selected from the group consisting of: (a) a polynucleotide comprising the nucleotide sequence of SEQ ID NO:36, (b) a polynucleotide that remains hybridized following stringent wash conditions to a polynucleotide consisting of the nucleotide sequence of nucleotides 64 to 618 of SEQ ID NO:6, or the complement of the nucleotide sequence of nucleotides 64 to 618 of SEQ ID NO:6.

In another aspect, the present invention includes an isolated polynucleotide comprising a nucleotide sequence as shown in SEQ ID NO:1 from nucleotide 64 to nucleotide 618 or as shown in SEQ ID NO:1 from nucleotide 1 to nucleotide 618.

In another embodiment, the present invention includes an isolated polynucleotide comprising a nucleotide sequence as shown in SEQ ID NO:6 from nucleotide 64 to nucleotide 618 or as shown in SEQ ID NO:6 from nucleotide 1 to nucleotide 618.

In another embodiment, the present invention includes an isolated polynucleotide comprising a nucleotide sequence as shown in SEQ ID NO:8 from nucleotide 67 to nucleotide 606 or as shown in SEQ ID NO:1 from nucleotide 1 to nucleotide 606.

In another embodiment, the present invention includes an isolated polynucleotide comprising a nucleotide sequence as shown in SEQ ID NO:10 from nucleotide 67 to nucleotide 606 or as shown in SEQ ID NO:10 from nucleotide 1 to nucleotide 606.

The present invention provides expression vectors, comprising the isolated nucleic acid molecules described herein with a transcription promoter, and a transcription terminator, wherein the promoter is operably linked with the nucleic acid molecule, and wherein the nucleic acid molecule is operably linked with the transcription terminator.

The present invention includes provides recombinant host cells comprising the expression vector described herein, wherein the host cell is selected from the group consisting of bacterium, yeast cell, fungal cell, insect cell, mammalian cell, and plant cell.

In another aspect, the present invention provides a method of producing a polypeptide, the method comprising the step of culturing recombinant host cells that comprise the expression vectors described herein, and that produce the polypeptides.

The present invention provides an antibody or antibody fragment that specifically binds with the polypeptides described herein.

In another aspect, the present invention provides a method for expansion of monocytic cells or moncyte cell progenitors comprising culturing bone marrow or peripheral blood cells with a composition comprising an amount of the polypeptides described herein sufficient to produce an increase in the number of monocytic cells or moncyte cell progenitors in the bone marrow or peripheral blood cells as compared to bone marrow or peripheral blood cells cultured in the absence of administered polypeptide.

The present invention also provides a method of stimulating an immune response in a mammal exposed to an antigen or pathogen comprising: (1) determining a level of an antigen- or pathogen-specific antibody; (2) administering a composition comprising the polypeptides described herein in an acceptable pharmaceutical vehicle; (3) determining a post administration level of antigen- or pathogen-specific antibody; (4) comparing the level of antibody in step (1) to the level of antibody in step (3), wherein an increase in antibody level is indicative of stimulating an immune response.

In other aspects, the present invention provides a method of producing an anti-viral response in a mammal comprising administering to a mammal with a viral infection an amount of a composition of the polypeptides described herein sufficient to show a reduction in virus.

The present invention, thus generally described, will be understood more readily by reference to the following examples, which is provided by way of illustration and is not intended to be limiting of the present invention.

EXAMPLES

Example 1

Mammalian Expression Plasmids

An expression plasmid containing a polynucleotide encoding zcyto20, zcyto21, zcyto22, zcyto24 or zcyto25 can be constructed via homologous recombination. A fragment of cDNA, for example zcyto20 cDNA, is isolated by PCR using the polynucleotide sequence of SEQ ID NO: 1 with flanking regions at the 5' and 3' ends corresponding to the vector sequences flanking the zcyto20 insertion point. The primers ZC40923 and ZC40927 are shown in SEQ ID NOS: 12 and 13, respectively.

The PCR reaction mixture is run on a 1% agarose gel and a band corresponding to the size of the insert is gel-extracted using a QIAQUICK® Gel Extraction Kit (Qiagen, Valencia, Calif.). Plasmid pZMP21 is a mammalian expression vector containing an expression cassette having the MPSV promoter, multiple restriction sites for insertion of coding sequences, a stop codon, an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It is constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. Plasmid pZMP21 was digested with BglII, and used for recombination with the PCR insert.

One hundred microliters of competent yeast (*S. cerevisiae*) cells are independently combined with 10 µl of the various DNA mixtures from above and transferred to a 0.2-cm electroporation cuvette. The yeast/DNA mixtures are electropulsed using power supply (BioRad Laboratories, Hercules, Calif.) settings of 0.75 kV (5 kV/em), ∞ ohms, 25 µF. To each cuvette is added 600 µl of 1.2 M sorbitol, and the yeast is plated in two 300-µl aliquots onto two URA-D plates and incubated at 30° C. After about 48 hours, the Ura+ yeast transformants from a single plate are resuspended in 1 ml $H_2O$ and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid-washed glass beads and 200 µl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 µl ethanol (EtOH), followed by centrifugation for 10 minutes at 4° C. The DNA pellet is resuspended in 10 µl $H_2O$.

Transformation of electrocompetent *E. coli* host cells (ELECTROMAX® DH10B™ cells; obtained from Life Technologies, Inc., Gaithersburg, Md.) is done with 0.5-2 ml yeast DNA prep and 40 µl of cells. The cells are electropulsed at 1.7 kV, 25 µF, and 400 ohms. Following electroporation, 1 ml SOC (2% BACTO® Tryptone (Difco, Detroit, Mich.), 0.5% yeast extract (Difco), 10 mM NaCl, 2.5 mM KCl, 10 mM $MgCl_2$, 10 in M $MgSO_4$, 20 mM glucose) is plated in 250-µl aliquots on four LB AMP plates (LB broth (Lennox), 1.8% BACTO® Agar (Difco), 100 mg/L Ampicillin).

Individual clones harboring the correct expression construct for zcyto20 are identified by restriction digest to verify the presence of the zcyto20 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated zcyto20-CEE/pZMP21.

Plasmids containing zcyto21, zcyto22, zcyto24 or zcyto25 are prepared similarly, using nucleotide-specific primers Example 2

Expression in Chinese Hamster Ovary Cells

CHO DG44 cells (Chasin et al., *Som. Cell. Molec. Genet.* 12:555-666, 1986) are plated in 10-cm tissue culture dishes and allowed to grow to approximately 50% to 70% confluency overnight at 37° C., 5% $CO_2$, in Ham's F12/FBS media (Ham's F12 medium (Life Technologies), 5% fetal bovine serum (Hyclone, Logan, Utah), 1% L-glutamine (JRH Biosciences, Lenexa, Kans.), 1% sodium pyruvate (Life Technologies)). The cells are then transfected with a plasmid containing zcyto20, zcyto21, zcyto22, zcyto24 or zcyto25, i.e. zcyto20/pZMP6, by liposome-mediated transfection using a 3:1 (w/w) liposome formulation of the polycationic lipid 2,3-dioleyloxy-N-[2(sperminecarboxamido)ethyl]-N,N-dimethyl-1-propaniminium-trifluoroacetate and the neutral lipid dioleoyl phosphatidylethanolamine in membrane-filtered water (LIPOFECTAMINE® Reagent, Life Technologies), in serum free (SF) media formulation (Ham's F12, 10 mg/ml transferrin, 5 mg/ml insulin, 2 mg/ml fetuin, 1% L-glutamine and 1% sodium pyruvate). Zcyto20/pZMP6 is diluted into 15-ml tubes to a total final volume of 640 µl with SF media. 35 µl of Lipofectamine™ is mixed with 605 µl of SF medium. The resulting mixture is added to the DNA mixture and allowed to incubate approximately 30 minutes at room temperature. Five ml of SF media is added to the DNA: LIPOFECTAMINE® mixture. The cells are rinsed once with 5 ml of SF media, aspirated, and the DNA:LIPOFECTAMINE® mixture is added. The cells are incubated at 37° C. for five hours, then 6.4 ml of Ham's F12/10% FBS, 1% PSN media is added to each plate. The plates are incubated at 37° C. overnight, and the DNA:LIPOFECTAMINE® mixture is replaced with fresh 5% FBS/Ham's media the next day. On day 3 post-transfection, the cells are split into T-175 flasks in growth medium. On day 7 posttransfection, the cells are stained with FITC-anti-CD8 monoclonal antibody (Pharmingen, San Diego, Calif.) followed by anti-FITC-conjugated magnetic beads (Miltenyi Biotec, Auburn, Calif.). The CD8-positive cells are separated using commercially available columns (mini-MACS columns; Miltenyi Biotec) according to the manufacturer's directions and put into DMEM/Ham's F12/5% FBS without nucleosides but with 50 nM methotrexate (selection medium).

Cells are plated for subcloning at a density of 0.5, 1 and 5 cells per well in 96-well dishes in selection medium and allowed to grow out for approximately two weeks. The wells are checked for evaporation of medium and brought back to 200 µl per well as necessary during this process. When a large percentage of the colonies in the plate are near confluency, 100 µl of medium is collected from each well for analysis by dot blot, and the cells are fed with fresh selection medium. The supernatant is applied to a nitrocellulose filter in a dot blot apparatus, and the filter is treated at 100° C. in a vacuum oven to denature the protein. The filter is incubated in 625 mM Tris-glycine, pH 9.1, 5 mM β-mercaptoethanol, at 65° C., 10 minutes, then in 2.5% non-fat dry milk Western A Buffer (0.25% gelatin, 50 mM Tris-HCl pH 7.4, 150 mM NaCl, 5 mM EDTA, 0.05% Igepal CA-630) overnight at 4° C. on a rotating shaker. The filter is incubated with the antibody-HRP conjugate in 2.5% non-fat dry milk Western A buffer for 1 hour at room temperature on a rotating shaker. The filter is then washed three times at room temperature in PBS plus 0.01% Tween 20, 15 minutes per wash. The filter is developed with chemiluminescence reagents (ECL™ direct labelling kit; Amersham Corp., Arlington Heights, Ill.) according to the manufacturer's directions and exposed to film (Hyperfilm ECL, Amersham Corp.) for approximately 5 minutes. Positive clones are trypsinized from the 96-well dish and transferred to 6-well dishes in selection medium for scaleup and analysis by Western blot.

Example 3

Expression in Baby Hamster Kidney Cells

The full-length zcyto24 and zcyto25 proteins were produced in BHK cells. For example, the BHK cells were transfected with either zcyto24-CEE/pZMP21 or zcyto25-CEE/pZMP21 (Example 1). BHK 570 cells (ATCC CRL-10314) were plated in T75 tissue culture flasks and allowed to grow to approximately 50 to 70% confluence overnight at 37° C., 5% $CO_2$, in growth medium (SL7V4, 5% fetal bovine serum (Hyclone, Logan, Utah), 1% penicillin/strepomycin). The cells were then transfected with zcyto24-CEE/pZMP21 or zcyto25-CEE/pZMP21 by liposome-mediated transfection (using LIPOFECTAMINE®; Life Technologies), in serum free (SF) media. The plasmid was diluted into 1.5-ml tubes to a total final volume of 640 µl with SF media. Thirty-five µl of the lipid mixture was mixed with 605 µl of SF medium, and the resulting mixture is allowed to incubate approximately 30 minutes at room temperature. Six ml of SF media was then added to the DNA/lipid mixture. The cells were rinsed once with 5 ml of SF media, aspirated, and the DNA/lipid mixture was added. The cells are incubated at 37° C. for five hours, then 15 ml of growth medium was added to each plate. The plates were incubated at 37° C. overnight, and the DNA/lipid mixture was replaced with selection medium (SL7V4, 5% fetal bovine serum (Hyclone, Logan, Utah), 1% penicillin/strepomycin, 1 µM MTX) the next day. Approximately 7-10 days post-transfection, methotrexate-resistant colonies were trypsinized, and the cells were re-plated into T-162 flasks and transferred to large-scale culture.

Example 4

Construction of Adenovirus Vectors

For construction of adenovirus vectors, the protein coding region of zcyto20, zcyto21, zcyto22, zcyto24 or zcyto25 is amplified by PCR using primers that add PmeI and AscI restriction sites at the 5' and 3' termini respectively. Amplification is performed with a full-length cDNA template in a PCR reaction as follows: one cycle at 95° C. for 5 minutes; followed by 15 cycles at 95° C. for 1 min., 61° C. for 1 min., and 72° C. for 1.5 min.; followed by 72° C. for 7 min.; followed by a 4° C. soak. The PCR reaction product is loaded onto a 1.2% low-melting-temperature agarose gel in TAE buffer (0.04 M Tris-acetate, 0.001 M EDTA). The PCR product is excised from the gel and purified using a commercially available kit comprising a silica gel membrane spin column (QIAQUICK® PCR Purification Kit and gel cleanup kit; Qiagen, Inc.) as per kit instructions. The PCR product is then digested with PmeI and AscI, phenol/chloroform extracted, EtOH precipitated, and rehydrated in 20 ml TE (Tris/EDTA pH 8). The zcyto20 fragment is then ligated into the PmeI-AscI sites of the transgenic vector pTG12-8 and transformed into *E. coli* DH10B™ competent cells by electroporation. Vector pTG12-8 was derived from p2999B4 (Palmiter et al., *Mol. Cell. Biol.* 13:5266-5275, 1993) by insertion of a rat insulin II intron (ca. 200 bp) and polylinker (Fse I/Pme I/Asc I) into the Nru I site. The vector comprises a mouse metallothionein (MT-1) promoter (ca. 750 bp) and human growth hormone (hGH) untranslated region and polyadenylation signal (ca. 650 bp) flanked by 10 kb of MT-1 5' flanking sequence and 7 kb of MT-1 3' flanking sequence. The cDNA is inserted between the insulin II and hGH sequences. Clones containing the zcyto20, zcyto21, zcyto22, zcyto24 or zcyto25 cDNA are identified by plasmid DNA miniprep followed by digestion with PmeI and AscI. Positive clones are sequenced to insure that there were no deletions or other anomalies in the construct.

DNA is prepared using a commercially available kit (Maxi Kit, Qiagen, Inc.), and the cDNA is released from the pTG12-8 vector using PmeI and AscI enzymes. The cDNA is isolated on a 1% low melting temperature agarose gel and excised from the gel. The gel slice is melted at 70° C., and the DNA is extracted twice with an equal volume of Tris-buffered phenol, precipitated with EtOH, and resuspended in 10 µl $H_2O$.

The cDNA is cloned into the EcoRV-AscI sites of a modified pAdTrack-CMV (He, T-C. et al., *Proc. Natl. Acad. Sci. USA* 95:2509-2514, 1998). This construct contains the green fluorescent protein (GFP) marker gene. The CMV promoter driving GFP expression is replaced with the SV40 promoter, and the SV40 polyadenylation signal is replaced with the human growth hormone polyadenylation signal. In addition, the native polylinker is replaced with FseI, EcoRV, and AscI sites. This modified form of pAdTrack-CMV is named pZyTrack. Ligation is performed using a commercially available DNA ligation and screening kit (Fast-Link® kit; Epicentre Technologies, Madison, Wis.). Clones containing zcyto20 are identified by digestion of mini prep DNA with FseI and AscI. In order to linearize the plasmid, approximately 5 µg of the resulting pZyTrack zcyto20, zcyto21, zcyto22, zcyto24 or zcyto25 plasmid is digested with PmeI. Approximately 1 µg of the linearized plasmid is cotransformed with 200 ng of supercoiled pAdEasy (He et al., ibid.) into *E. coli* BJ5183 cells (He et al., ibid.). The co-transformation is done using a Bio-Rad Gene Pulser at 2.5 kV, 200 ohms and 25 µFa. The entire co-transformation mixture is plated on 4 LB plates containing 25 µg/ml kanamycin. The smallest colonies are picked and expanded in LB/kanamycin, and recombinant adenovirus DNA is identified by standard DNA miniprep procedures. The recombinant adenovirus miniprep DNA is transformed into *E. coli* DH10B™ competent cells, and DNA is prepared using a Maxi Kit (Qiagen, Inc.) according to kit instructions.

Approximately 5 µg of recombinant adenoviral DNA is digested with PacI enzyme (New England Biolabs) for 3 hours at 37° C. in a reaction volume of 100 µl containing 20-30 U of PacI. The digested DNA is extracted twice with an equal volume of phenol/chloroform and precipitated with ethanol. The DNA pellet is resuspended in 10 µl distilled water. A T25 flask of QBI-293A cells (Quantum Biotechnologies, Inc. Montreal, Qc. Canada), inoculated the day before and grown to 60-70% confluence, is transfected with the PacI digested DNA. The PacI-digested DNA is diluted up to a total volume of 50 µl with sterile HBS (150 mM NaCl, 20 mM HEPES). In a separate tube, 20 µl of 1 mg/ml N-[1-(2,3-Dioleoyloxy) propyl]-N,N,N-trimethyl-ammonium salts (DOTAP) (Boehringer Mannheim, Indianapolis, Ind.) is diluted to a total volume of 100 µl with FIBS. The DNA is added to the DOTAP, mixed gently by pipeting up and down, and left at room temperature for 15 minutes. The media is removed from the 293A cells and washed with 5 ml serum-free minimum essential medium (MEM) alpha containing 1 mM sodium pyruvate, 0.1 mM MEM non-essential amino acids, and 25 mM HEPES buffer (reagents obtained from Life Technologies, Gaithersburg, Md.). Five ml of serum-free MEM is added to the 293A cells and held at 37° C. The DNA/lipid mixture is added drop-wise to the T25 flask of 293A cells, mixed gently, and incubated at 37° C. for 4 hours. After 4 hours the media containing the DNA/lipid mixture is aspirated off and replaced with 5 ml complete MEM containing 5% fetal bovine serum. The transfected cells are monitored for GFP expression and formation of foci (viral plaques).

Seven days after transfection of 293A cells with the recombinant adenoviral DNA, the cells express the GFP protein and start to form foci (viral "plaques"). The crude viral lysate is collected using a cell scraper to collect all of the 293A cells. The lysate is transferred to a 50-ml conical tube. To release most of the virus particles from the cells, three freeze/thaw cycles are done in a dry ice/ethanol bath and a 37° C. waterbath.

The crude lysate is amplified (Primary (1°) amplification) to obtain a working "stock" of zcyto20 rAdV lysate. Ten 10 cm plates of nearly confluent (80-90%) 293A cells are set up 20 hours previously, 200 ml of crude rAdV lysate is added to each 10-cm plate, and the cells are monitored for 48 to 72 hours for CPE (cytopathic effect) under the white light microscope and expression of GFP under the fluorescent microscope. When all of the 293A cells show CPE, this stock lysate is collected and freeze/thaw cycles performed as described above.

A secondary (2°) amplification of zcyto20 rAdV is then performed. Twenty 15-cm tissue culture dishes of 293A cells are prepared so that the cells are 80-90% confluent. All but 20 ml of 5% MEM media is removed, and each dish is inoculated with 300-500 ml of the 1° amplified rAdv lysate. After 48 hours the 293A cells are lysed from virus production, the lysate is collected into 250-ml polypropylene centrifuge bottles, and the rAdV is purified.

NP-40 detergent is added to a final concentration of 0.5% to the bottles of crude lysate in order to lyse all cells. Bottles are placed on a rotating platform for 10 minutes agitating as fast as possible without the bottles falling over. The debris is pelleted by centrifugation at 20,000×G for 15 minutes. The supernatant is transferred to 250-ml polycarbonate centrifuge bottles, and 0.5 volume of 20% PEG8000/2.5 M NaCl solution is added. The bottles are shaken overnight on ice. The bottles are centrifuged at 20,000×G for 15 minutes, and the supernatant is discarded into a bleach solution. Using a sterile cell scraper, the white, virus/PEG precipitate from 2 bottles is resuspended in 2.5 ml PBS. The resulting virus solution is placed in 2-ml microcentrifuge tubes and centrifuged at 14,000×G in the microcentrifuge for 10 minutes to remove any additional cell debris. The supernatant from the 2-ml microcentrifuge tubes is transferred into a 15-ml polypropylene snapcap tube and adjusted to a density of 1.34 g/ml with CsCl. The solution is transferred to 3.2-ml, polycarbonate, thick-walled centrifuge tubes and spun at 348,000×G for 3-4 hours at 25 µC. The virus forms a white band. Using widebore pipette tips, the virus band is collected.

A commercially available ion-exchange column (e.g., PD-10 columns prepacked with SEPHADEX® G-25M; Pharmacia Biotech, Piscataway, N.J.) is used to desalt the virus preparation. The column is equilibrated with 20 ml of PBS. The virus is loaded and allowed to run into the column. 5 ml of PBS is added to the column, and fractions of 8-10 drops are collected. The optical densities of 1:50 dilutions of each fraction are determined at 260 nm on a spectrophotometer. Peak fractions are pooled, and the optical density (OD) of a 1:25 dilution is determined. OD is converted to virus concentration using the formula: (OD at 260 nm)(25)(1.1× $10^{12}$)=virions/ml.

To store the virus, glycerol is added to the purified virus to a final concentration of 15%, mixed gently but effectively, and stored in aliquots at −80 µC.

A protocol developed by Quantum Biotechnologies, Inc. (Montreal, Canada) is followed to measure recombinant virus infectivity. Briefly, two 96-well tissue culture plates are seeded with $1\times10^4$ 293A cells per well in MEM containing 2% fetal bovine serum for each recombinant virus to be assayed. After 24 hours 10-fold dilutions of each virus from $1\times10^{-2}$ to $1\times10^{-14}$ are made in MEM containing 2% fetal bovine serum. 100 µl of each dilution is placed in each of 20 wells. After 5 days at 37° C., wells are read either positive or negative for CPE, and a value for "Plaque Forming Units/ml" (PFU) is calculated.

Example 5

Cloning of Zcyto20, Zcyto22, Zcyto24, And Zcyto25

A: Zcyto20 and Zcyto22

PCR primers were designed that were common to both zcyto20 and zcyto22 within the predicted coding sequence. These are designated ZC39339 (SEQ ID NO:47) and ZC39393 (SEQ ID NO:48). PCR was carried out on a panel of human cDNA libraries from different tissues. The product was observed in brain, islet (pancreas), prostate, placenta, testis, HPVS(prostate epithelia), and CD3+ libraries. PCR primers were then designed from the genomic sequence 5' of the starting methionine and 3' of the termination codon for zcyto20 (with high similarity to zcyto22). These were designated ZC39340 (SEQ ID NO:49) and ZC39341 (SEQ ID NO:50). PCR was carried out on the previously identified libraries. Four libraries contained full length clones. Sequencing of PCR products generated from these libraries resulted in three libraries containing zcyto22 (prostate, testis and CD3+), and one library containing zcyto20 (HPVS (prostate epithelia)). PCR using primers specific to the predicted coding sequence of zcyto22 was also carried out. These are designated ZC39295 (SEQ ID NO:51) and ZC39298 (SEQ ID NO:52) Libraries positive by this PCR were brain, prostate, CD3+, and testis. Sequencing confirmed the zcyto22 sequence.

B: Zcyto24 and Zcyto25

PCR primers were designed that were common to both zcyto24 and zcyto25 within the predicted coding sequence. These are designated ZC39687 (SEQ ID NO:53) and ZC39741 (SEQ ID NO:54). PCR was carried out on a panel of mouse cDNA libraries from different tissues. The product was observed in the following libraries: heart, lung, placenta, Torres prostate, skin, small intestine, testis, and thymus. PCR primers were then designed 5' of the starting methionine and at the termination codons. The 5' primer is designated ZC39732 (SEQ ID NO:55) and matches both zcyto24 ands zcyto25 sequences. The zcyto24 3' primer is designated ZC39701 (SEQ ID NO:56). The zcyto25 3' primer is designated ZC39688 (SEQ ID NO:57). PCR was carried out on the positive libraries indicated above. For zcyto24, all libraries except heart and Torres prostate were positive. Sequencing confirmed zcyto24 sequence from placenta, testis, and small intestine libraries. For zcyto25, all libraries except heart and Torres prostate were positive. Sequencing confirmed zcyto25 sequence from the Jung library.

Example 6

Expression in Baculovirus

A: Construct for Expression of Zcyto20

An expression vector, pzBV37L:zCyto20, was prepared to express zcyto20 polypeptides in insect cells. A 536 bp fragment containing sequence for zcyto20 and encoded B spE1 and Xba1 restriction sites on the 5' and 3' ends, respectively, was generated by PCR amplification from a plasmid zcyto20 using primers ZC41932 (SEQ ID NO:14) and ZC41933 (SEQ ID NO:15) utilizing the Expand High Fidelity PCR System (Boerhinger Mannheim) as per manufacturer's instructions. The PCR conditions were as follows: 1 cycle of 94° C. for 4 minutes, 30 cycles of 94° C. for 30 seconds, 50° C. for 30 seconds, and 72° C. for 1 minute; 1 cycle at 72° C. for 4 min; followed by a 4° C. soak. A small portion of the PCR product was visualized by gel electrophoresis (1% NuSieve agarose), and a fragment length of approximately 550 bp was confirmed. The remainder of the reaction mix was purified via the Qiagen PCR purification kit as per manufacturer's instructions and eluted in 30 µl water. The cDNA was digested in a 36 µl vol. using Bspe1 and Xba1 (New England Biolabs, Beverly, Mass.) in appropriate buffer conditions at 37° C. The digested PCR product band was run through a 1% agarose TAE gel, excised and extracted using a QIAQUICK® Gel Extraction Kit (Qiagen, Cat. No. 28704) and eluted in 30 µl of EB buffer. The digested zcyto20 PCR product was ligated into the multiple cloning site (MCS) of vector pZBV37L at the Bspe1 and Xba1 sites. The pZBV37L vector is a modification of the pFastBac1™ (Life Technologies) expression vector, where the polyhedron promoter has been removed and replaced with the late activating Basic Protein Promoter and the EGT leader signal sequence upstream of the MCS. 5 µl of the restriction enzyme digested zcyto20 PCR fragment and 4 µl of the corresponding pZBV37L vector were ligated for 72 hours at 15° C. in a 20 µl vol. in appropriate buffer conditions. 5 µl of the ligation mix was transformed into 33 µl of ELECTROMAX® DH12s™ cells (Life Technologies, Cat. No. 18312-017) by electroporation at 400 Ohms, 2.00 kV and 25 µF in a 2 mm gap electroporation cuvette (BTX, Model No. 620). The transformed cells were diluted in 500 µl of LB media and outgrown for 1 hr at 37° C. and 10 µl and 20 µl of the dilution were plated onto LB plates containing 100 µg/ml ampicillin. Clones were analyzed by PCR and positive clones were selected, plated, and submitted for sequencing. The sequence was then confirmed.

B. Construction and Expression of Tagged zcyto20

An expression vector, pZBV32L:zCyto20cee, was prepared to express zcyto20cee polypeptides in insect cells. PZBV32L:zCyto20cee was designed to express a zcyto20 polypeptide with a C-terminal GLU-GLU tag (SEQ ID NO:16). This, construct can be used to determine the N-terminal amino acid sequence of zcyto20 after the signal peptide has been cleaved off.

1. Construction of pZBV32L:zCyto20cee

A 625 bp zcyto20 fragment containing BamHI and XbaI restriction sites on the 5' and 3' ends, respectively, was generated by PCR amplification from a plasmid containing zcyto20 cDNA using primers zc40240 and zc40241 (SEQ ID NOS: 17 and 18, respectively). The PCR reaction conditions were as follows: The Expand High Fidelity PCR System (Boehringer Mannheim) was utilized for a 100 µl volume reaction containing 5% DMSO. 1 cycle at 94° C. for 4 minutes; 30 cycles of 94° C. for 30 seconds, 50° C. for 30 seconds, and 72° C. for 60 seconds; 1 cycle at 72° C. for 4 min; followed by 4° C. soak. Five µl of the PCR fragment was visualized by gel electrophoresis (1% NuSieve agarose). The remainder of the reaction mix was purified via Qiagen PCR purification kit as per manufacturer's instructions and eluted in 30 µl water. The cDNA was digested in a 35 µl volume using BamHI and XbaI (New England Biolabs, Beverly, Mass.) in appropriate buffer conditions for 2 hrs at 37° C. The digested PCR product band was run through a 1% agarose TAE gel, excised and extracted using a QIAQUICK® Gel Extraction Kit (Qiagen) and eluted in 30 µl of water. The purified, digested zCyto20cee PCR product was ligated into the multiple cloning site of a previously prepared and restriction enzyme digested (BamHI and XbaI) vector pZBV32L. The pZBV32L vector is a modification of the pFastBac1™ (Life Technologies) expression vector, where the polyhedron promoter has been removed and replaced with the late activating Basic Protein Promoter, and the coding sequence for the Glu-Glu tag (SEQ ID NO:10) as well as a stop signal was inserted at the 3' end of the multiple cloning region. Five µl of the restriction digested zCyto20 insert and 40 ng of the corresponding pZBV32L vector were ligated overnight at 16° C. in a 20 µl vol. Five µl of the ligation mix was transformed into 50 µl of ELECTROMAX® DH12s™ cells (Life Technologies) by electroporation at 400 Ohms, 2.00 kV and 25 µF in a 2 mm gap electroporation cuvette. The transformed cells were diluted in 500 µl of SOC media (2% BACTO® Tryptone, 0.5% BACTO® Yeast Extract, 10 ml 1M NaCl, 1.5 mM KCl, 10 mM $MgCl_2$, 10 mM $MgSO_4$ and 20 mM glucose) and 50 µl of the dilution were plated onto LB plates containing 100 µg/ml ampicillin. Clones were analyzed by PCR and restriction digestion. Positive clones were selected and plated for sequencing. Once proper sequence was confirmed, 25 ng of positive clone DNA was transformed into 66 µl DH10Bac™ MAX EFFICIENCY® competent cells (GIBCO-BRL) by heat shock for 45 seconds in a 42° C. heat block. The transformed DH10Bac™ cells were diluted in 600 µl SOC media (2% BACTO® Tryptone, 0.5% Bacto Yeast Extract, 10 ml 1M NaCl, 1.5 mM KCl, 10 mM $MgCl_2$, 10 mM $MgSO_4$ and 20 mM glucose) and grown at 37° C. for 1 hr and 100 µl were plated onto Luria Agar plates containing 50 µg/ml kanamycin, 7 µg/ml gentamicin, 10 µg/ml tetracycline, 40 µg/mL WIG and 200 µg/mL Bluo Gal. The plates were incubated for 48 hours at 37° C. A color selection was used to identify those cells having transposed viral DNA (referred to as a "bacmid"). Those colonies, which were white in color, were picked for analysis. Colonies were analyzed by PCR and positive colonies (containing desired bacmid) were selected for growth and subsequent bacmid DNA purification. Clones were screened for the correct molecular weight insert by PCR amplification of DNA using primers to the transposable element in the bacmid: ZC447 (SEQ ID NO:19) and ZC976 (SEQ ID NO:20). The PCR reaction conditions were as follows: 1 cycle at 94° C. for 4 minutes; 25 cycles of 94° C. for 30 seconds, 50° C. for 30 seconds, and 72° C. for 2.5 min; 1 cycle at 72° C. for 4 min; followed by 4° C. soak. The PCR product was run on a 1% agarose gel to confirm the insert size. Those having the correct size insert were used to transfect *Spodoptera Frugiperda* (Sf9) cells.

2. Transfection

Sf9 cells were seeded at $1 \times 10^6$ cells per well in a 6-well plate and allowed to attach for 1 hour at 27° C. Approximately 5 mg of bacmid DNA were diluted to 100 µl with Sf-900 II SFM (Life Technologies). Twenty µl of LIPOFECTAMINE® Reagent (Life Technologies) were diluted to 100 µl with Sf-900 H SFM. The bacmid DNA and lipid solutions were gently mixed and incubated for 45 minutes at room temperature. Eight hundred µl of Sf-900 II SFM was added to the lipid-DNA mixture. The media was aspirated from the well and the 1 ml of DNA-lipid mix added to the cells. The cells were incubated at 27° C. overnight. The DNA-lipid mix was aspirated from each well and was replaced with 2 ml of Sf-900 II media. The plates were incubated at 27° C., 90% humidity, for approximately 7 days after which the virus was harvested.

3. Amplification

Sf9 cells were seeded at $1 \times 10^6$ cells per well in a 6-well plate. Five hundred µl of virus from the transfection plate were placed in the well and the plate was incubated at 27° C., 90% humidity, for 96 hours after which the virus was harvested (primary amplification).

The second round of amplification was carried out by transferring 100 µl of virus from the above primary amplification plate to wells containing $1 \times 10^6$ cells per well. The plate was incubated for 96 hours before harvesting.

An additional round of amplification was performed (tertiary amp.) Sf9 cells were grown in 50 ml Sf-900 II SFM in a 250 ml shake flask to an approximate density of $1 \times 10^6$ cells/ml. They were then infected with 1 ml of the viral stock from the above plate and incubated at 27° C. for 6 days after which time the virus was harvested.

The viral stock was titered by a growth inhibition curve and the titer culture that indicated a Multiplicity Of Infection (MOI) of one was allowed to proceed for a total of 48 hrs. The supernatant was analyzed via a reduced Western using a primary monoclonal antibody specific for the Glu-Glu tag followed by an HRP-conjugated goat anti-murine secondary antibody. Results indicated a band of approximately 20 kDa. Supernatant was also provided for activity analysis.

A large viral stock was then generated by the following method: Sf9 cells were grown in 1 L Sf-900 II SEM in a 2800 ml shake flask to an approximate density of $1 \times 10^6$ cells/ml. They were then infected with 5 ml of the viral stock from the above flask and incubated at 27° C. for 4 days after which time the virus was harvested.

Larger scale infections were completed to provide material for downstream purification.

Similarly, zcyto21 and zcyto22 were expressed in Baculovirus

Example 7

Purification of Protein

Recombinant protein can be made for any of the protein described herein.

A. Purification of Zcyto20

Recombinant carboxyl terminal Glu-Glu tagged zcyto20 was produced from either recombinant baculovirus infected insect cells, stable or transient BHK cell lines. Cultures were harvested, and the media were sterile filtered using a 0.2 □m filter.

Proteins were purified from the conditioned media by a combination of Anti-Glu-Glu (Anti-EE) peptide antibody affinity chromatography and Superdex 75 gel exclusion chromatography. Culture medium from BV (pH 6.0, conductivity 7 mS) was adjusted to pH 6.7. Both BV and BHK media were then added NaCl to 300 mM before loading onto a 10×70 mm (5-ml column volume) Poros Protein A anti-FE antibody affinity column at a flow of 2-5 ml/minute. The column was then washed with five column volumes (CV) of 5×PBS (pH 7.2). Bound protein was eluted with 0.5 M acetic acid, 0.5 M NaCl, pH 3.0. Two-ml fractions were collected, and the eluant was neutralized by the addition of 2 M Tris. Samples from the anti-EE antibody affinity column were analyzed by SDS-PAGE with silver staining and western blotting for the presence of zcyto20 protein. Zcyto20 protein-containing fractions were pooled and concentrated to about 2 mls using Biomax-5 concentrator (Millipore), and loaded onto a 16×600 mm Superdex 75 gel filtration column (Amersham Pharmacia Biotech). The fractions containing purified zcyto20 protein were pooled, filtered through 0.2 µm filter, aliquoted into 100 µl each, and frozen at −80° C. The concentration of the final purified protein was determined by BCA assay (Pierce, Rockford, Ill.) and HPLC-amino acid analysis.

B. SDS-Page and Western Blotting Analysis of Zcyto20 Proteins

Recombinant zcyto20 protein was analyzed by SDS-PAGE (Nupage 4-12% Bis-Tris, Invitrogen, Calsbad, Calif.) with silver staining method (Fast Silver, Geno Technology, Inc., St. Louis, Mo.) and Western blotting using the anti-EE antibody. Either the conditioned media or purified protein was electrophoresed using an Xcell II™ MINI-CELL (Invitrogen, Calsbad, Calif.) and transferred to nitrocellulose (0.2 □m; Bio-Rad Laboratories, Hercules, Calif.) at room temperature using Xcell II™ blot module (Invitrogen) with stirring according to directions provided in the instrument manual. The transfer was run at 500 mA for 45 minutes in a buffer containing 25 mM Tris base, 200 mM glycine, and 20% methanol. The filters were then blocked with 10% non-fat dry milk in PBS for 10 minutes at room temperature. The nitrocellulose was quickly rinsed, and then primary antibody was added in PBS containing 2.5% non-fat dry milk. The blots were incubated for two hours at room temperature or overnight at 4° C. with gentle shaking. Following the incubation, blots were washed three times for 10 minutes each in PBS. Secondary antibody (rabbit anti-mouse IgG conjugated to horseradish peroxidase; obtained from Pierce Chemical Co., Rockford, Ill.) diluted 1:2000 in PBS containing 2.5% non-fat dry milk was added, and the blots were incubated for two hours at room temperature with gentle shaking. The blots were then washed three times, 10 minutes each, in PBS, then quickly rinsed in $H_2O$. The blots were developed using commercially available chemiluminescent substrate reagents (SuperSignal® ULTRA reagents 1 and 2 mixed 1:1; reagents obtained from Pierce Chemical Co.), and the signal was captured using Lumi-Imager's Lumi Analyst 3.0 software (Boehringer Mannheim GmbH, Germany) for times ranging from 10 second to 5 minutes or as necessary.

C. Summary of Protein Purification and Analysis

The purified zcyto20-CEE protein from BV media migrated as a 21 kDa monomer on the 4-12% Bis-Tris gel, however, a minor 36 kDa dimer band was also observed. The dimer protein became monomer band upon reduction using reducing agent, suggesting the dimerization of zcyto20-CEE by disulfide bond, and it is consistent with the odd number (a total of seven) of cysteine residues resulting in interchain disulfide bond.

Zcyto21, zcyto22, zcyto24, and zcyto25 polypeptides were purified in a similar manner.

Example 8

Interferon-like Transcriptional Regulatory Regions of zcyto20

Local sequence alignments of the characterized IFN-α, IFN-β, IFN-γ promoters and those of a number of other cytokines with the upstream regions of zcyto20, zcyto21, and zcyto24 were performed to identify whether these genes were co-regulated. The hypothesis was that common properties of gene regulation should be reflected in sequence similarities of the regions upstream of the genes.

Due to the low binding specificity of TFs, predictions of individual binding sites have a high rate of false positives. Therefore, the site predictions in isolation for the identification of binding sites with functional roles in vivo are not useful. However, predicted binding sites likely to have sequence-specific functions can be selected by means of a conservation-based filter: The biological observation that regulatory regions are often more strongly conserved between species than other non-coding regions can be quantified to reveal patterns of conservation which have been called phylogenetic footprints (Fickett, et al., Curr. Opin. Biotechnol. 11: 19-24, 2000.) In particular, human-rodent comparisons have proven a valuable resource for the identification of functional regulatory elements (Wasserman et al., Nat. Genet. 26: 225-228, 2000).

The alignments revealed significant matches mainly among the promoters of the various IFN-α genes, whereas, based on this analysis, there is little evidence for similarity between the promoters of zcyto20-22 and other cytokines.

The pairwise sequence alignments were performed with DBA (Jareborg et al., Genome. Res. 9: 815-824, 1999). The search for individual transcription factor binding sites was performed with standard position weight matrices (Fickett, Mol. Cell. Biol. 16:437-441, 1996) drawn from the TRANSFAC database (version 3.0, Wingender et al., Nucleic Acids Res. 28: 316-319, 2000), and alignments of regions 1-4 were computed with SSEARCH, version 3.1t12 (Pearson, Genomics 11:635-650, 1991). Based on published studies involving other sets of TFs, most natural binding sites sufficiently conserved between mouse and human can be expected to be detected in the used score range (Fickett, Mol. Cell. Biol. 16: 437-4411996; Wasserman et al., J. Mol. Biol. 278: 167-181, 1998).

The computational results suggest that features common to the regulation of the zcyto20 family and other cytokines that reflected by sequence similarity would be expected on the level of individual binding sites rather than matches covering extended regions.

Based on a search of binding sites of a set of 32 TFs, the identification of putative sites of a limited number of factors largely known to be involved in the transcriptional regulation of interferons were made. The results of the comparison show putative binding sites of TFs playing important roles in the transcriptional regulation of IFN-β[NF-κB, ISRE (element binding IRFs)] and IFN-γ (AP-1, CREB, GATA, NF-κB, NF-AT) are also present in the conserved non-coding regions. For example, a pair of neighboring AP-1/NF-AT sites in region 1, is a well-documented example of cooperative binding occurring in many cytokine promoters (Holloway et al., Mol. Immunol. 38: 567-580, 2000).

The binding sites for TFs that have been identified as critical for cytokine regulation, suggest that the cluster of transcription factor binding sites in the promoter region of zcyto20 is a candidate for a functional region.

The alignment of region 2 with the group of known cytokines yielded a match in the AK155 promoter, at position −415 with respect to the transcription start site of AK155 as given in Knappe et al. (J. Virol. 74: 3881-3887, 2000). The fact that there is a putative NF-κB binding site at that location in the zcyto20 promoter indicates the possible presence of a NF-κB site in the AK155 promoter.

Example 9

Transgenic Animals

Transgenic animals expressing Zcyto21 genes were produced using adult, fertile males (studs) (B6C3f1, 2-8 months of age (Taconic Farms, Germantown, N.Y.)), vasectomized males (duds) (CD1, 2-8 months, (Taconic Farms)), prepubescent fertile females (donors) (B6C3f1, 4-5 weeks, (Taconic Farms)) and adult fertile females (recipients) (CD1, 2-4 months, (Taconic Farms)).

The donors were acclimated for 1 week and then injected with approximately 8 IU/mouse of Pregnant Mwere's Serum gonadotrophin (Sigma, St. Louis, Mo.) I.P., and 46-47 hours later, 8 IU/mouse of human Chorionic Gonadotropin (hCG (Sigma)) I.P. to induce superovulation. Donors were mated with studs subsequent to hormone injections. Ovulation generally occurs within 13 hours of hCG injection. Copulation was confirmed by the presence of a vaginal plug the morning following mating.

Fertilized eggs were collected under a surgical scope (Leica MZ12 Stereo Microscope, Leica, Wetzlar, Del.). The oviducts were collected and eggs were released into urinanalysis slides containing hyaluronidase (Sigma). Eggs were washed once in hyaluronidase, and twice in Whitten's W640 medium (Table 7) that has been incubated with 5% $CO_2$, 5% $O_2$, and 90% $N_2$ at 37° C. The eggs were then stored in a 37° C./5% $CO_2$ incubator until microinjection.

Ten to twenty micrograms of plasmid DNA containing a cDNA of the Zcyto21gene was linearized, gel-purified, and resuspended in 10 mM Tris pH 7.4, 0.25 mM EDTA pH 8.0, at a final concentration of 5-10 nanograms per microliter for microinjection.

Plasmid DNA was microinjected into harvested eggs contained in a drop of W640 medium overlaid by warm, $CO_2$-equilibrated mineral oil. The DNA was drawn into an injection needle (pulled from a 0 75 mm ID, 1 mm OD borosilicate glass capillary), and injected into individual eggs. Each egg was penetrated with the injection needle, into one or both of the haploid pronuclei.

Picoliters of DNA were injected into the pronuclei, and the injection needle withdrawn without coming into contact with the nucleoli. The procedure was repeated until all the eggs were injected. Successfully microinjected eggs were transferred into an organ tissue-culture dish with pregassed W640 medium for storage overnight in a 37° C./5% $CO_2$ incubator.

The following day, 12-17 healthy 2-cell embryos from the previous day's injection were transferred into the recipient. The swollen ampulla was located and holding the oviduct between the ampulla and the bursa, a nick in the oviduct was made with a 28 g needle close to the bursa, making sure not to tear the ampulla or the bursa. The embryos were implanted through this nick, and by holding onto the peritoneal wall, the reproductive organs were guided back into the abdominal cavity.

The recipients were returned to cages in pairs, and allowed 19-21 days gestation. Animals injected with the Zcyto21 cDNA died before birth.

TABLE 7

WHITTEN'S 640 MEDIA

| | mgs/200 m | mgs/500/ml |
|---|---|---|
| NaCl | 1280 | 3200 |
| KCl | 72 | 180 |
| $KH_2PO_4$ | 32 | 80 |
| $MgSO_4 \cdot 7H_2O$ | 60 | 150 |
| Glucose | 200 | 500 |
| $Ca^{2+}$ Lactate | 106 | 265 |
| K Penn | 15 | 37.5 |
| Streptomycin $SO_4$ | 10 | 25 |
| $NaHCO_3$ | 380 | 950 |
| Na Pyruvate | 5 | 12.5 |

TABLE 7-continued

WHITTEN'S 640 MEDIA

| | mgs/200 m | mgs/500/ml |
|---|---|---|
| H₂0 | 200 | 500 |
| EDTA | 100 µl | 250 µl |
| 5% Phenol Red | 200 µl | 500 µl |
| BSA | 600 | 1500 |

All reagents are available from Sigma.

Example 10

Antibody Production

A: Zcytor19 Polyclonal Antibodies

Polyclonal antibodies are prepared by immunizing 2 female New Zealand white rabbits with the purified recombinant protein huzcytor19/MBP-6H. The rabbits are each given an initial intraperitoneal (ip) injection of 200 µg of purified protein in Complete Freund's Adjuvant followed by booster ip injections of 100 µg peptide in Incomplete Freund's Adjuvant every three weeks. Seven to ten days after the administration of the second booster injection (3 total injections), the animals are bled and the serum is collected. The animals are then boosted and bled every three weeks.

The huzcyotr19/MBP-6H specific rabbit serum is pre-adsorbed of anti-MBP antibodies using a CNBr-SEPHAROSE 4B protein column (Pharmacia LKB, Peapack, N.J.) that is prepared using 10 mg of purified recombinant MBP per gram of CNBr-SEPHAROSE. The huzcytor19-specific polyclonal antibodies are affinity purified from the rabbit serum using a CNBr-SEPHAROSE 4B protein column that is prepared using 10 mg of the specific antigen purified recombinant protein huzcytor19/MBP-6H followed by 20X dialysis in PBS overnight. Huzcytor19-specific antibodies are characterized by ELISA using 500 ng/ml of the purified recombinant proteins huzcytor19/MBP-6H or huzcytor19-Fc4 as antibody targets. The lower limit of detection (LLD) of the rabbit anti-huzcytor19/MBP-6H affinity purified antibody on its specific purified recombinant antigen huzcytor19/MBP-6H and on purified recombinant huzcytor19-Fc4 is determined.

B: Zcyto20, Zcyto21, Zcyto22, Zcyto24, and Zcyto25 Polyclonal Antibodies

Polyclonal antibodies are prepared by immunizing female New Zealand white rabbits with the purified recombinant protein zcyto20/MBP-6H, zcyto21/MBP-6H, and zcyto22/MBP-6H, as well as mouse zcyto24/MBP-6H, or zcyto25/MBP-6H. The rabbits are each given an initial intraperitoneal (ip) injection of 200 µg of purified protein in Complete Freund's Adjuvant followed by booster ip injections of 100 µg peptide in Incomplete Freund's Adjuvant every three weeks. Seven to ten days after the administration of the second booster injection (3 total injections), the animals are bled and the serum is collected. The animals are then boosted and bled every three weeks.

The zcyto20/MBP-6H, zcyto21/MBP-6H, zcyto22/MBP-6H, zcyto24/MBP-6H, or zcyto25/MBP-6H specific rabbit serum can be pre-adsorbed of anti-MBP antibodies using a CNBr-SEPHAROSE 413 protein column (Pharmacia LKB, Peapack, N.J.) that is prepared using 10 mg of purified recombinant MBP per gram of CNBr-SEPHAROSE. The zcyto20, zcyto21, zcyto22, zcyto24, or zcyto25-specific polyclonal antibodies are affinity purified from the rabbit serum using a CNBr-SEPHAROSE 4B protein column that is prepared using 10 mg of the specific antigen purified recombinant protein followed by 20X dialysis in PBS overnight. Antibodies are characterized by ELISA using 500 ng/ml of the purified recombinant proteins as antibody targets. The lower limit of detection (LLD) of the purified antibody on its specific purified recombinant antigen is determined.

Polyclonal antibodies were prepared for zcyto21 using a similar protocol by immunizing rabbits with zcyto21-CEE tagged protein, and the antibodies were purified.

Example 11

Expression of the Zcyto20 Zcyto21 Zcyto22 Zcyto24 and Zcyto25 Genes Following Polyinosinic Acid-Polycytidylic Acid Induction A: Various Cell Types Cultures of primary cells (normal human bronchial epithelial cells, normal human dermal fibroblasts, human umbilical vein endothelial cells, human microvascular endothelial cells and human smooth muscle cells; CLONETICS Corporation; Walkersville, Md.) and human choriocarcinoma cell lines (Jar, BeWo, and 3A-Sub E cells; ATCC, Manassas, Va.) were grown in the presence of polyinosinic acid-polycytidylic acid (poly I:C; 100 µg/ml) (SIGMA; St. Louis, Mo.) or in medium alone. In some instances 10 ng/ml hTNFα or 10 ng/ml hIL1b were also tested. After four hours of incubation, total RNA was isolated from cells and treated with RNase-free DNase. One microgram of total RNA was used for first-stand cDNA synthesis using the Advantage RT-for-PCR kit as suggested by the manufacturer (Clontech, Palo Alto, Calif.). Five percent of the cDNA reaction was used for polymerase chain reaction as suggested by the manufacturer (Clontech) using the following primer pairs: zcyto20, ZC40134 (SEQ ID NO:30), ZC40214 (SEQ ID NO:31); zcyto21, ZC40209 (SEQ ID NO:32), ZC40213 (SEQ ID NO:33); zcyto22, ZC39295 (SEQ ID NO:34), and ZC39298 (SEQ ID NO:35). Primers to G3PDH were used as a control.

Zcyto20 mRNA was detected at low levels in all cell types tested. Increased zcyto20 mRNA levels were seen in in NHBE, HUVEC, JAR, 3-A Sub E and BeWo cells stimulated with poly I:C. Zcyto22 mRNA was detected at low levels in all cell types tested. Increased zcyto22 mRNA levels were seen in in NHBE, JAR, 3-A Sub E and BeWo cells stimulated with poly I:C. These results indicate that zcyto20 and zcyto22 mRNA synthesis is stimulated by the known interferon inducer, poly I:C.

Zcyto21 mRNA was detected at low levels in all cell types tested. Increased zcyto21 mRNA levels were seen in in NHBE, HUVEC, NHDF, SMC, HMVEC, JAR, 3-A Sub E and BeWo cells stimulated with poly I:C. Increased zcyto21 mRNA levels were also seen in IL1b-treated 3-A Sub E placental cells. These results indicate that zcyto21 mRNA synthesis is stimulated by the known interferon inducer, poly I:C and can also be stimulated by the cytokine IL1b in certain cell types.

B: Peripheral Blood Mononuclear Cells

Whole peripheral blood mononuclear cells were isolated from human blood using Ficoll Hypaque. T-cells were were purified from peripheral blood mononuclear cells by VarioMacs positive selection columns as per manufacturer's instructions (Miltenyi Biotec Inc., Auburn, Calif.). Samples from each population were stained and analyzed by fluorescent antibody cell sorting (FACS) (Bectin Dickinson, San Jose, Calif.) analysis to determine the percent enrichment. The CD3+ T-cells were approximately 95% purified. Whole peripheral blood leukocytes or CD3+ T cells were grown in the presence of poly I:C (100 ug/ml) or in medium alone.

After four hours of incubation, total RNA was isolated from cells and treated with RNAse-free DNAse. RT-PCR was performed with the Superscript One-Step RT-PCR with Platinum Taq kit (Invitrogen, Frederick, Md.) using 100 ng total RNA as a template for cDNA synthesis. The PCR primer pairs used were: zcyto20: ZC40134 (SEQ ID NO:30) and ZC40214 (SEQ ID NO:31); zcyto21: ZC40209 (SEQ ID NO:32) and ZC40213 (SEQ ID NO:33); zcyto22: ZC39295 (SEQ ID NO:34) and ZC39298 (SEQ ID NO:35). Aliquots of each RNA, were also tested with primer pairs specific for MHC Class I (Clontech) as a control.

Zcyto20 mRNA was detected in whole peripheral blood mononuclear cells stimulated with poly I:C. The results indicate that zcyto20 mRNA synthesis is stimulated by the known interferon inducer, poly I:C in peripheral blood mononuclear cells.

Zcyto21 mRNA was detected in whole peripheral blood mononuclear cells and CD3+ T-cells stimulated with poly I:C. The results indicate that zcyto21 mRNA synthesis is stimulated by the known interferon inducer, poly I:C in peripheral blood mononuclear cells including CD3+ T cells.

Zcyto22 mRNA was detected in whole peripheral blood mononuclear cells and CD3+ T-cells stimulated with poly I:C. The results indicate that zcyto22 mRNA synthesis is stimulated by the known interferon inducer, poly I:C in peripheral blood mononuclear cells including CD3+ T cells.

These results are indicative of the effect poly I:C would have on zcyto24 and zcyto25 as well as other family members.

Example 12

Expression Analysis of Human Primary Immune Cell and Immune Cell Lines Using RT-PCR A panel of RNAs from primary human immune cell populations and human immune cell lines was screened for zcyto21, zcyto21, and zcyto22 expression using RT-PCR. The panels were made in house and contained RNA from sixteen various resting and activated cells as described below. All primary immune cell populations were isolated from the blood of several anonymous donors. Various immune cell subsets (CD3+, CD14+, CD19+, and CD56+) were then isolated using labeled Microbeads and the Magnetic Cell Separation System from Miltenyi Biotec. RNA was prepared using the RNeasy Midiprep™ Kit (Qiagen, Valencia, Calif.) as per manufacturer's instruction. CD56+ NK cell RNA was isolated from cells in their resting state. One CD3+ population was activated using a combination of 500 ng/ml Ionomycin and 5.0 ng/ml PMA (phorbol 12-myristate 13 acetate). Another CD3+ population was stimulated using the supernatant from Conconavalin A stimulated rat splenocytes, a media known to be rich in cytokines and growth factors. CD3+ cells were collected for RNA isolation at activation times of 0, 4 and 16 hours. The CD19+ samples were isolated from human tonsil and activated with 0.5 ug/ml ionomycin and 10 ng/ml PMA. Cells were then collected at 0, 4 hours and 24 hours and RNA isolated. Human CD14+ monocytes were activated with either 0.1 ng/ml lipopolysaccharide (LPS) or 1.0 ng/ml LPS for 20 hours. Resting and activated cells were then collected and the RNA was isolated. In addition, RNA was isolated from resting and activated human monocyte cell lines HL-60, THP-1 and U937. HL-60 cells were activated overnight with 10 ng/ml PMA. THP-1 cells were activated overnight with 1.0 ng/ml LPS+10 ng/ml IFNgamma. Finally, U937 cells were activated overnight with 10 ng/ml PMA. RT-PCR was performed with the Superscript One-Step RT-PCR with Platinum Taq kit (Invitrogen) using 100 ng total RNA as a template for cDNA synthesis. The PCR primer pairs used were: zcyto20: ZC40632 (SEQ ID NO:36) and ZC40633 (SEQ ID NO:37); zcyto21: ZC40209 (SEQ ID NO:32) and ZC40213 (SEQ ID NO:33); and zcyto22: ZC40638 (SEQ ID NO:38) and ZC40639 (SEQ ID NO:39). Aliquots of each RNA, were also tested with primer pairs specific for MHC Class I (Clontech) as a control.

Zcyto20 mRNA was detected in THP-1 cells treated with LPS and interferon gamma. Zcyto20 mRNA was also detected in CD3+ cells treated with PMA for 4 h. Zcyto21 mRNA was detected at low levels in resting U937 cells and resting THP-1 cells. The level of zcyto21 mRNA was increased upon treatment of the THP-1 cells with LPS and interferon gamma. Zcyto21 mRNA was also detected in CD3+ cells treated with PMA for 4 h. Zcyto22 mRNA was detected in THP-1 cells treated with LPS and interferon gamma. Zcyto22 mRNA was also detected in CD3+ cells treated with PMA for 4 h and 16 h as well as CD3+ cells treated with Conconavalin A for 4 and 16 h. The results indicate that zcyto20, zcyto21, and zcyto22 mRNA synthesis is stimulated by activation of a monocyte cell line and primary CD3+ immune cells.

These results are indicative of the effect poly I:C would have on zcyto24 and zcyto25 as well as other family members.

Example 13

Antiviral Activity: Cytopathic Effect in Hela and L929 Cells

Initial functional assays for antiviral activity were conducted using conditioned media from transiently transfected human embryonal kidney (HEK) cells. Production of this conditioned medium is described as follows. A full-length cDNA for zcyto20, zcyto21, zcyto22, zcyto24, or zcyto25 was cloned into the pzp7Z vector using standard procedures. The zcyto20, zcyto21, zcyto22, zcyto24, or zcyto25 constructs were transfected into 293 HEK cells. Briefly, for each construct 700,000 cells/well (6 well plates) were plated approximately 18 h prior to transfection in 2 milliliters DMEM+10% fetal bovine serum. Per well, 1.5 micrograms zcyto20, zcyto21, zcyto22, zcyto24, or zcyto25 DNA and 0.5 micrograms pIRES2-EGFP DNA (Clontech) were added to 6 microliters Fugene 6 reagent (Roche Biochemicals) in a total of 100 microliters DMEM. Two micrograms pIRES2-EGFP DNA alone was used as a negative control. These transfection mixtures were added 30 minutes later to the pre-plated 293 cells. Twenty-four hours later the cell media were removed and DMEM+0.1% bovine serum albumin was added. Conditioned media was collected after 48 hours, filtered through a 0.45 micron filter and used for antiviral and reporter assays.

Antiviral Assays were carried out using human cervical carcinoma cells (HeLa) and mouse fibroblast cells (L929). On the first day, conditioned medium containing zcyto20, zcyto21, zcyto22, zcyto24, or zcyto25 (See Example 10) was diluted and plated with 50,000 cells in a 96-well flat bottom microtiter plate. Following a 24-hour incubation at 37° C., the medium was removed and replaced with medium containing encephelomyocarditis virus at a multiplicity of infection of 0.1. The cells were again incubated for 24 hours at 37° C. Culture wells were then scored visually on a 4-point scale for the presence of cytopathic effect, which was then converted to % CPE as shown in Table 8. Conditioned medium from cells transfected with GFP alone and purified human interferon-a-2a or murine interferon-alpha were included as controls.

TABLE 8

Determination of Cytopathic Effect

| Designation | Observation of Cytopathic Effect (CPE) |
|---|---|
| − | No CPE |
| +/− | Possible CPE (about 1% of monolayer surface) |
| + | CPE limited to one plaque (about 5% of the surface) |
| +1 | CPE is limited to three plaques, affecting less than 25% of the monolayer |
| 1 | 25% CPE |
| 1-2 | 37% CPE |
| 2 | 50% CPE |
| 2-3 | 62% CPE |
| 3 | 75% CPE |
| 3-4 | 87% CPE |
| 4 | 100% CPE |

Table 9 shows that conditioned medium containing zcyto20, zcyto21, zcyto22, zcyto24, and zcyto25 inhibited viral infection (% CPE) in HeLa cells in a dose-dependent manner, while control GFP conditioned medium failed to significantly block the appearance of cytopathic effect. As shown in Table 10, conditioned medium containing zcyto20, zcyto21, zcyto22, zcyto24, and zcyto25 did not inhibit viral infection in L929 cells. In both experiments purified interferon showed positive antiviral activity.

TABLE 9

Percentage Cytopathic Effect of zcyto20, zcyto21, zcyto22, zcyto24, and zcyto25 in HeLa Cells usin Conditioned Medium (CM)

| Relative CM Concentration | Control GEP | zcyto20 (CM) | zcyto21 (CM) | zcyto22 (CM) | zcyto24 (CM) | zcyto25 (CM) | hIFN-a-2a | hIFN-a-2a Concentration |
|---|---|---|---|---|---|---|---|---|
| No Add | 87 | 87 | 87 | 87 | 87 | 87 | 87 | 0 ng/ml |
| .008X | 87 | 10 | 56 | 0 | 0 | 10 | 15 | .0001 ng/ml |
| .0156X | 87 | 2.5 | 31 | 0 | 0 | 5 | 8.3 | .001 ng/ml |
| .0325X | 87 | 5 | 10 | 0 | 0 | 5 | 1.7 | .01 ng/ml |
| .0625X | 87 | 2.5 | 10 | 0 | 0 | 0 | 0 | .1 ng/ml |
| .125X | 87 | 0 | 5 | 0 | 0 | 0 | 0 | 1 ng/ml |
| .25X | 87 | 0 | 0 | 0 | 0 | 0 | 0 | 10 ng/ml |
| .5X | 87 | 0 | 0 | 0 | 0 | 0 | 0 | 100 ng/ml |

TABLE 10

Percentage Cytopathic Effect of zcyto20, zcyto21, zcyto22, zcyto24, and zcyto25 in L929 Cells using Conditioned Medium (CM)

| Relative CM Conc. | Control GFP | zcyto20 (CM) | zcyto21 (CM) | zcyto22 (CM) | zcyto24 (CM) | zcyto25 (CM) | mIFN-alpha | mIFN-alpha Conc. |
|---|---|---|---|---|---|---|---|---|
| No Add | 87 | 87 | 87 | 87 | 87 | 87 | 87 | 0 ng/ml |
| .008X | 87 | 87 | 87 | 87 | 87 | 87 | 87 | .0001 ng/ml |
| .0156X | 87 | 87 | 87 | 87 | 87 | 87 | 87 | .001 ng/ml |
| .0325X | 87 | 87 | 87 | 87 | 87 | 87 | 87 | .01 ng/ml |
| .0625X | 87 | 87 | 87 | 87 | 87 | 87 | 58 | .1 ng/ml |
| .125X | 87 | 87 | 87 | 87 | 87 | 87 | 6.7 | 1 ng/ml |
| .25X | 87 | 87 | 87 | 87 | 87 | 87 | 0 | 10 ng/ml |
| .5X | 87 | 87 | 87 | 87 | 87 | 87 | 0 | 100 ng/ml |

As a follow up, conditioned medium from Sf9 cells infected with baculovirus expressing zcyto20, zcyto21, zcyto22, zcyto24, and zcyto25 was used in antiviral assays. Conditioned medium from Sf9 cells infected with wild type baculovirus was used as a negative control.

The results of the antiviral assay using the baculovirus-derived conditioned medium were similar to that using the 293 transient transfected conditioned medium. Table 11 shows that baculovirus-derived conditioned medium containing zcyto21 inhibited viral infection in HeLa cells in a dose-dependent manner, while control baculovirus conditioned medium failed to block the appearance of cytopathic effect.

TABLE 11

Percentage Cytopathic Effect in HeLa Cells using Baculovirus-derived zcyto21 Conditioned Medium (CM)

| Relative Concentration | CM zcyto21 CM | Control BV CM | hIFN-a-2a | hIFN-a-2a Concentration |
|---|---|---|---|---|
| No Add | 51 | 51 | 51 | 0 ng/ml |
| .008× | 5.5 | 56 | 17.5 | .001 ng/ml |
| .0156× | 2.5 | 62 | 7.5 | .01 ng/ml |
| .0325× | 5 | 56 | 0 | .1 ng/ml |
| .0625× | 2.5 | 50 | 0 | 1 ng/ml |
| .125× | 2.5 | 56 | 0 | 10 ng/ml |
| .25× | 5 | 62 | 0 | 100 ng/ml |

The production of the baculovirus construct and conditioned medium is described above.

Example 14

Antiviral Activity can not be Blocked by Antibodies Against the Human Interferon Alpha Receptor Chain 2 Beta Additional antiviral assays were carried out using human cervical carcinoma cells (HeLa). On the first day, anti-hu-IFN-Receptor MAb (Research Diagnostics Inc) and Isotypematched negative control MAb were diluted into a 96-well flat bottom microtiter plate. Conditioned medium from Sf9 cells infected with baculovirus expressing zcyto20, zcyto21, or zcyto22 was added to obtain a final concentration of 0.0625X CM and plated with 50,000 HeLa cells per well. Following a 24-hour incubation at 37° C., the medium was removed and replaced with medium containing encephelomyocarditis virus at a multiplicity of infection of 0.1. The cells were again incubated for 24 hours at 37° C. Culture wells were then scored visually for the presence of cytopathic effect (CPE), as shown in Table 8. Purified human interferon-a-2a at a concentration of 0.01 ng/ml was included as a positive control.

Table 12 shows that conditioned medium containing zcyto20, zcyto21, and zcyto22 had antiviral activity in HeLa cells (as indicated by zero % CPE) in the presence or absence of neutralizing antibodies against the human interferon alpha receptor chain 2 beta. In contrast, the antiviral activity of interferon-a-2a was inhibited in a dose-dependent manner specifically in the presence of neutralizing antibodies against the human interferon alpha receptor chain 2 beta. These data indicate that zcyto20 zcyto21, and zcyto22 interact with either a receptor other than the human interferon alpha receptor or it interacts with the human interferon alpha receptor with a different mechanism than human interferon-a-2a.

in growth medium), Zcyto20 (at 2.5×, 0.5×, or 0.1×), and murine Zα30 (at 2.5×, 0.5×, or 0.1×).

The BaF3cell line is washed three times in growth medium, pellets are resuspended in growth medium, cells are counted and diluted in growth medium to 5,000 cells/50 μl. Fifty microliters of diluted cells are then added to each dilution of samples. Assay plates are incubated in a 37° C. incubator for three to four days. Twenty microliters of Alomar blue are then added to each well and the plate are incubated overnight at 37° C. The plates are read on the fluorescent plate reader at excitation wavelength of 544 and emission wavelength 590.

Example 16

Signaling Via Interferon-Response Pathway

Interaction of type 1 interferons with their specific receptor leads to induction of a number of genes responsible for their antiviral/antiproliferative activity. These include 2'-5' oligoadenylate synthetase (2-5A synthetase), double-stranded RNA dependent Pkr kinase (Pkr), phospholipid scramblase, and intercellular adhesion molecule-1 (ICAM-1). Induction of genes with as yet unknown function, such as a 56 kDa interferon stimulated gene product (ISG-56k), also occurs. To determine if some or all of these genes are induced upon

TABLE 12

Percentage Cytopathic Effect in HeLa Cells using zcyto20, zcyto2l, or zcyto22 Conditioned Medium (CM) and Neutralizing Antibodies against the Human Interferon Alpha Receptor Chain 2 Beta

| Anti-hIFNR MAb Concentration | zcyto20 CM + Anti-hIFNR MAb | zcyto20 CM + Control MAb | zcyto21 CM + Anti-hIFNR MAb | zcyto21 CM + Control MAb | zcyto22 CM + Anti-hIFNR MAb | zcyto22 CM + Control MAb | hIFN-a-2a + Anti-hIFNR Mab | hIFN-a-2a + Control MAb |
|---|---|---|---|---|---|---|---|---|
| 0 ug/ml | 0 | 0 | 0 | 0 | 0 | 0 | 7.5 | 10 |
| 0.001 ug/ml | 0 | 0 | 0 | 0 | 0 | 0 | 7.5 | 10 |
| 0.01 ug/ml | 0 | 0 | 0 | 0 | 0 | 0 | 10 | 10 |
| 0.1 ug/ml | 0 | 0 | 0 | 0 | 0 | 0 | 27.5 | 10 |
| 1 ug/ml | 0 | 0 | 0 | 0 | 0 | 0 | 40 | 10 |
| 10 ug/ml | 0 | 0 | 0 | 0 | 0 | 0 | 87 | 10 |

Example 15

Antiproliferation Assay Using a BAF3 Cell Line

BaF3 is used to determine if Zcyto20 has anti-proliferative properties. Baby hamster kidney (BHK) cells are stably transfected with an expression vector containing the CMV promoter plus intron A upstream of the Zcyto20 cDNA or an unrelated cDNA, called Zα30, using BRL LIPO-FECTAMINE®. Stably transfected cells are seeded in a cell factory in serum free media and allowed to grow for three days before conditioned media is harvested and concentrated in a 5K filter to 10×. Concentrated conditioned medium samples are stored at 4° C.

The following assay is used to test for anti-proliferation of BaF3. In a 96 well plate, eight 1:2 serial dilutions are made of growth media alone (RPMI 1640, 10% fetal bovine serum, 1 mM sodium pyruvate, 2 mM L-glutamine), or murine IL-3 (starting at 50 pg/ml in growth medium) with final volume of 100 μl. Fifty microliters of the following are added to both growth media alone or mIL-3 diluted lanes: human interferon-α (100 ng/ml, 10 ng/ml, or 1 ng/ml diluted in growth medium), human interferon-β (100 ng/ml, 10 ng/ml, or 1 ng/ml diluted in growth medium), murine interferon-α (100 ng/ml, 10 ng/ml, or 1 ng/ml diluted in growth medium), murine interferon-β (100 ng/ml, 10 ng/ml, or 1 ng/ml diluted treatment of cells with zcyto20, human Daudi B lymphoid cells were treated for 72 hours with conditioned medium from Sf9 cells infected with baculovirus expressing zcyto20. Conditioned medium from Sf9 cells infected with wild-type baculovirus was used as a negative control. Following treatment cells were collected and lysed for isolation of total RNA. 1 microgram of total RNA was converted to cDNA using reverse transcriptase and used as a template for polymerase chain reaction using oligonucleotide primers specific for the human interferon-stimulated genes described above. Oligonucleotide primers for human glycerol-3-phosphate dehydrogenase (G3PDH) were used as a non-interferon stimulated gene control. The results show clear induction of ISG-56k, Pkr, 2-5A synthetase and phospholipid scramblase following treatment of cells with zcyto20. No induction was seen for ICAM-1 or the non-interferon stimulated gene control, G3PDH.

Example 17

Identification of Zcytor19 as a Receptor for Zcyto21

A: COS Cell Transfection and Secretion Trap

Biotinylated zcyto21 was tested for binding to known or orphan cytokine receptors. The pZP7 expression vectors containing cDNAs of cytokine receptors (including human IFNαR1, IFNβR2, IFNαR1, IFNβR2, IL-10R, CRF2-4, ZcytoR7, DIRS1, Zcytor19, and Tissue Factor) were transfected into COS cells, and the binding of biotinylated zcyto20 to transfected COS cells was carried out using the secretion trap assay described below. Positive binding in this assay showed receptor-ligand pairs.

COS Cell Transfections

The COS cell transfections were performed as follows: COS cells were plated ($1 \times 10^5$ cells/well) on fibronectin coated, 12-well, tissue culture plates (Becton Dickinson, Bedford, Mass.) and incubated at 37° C. overnight. Cytokine receptor DNA (0.75 µg) was mixed with 50 µl serum free DMEM media (55 mg sodium pyruvate, 146 mg L-glutamine, 5 mg transferrin, 2.5 mg insulin, 1 µg selenium and 5 mg fetuin in 500 ml DMEM), then mixed with 5 µl LIPOFECTAMINE® (Invitrogen, Carlsbad, Calif.) in 45 µl serum free DMEM media, and incubated at room temperature for 30 minutes. An additional 400 µl serum free DMEM media was added. The cells were rinsed with serum free DMEM, and 500 µl of the DNA mixture was added. The cells were incubated for 5 hours at 37° C., at which time an additional 500 µl 120% FBS DMEM media (100 ml FBS, 55 mg sodium pyruvate and 146 mg L-glutamine in 500 ml DMEM) was added and the cells were incubated overnight.

Secretion Trap Assay

The secretion trap was performed as follows: Media was aspirated and cells were rinsed twice with 1% BSA in PBS. Cells were blocked for 1 hour with TNB (0.1M Tris-HCL, 0.15M NaCl and 0.5% Blocking Reagent (NEN Renaissance TSA-Direct Kit, NEN Life Science Products, Boston, Mass.) in $H_2O$. The cells were incubated for 1 hour with 3 µg/ml biotinylated zcyto21 protein (Example 27) in TNB. Cells were then washed 3 times with 1% BSA in PBS and were incubated for another hour with 1:300 diluted Streptavidin-HRP (NEN kit) in TNB. Again cells were washed 3 times with 1% BSA in PBS, and then fixed for 15 minutes with 1.8% Formaldehyde in PBS. Cells were then washed 3 times with TNT (0.1M Tris-HCL, 0.15M NaCl, and 0.05% Tween-20 in $H_2O$).

Positive binding was detected with fluorescein tyramide reagent diluted 1:50 in dilution buffer (NEN kit), incubated for 4.5 minutes, and washed with TNT. Cells were preserved with Vectashield Mounting Media (Vector Labs Burlingame, Calif.) diluted 1:5 in TNT. Cells were visualized using a FITC filter on fluorescent microscope.

Positive binding was detected on cells transfected with human zcytor19 cDNA and incubated with biotinylated zcyto21. None of the other transfected receptors bound zcyto21, and zcytor19 did not bind a control biotinylated protein. These data indicate that zcytor19 is a receptor for zcyto21.

Further experiments have shown positive binding between both human and mouse Zcytor19 with biotinylated zcyto21. Positive binding was also detected on cells transfected with human zcytor19 cDNA and incubated with biotinylated zcyto20, and zcyto24.

Example 18

Signal Transduction Reporter Assay

A signal transduction reporter assay can be used to determine the functional interaction of zcyto20, zcyto21, zcyto22, zcyto24, and zcyto25 with zcytor19. Human embryonal kidney (HEK) cells are transfected with a reporter plasmid containing an interferon-stimulated response element (ISRE) driving transcription of a luciferase reporter gene in the presence or absence of pZP7 expression vectors containing cDNAs for class II cytokine receptors (including human DIRS1, IFNαR1, IFNαR2 and Zcytor19 (SEQ ID NOS:23 and 26)). Luciferase activity following stimulation of transfected cells with class II ligands (including zcyto20 (SEQ ID NO: 1), zcyto21 (SEQ ID NO:4), zcyto22 (SEQ ID NO:6), zcyto10, huIL10 and huIFNa-2a) reflects the interaction of the ligand with transfected and native cytokine receptors on the cell surface. The results and methods are described below.

Cell Transfections

HEK cells were transfected as follows: 700,000 293 cells/well (6 well plates) were plated approximately 18 h prior to transfection in 2 milliliters DMEM+10% fetal bovine serum. Per well, 1 microgram pISRE-Luciferase DNA (Stratagene), 1 microgram cytokine receptor DNA and 1 microgram pIRES2-EGFP DNA (Clontech,) were added to 9 microliters Fugene 6 reagent (Roche Biochemicals) in a total of 100 microliters DMEM. Two micrograms pIRES2-EGFP DNA was used when cytokine receptor DNA was not included. This transfection mix was added 30 minutes later to the preplated 293 cells. Twenty-four hours later the transfected cells were removed from the plate using trypsin-EDTA and replated at approximately 25,000 cells/well in 96 well microtiter plates. Approximately 18 h prior to ligand stimulation, media was changed to DMEM+0.5% FBS.

Signal Transduction Reporter Assays

The signal transduction reporter assays were done as follows: Following an 18 h incubation at 37° C. in DMEM+0.5% FBS, transfected cells were stimulated with dilutions (in DMEM+0.5% FBS) of the following class II ligands; zcyto20, zcyto21, zcyto22, zcyto10, huIL10 and huIFNa-2a. Following a 4-hour incubation at 37° C., the cells were lysed, and the relative light units (RLU) were measured on a luminotneter after addition of a luciferase substrate. The results obtained are shown as the fold induction of the RLU of the experimental samples over the medium alone control (RLU of experimental samples/RLU of medium alone=fold induction). Table 14 shows that zcyto20, zcyto21 and zcyto22 induce ISRE signaling in 293 cells transfected with ISRE-luciferase giving a 15 to 17-fold induction in luciferase activity over medium alone. The addition of zcytor19 DNA to the transfection mix results in a 6 to 8-fold further induction in ISRE signaling by zcyto20, zcyto21 and zcyto22 giving a 104 to 125-fold total induction. None of the other transfected class II cytokine receptor DNAs resulted in increased ISRE signaling. These results indicate that zcyto20, zcyto21 and zcyto22 functionally interact with the zcytor19 cytokine receptor. Table 13 also shows that huIFNa-2a can induce ISRE signaling in ISRE-luciferase transfected 293 cells giving a 205-fold induction of luciferase activity compared to medium alone. However, the addition of zcytor19 DNA to the transfection leads to an 11-fold reduction in ISRE-signaling (compared to ISRE-luciferase DNA alone), suggesting that zcytor19 overexpression negatively effects interferon signaling, in contrast to the positive effects of zcytor19 over-expression on zcyto20, zcyto21 and zcyto22 signaling.

TABLE 13

Interferon Stimulated Response Element (ISRE) Signaling of Transfected 293 Cells Following Class II Cytokine Stimulation (Fold Induction)

| Ligand | ISRE-Luc. | ISRE-Luc./Zcytor19 |
|---|---|---|
| Zcyto20 (125 ng/ml) | 15 | 125 |
| Zcyto2l (125 ng/ml) | 17 | 108 |
| Zcyto22 (125 ng/ml) | 17 | 104 |
| HuIFNa-2a (100 ng/ml) | 205 | 18 |

TABLE 13-continued

Interferon Stimulated Response Element (ISRE)
Signaling of Transfected 293 Cells Following
Class II Cytokine Stimulation (Fold Induction)

| Ligand | ISRE-Luc. | ISRE-Luc./Zcytor19 |
|---|---|---|
| Zcyto10 (125 ng/ml) | 1.3 | 1 |
| HuIL10 (100 ng/ml) | 1 | 0.5 |

Example 19

Identification of IL10Rb (CRF2-4) as a Receptor Subunit for Zcytor19

A: IL10Rb Neutralizing Antibody Inhibits ISRE Signaling:

A signal transduction reporter assay was used to determine the functional interaction of zcyto20, zcyto21, and zcyto22 with zcytor19 and IL10Rb (CRF2-4). Human embryonal kidney (HEK) cells or human embryonal kidney (HEK) cells stably overexpressing human zcytoR19 were transfected with a reporter plasmid containing an interferon-stimulated response element (ISRE) driving transcription of a luciferase reporter. Luciferase activity following stimulation of transfected cells with class II ligands (including zcyto20, zcyto21, zcyto22 and huIFNa-2a) in the presence or absence of a neutralizing antibody to IL10Rb (CRF2-4) reflects the interaction of the ligand with cytokine receptors on the cell surface. The results and methods are described below.

Cell Transfections:

To produce 293 HEK cells stably overexpressing human zcytoR19, 293 cells were transfected as follows: 300,000 293 cells/well (6 well plates) were plated approximately 6 h prior to transfection in 2 milliliters DMEM+10% fetal bovine serum. Per well, 2 micrograms of a pZP7 expression vector containing the cDNA of human zcytoR19 (SEQ ID NO:23) was added to 6 microliters Fugene 6 reagent (Roche Biochemicals) in a total of 100 microliters DMEM. This transfection mix was added 30 minutes later to the pre-plated 293 cells. Forty-eight hours later the transfected cells were placed under 2 microgram/milliliter puromycin selection. Puromicin resistant cells were carried as a population of cells.

The 293 HEK cells (wild type or overexpressing human zcytoR19) were transfected as follows: 700,000 293 cells/well (6 well plates) were plated approximately 18 h prior to transfection in 2 milliliters DMEM+10% fetal bovine serum. Per well, 1 microgram pISRE-Luciferase DNA (Stratagene) and 1 microgram pIRES2-EGFP DNA (Clontech) were added to 6 microliters Fugene 6 reagent (Roche Biochemicals) in a total of 100 microliters DMEM. This transfection mix was added 30 minutes later to the pre-plated 293 cells. Twenty-four hours later the transfected cells were removed from the plate using trypsin-EDTA and replated at approximately 25,000 cells/well in 96 well microtiter plates. Approximately 18 h prior to ligand stimulation, media was changed to DMEM+0.5% FBS.

Signal Transduction Reporter Assays:

The signal transduction reporter assays were clone as follows: Following an 18 h incubation at 37 degrees in DMEM+ 0.5% FBS, transfected cells were pretreated with a neutralizing polyclonal goat antibody to IL10Rb (2.5 micrograms/ml for zcyto21; 8 micrograms/ml for zcyto20 and zcyto22, R&D Systems) or PBS for 1 hour at 37 C. Human embryonal kidney (HEK) cells stably overexpressing human zcytoR19 were also pretreated with a non-neutralizing polyclonal goat antibody to IFNAR1 (8 micrograms/ml, R&D Systems) as an antibody control for experiments involving zcyto20 and zcyto22. Pretreated cells were stimulated with dilutions (in DMEM+0.5% FBS) of the following class II ligands; zcyto20, zcyto21, or zcyto22. As a control, huIFNa-2a was run in each experiment. Following a 4-hour incubation at 37 degrees, the cells were lysed, and the relative light units (RLU) were measured on a luminometer after addition of a luciferase substrate. The results obtained are shown as the fold induction of the RLU of the experimental samples over the medium alone control (RLU of experimental samples/ RLU of medium alone fold induction).

Tables 14 and 15 show that induction of ISRE signaling by zcyto20 is inhibited by pretreatment of wild type 293 cells or 293 cells overexpressing human zcytoR19 with a neutralizing antibody to IL10Rb. No or little inhibition is seen of huIFNa-2a induction of ISRE signaling. These results indicate that zcyto20 requires interaction with IL10Rb (CRF2-4) for maximal induction of ISRE signaling and that the receptor for zcyto20 is the heterdimeric combination of zcytoR19 and IL10Rb (CRF2-4).

TABLE 14

IL10Rb Inhibition of ISRE Signaling of Transfected
wild-type 293 Cells Following
Class II Cytokine Stimulation (Fold Induction)

| Cytokine Concentration (ng/ml) | Zcyto20 | Zcyto20 + IL10Rb neutralizing Antibody | HuIFNa-2a | HuIFNa-2a + IL10Rb neutralizing Antibody |
|---|---|---|---|---|
| 100 | 8.4 | 0.8 | 152 | 102 |
| 10 | 4 | 0.9 | 160 | 117 |
| 1 | 1 | 0.9 | 90 | 69 |
| 0.1 | 1 | 1 | 12 | 6 |
| 0.01 | 1 | 0.8 | 1.2 | 1 |
| 0 | 1 | 1 | 1 | 1 |

TABLE 15

IL10Rb Inhibition of ISRE Signaling of Transfected
zcytoR19-overexpressing 293 Cells Following
Class II Cytokine Stimulation (Fold Induction)

| Cytokine Concentration (ng/ml) | Zcyto20 | Zcyto20 + IL10Rb neutralizing Antibody | HuIFNa-2a | HuIFNa-2a ILIORb neutralizing Antibody |
|---|---|---|---|---|
| 100 | 91 | 60 | 16 | 16 |
| 10 | 97 | 23 | 14 | 15 |
| 1 | 68 | 1.3 | 8 | 8.4 |
| 0.1 | 6 | 1.1 | 1.5 | 1.9 |
| 0.01 | 1.1 | 1.2 | 1.2 | 1.3 |
| 0 | 1 | 1 | 1 | 1 |

Tables 16 and 17 show that ISRE signaling by zcyto21 is inhibited by pretreatment of wild type 293 cells or 293 cells overexpressing human zcytoR19 with a neutralizing antibody to IL10Rb. No inhibition is seen of huIFNa-2a induction of ISRE signaling. These results indicate that zcyto21 requires interaction with IL10Rb (CRF2-4) for maximal induction of ISRE signaling and that the receptor for zcyto21 is the heterdimeric combination of zcytoR19 and IL10Rb (CRF2-4).

TABLE 16

IL10Rb Inhibition of ISRE Signaling of Transfected
wild-type 293 Cells Following
Class II Cytokine Stimulation (Fold Induction)

| Cytokine Concentration (ng/ml) | Zcyto21 | Zcyto21 + IL10Rb neutralizing Antibody | HuIFNa-2a | HuIFNa-2a + IL10Rb neutralizing Antibody |
|---|---|---|---|---|
| 100 | 4.1 | 1.8 | 31 | 30 |
| 10 | 3.2 | 1.4 | 32 | 31 |
| 1 | 1.5 | 1.3 | 16.3 | 15 |
| 0.1 | 1.1 | 1.3 | 1.4 | 2 |
| 0.01 | 1.2 | 1.3 | 1.1 | 1.2 |
| 0.001 | 1.2 | 1.3 | 0.9 | 2.1 |
| 0 | 1 | 1 | 1 | 1 |

TABLE 17

IL10Rb Inhibition of ISR) Signaling of Transfected
zcytoR19-overexpressing 293 Cells Following
Class II Cytokine Stimulation (Fold Induction)

| Cytokine Concentration (ng/ml) | Zcyto21 | Zcyto21 + IL10Rb neutralizing Antibody | HuIFNa-2a | HuIFNa-2a + IL10Rb neutralizing Antibody |
|---|---|---|---|---|
| 100 | 45 | 31 | 9 | 7.7 |
| 10 | 48 | 28 | 9 | 8.5 |
| 1 | 35 | 5.8 | 4.3 | 4.3 |
| 0.1 | 3.5 | 1 | 1.4 | 1.3 |
| 0.01 | 1.5 | 1.1 | 0.9 | 1.2 |
| 0.001 | 1.1 | 1 | 1.2 | 1 |
| 0 | 1 | 1 | 1 | 1 |

Tables 18 and 19 show that induction of ISRE signaling by zcyto22 is inhibited by pretreatment of wild type 293 cells or 293 cells overexpressing human zcytoR19 with a neutralizing antibody to IL10Rb. No or little inhibition is seen of huIFNa-2a induction of ISRE signaling. These results indicate that zcyto22 requires interaction with IL10Rb (CRF2-4) for maximal induction of ISRE signaling and that the receptor for zcyto22 is the heterdimeric combination of zcytoR19 and IL10Rb (CRF2-4).

TABLE 18

IL10Rb Inhibition of ISRE Signaling of Transfected
wild-type 293 Cells Following
Class II Cytokine Stimulation (Fold Induction)

| Cytokine Concentration (ng/ml) | Zcyto22 | Zcyto22 + IL10Rb neutralizing Antibody | HuIFNa-2a | HuIFNa-2a + IL10Rb neutralizing Antibody |
|---|---|---|---|---|
| 100 | 11 | 1.2 | 152 | 102 |
| 10 | 8 | 1 | 160 | 117 |
| 1 | 1.8 | 0.8 | 90 | 69 |
| 0.1 | 1.2 | 0.8 | 12 | 6 |
| 0.01 | 0.9 | 0.9 | 1.2 | 1 |
| 0 | 1 | 1 | 1 | 1 |

TABLE 19

IL10Rb Inhibition of ISRE Signaling of Transfected
zcytoR19-overexpressing 293 Cells Following
Class II Cytokine Stimulation (Fold Induction)

| Cytokine Concentration (ng/ml) | Zcyto22 | Zcyto22 + IL10Rb neutralizing Antibody | HuIFNa-2a | HuIFNa-2a + IL10Rb neutralizing Antibody |
|---|---|---|---|---|
| 100 | 82 | 76 | 16 | 16 |
| 10 | 97 | 39 | 14 | 15 |
| 1 | 69 | 2.3 | 8 | 8.4 |
| 0.1 | 8.4 | 1.1 | 1.5 | 1.9 |
| 0.01 | 1 | 1.3 | 1.2 | 1.3 |
| 0 | 1 | 1 | 1 | 1 |

B: A: Anti-IL10Rb Antibody Blocks Antiviral Activity

An antiviral assay was performed to determine the ability of anti-IL10Rb antibody to block the antiviral activity of zcyto20. The assay was carried out using 293 HEK cells (wild type or overexpressing human zcytoR19). On the first day, antibodies (anti-human IL10R beta, anti-human Leptin receptor, R&D Systems) were diluted into cell media at 5 micrograms/ml and then plated with 50,000 cells per well into a 96-well plate. Following a one-hour incubation at 37° C., zcyto20-CEE (from example 3) (200 ng/ml for wild-type 293 cells, 0.5 ng/ml for 293 cells overexpressing human zcytoR19) or human interferon-a-2a (1 ng/ml for wild-type 293 cells, 100 ng/ml for 293 cells overexpressing human zcytoR19) were added to the wells and incubated overnight at 37° C. The next day, the medium was removed and replaced with medium containing encephalomyocarditis virus (EMCV) at a multiplicity of infection of 0.1. The cells were then incubated at 37° C. overnight. Subsequently, 25 uL of 5 mg/ml Methylthiazoletetrazolium (MTT)(Sigma) were added to each well, incubated 2 hours at 37 degrees, and wells were then extracted with 100 uL extraction buffer (12.5% SDS, 45% DMF). Following overnight incubation at 37° C., the optical density at 570 nM was measured on a Spectromax plate reader (Molecular Devices, CA). Decreased optical density (570 nm) indicates decreased cell survival (loss of antiviral activity). The optical densities (570 nm) for the different experimental conditions are shown in Table 20 below. The results indicate that blocking human IL10 receptor beta specifically neutralizes the antiviral activity of zcyto20 without effecting interferon-a-2a activity. This indicates that human IL10 receptor beta is part of the receptor complex (including human zcytoR19) involved in zcyto20 antiviral activity.

TABLE 20

Optical Density (570 nm) of ECMV-Infected
Cytokine-Treated Cells

| Cytokine | Wild-type 293 Cells: Anti-IL10Rb | Wild-type 293 Cells: Anti-LeptinR | HuzcytoR19-over-expressing 293 Cells: Anti-IL10Rb | HuzcytoR19-over-expressing 293 Cells: Anti-LeptinR |
|---|---|---|---|---|
| Zcyto20-CEE | .94 | .88 | .95 | .24 |
| HuIFNa-2a | .58 | .4 | .18 | .05 |

C: Zcyto20, Zcyto21, and Zcyto22 Signaling is Enhanced by Coexpression of Zcytor19 and IL10Rb:

A signal transduction reporter assay was used to determine the functional interaction of zcyto20, zcyto21 and zcyto22 with zcytor19 and IL10Rb (CRF2-4). Hamster kidney (BHK) cells were transfected with a reporter plasmid containing an interferon-stimulated response element (ISRE) driving transcription of a luciferase reporter gene in the presence or absence of pZP7 expression vectors containing cDNAs for class II cytokine receptors Zcytor19 and IL10Rb (CRF2-4). Luciferase activity following stimulation of transfected cells with class II ligands (including zcyto20, zcyto21 and zcyto22) reflects the interaction of the ligand with transfected and native cytokine receptors on the cell surface. The results and methods are described below.

Cell Transfections

BHK-570 cells were transfected as follows: 200,000 BHK cells/well (6 well plates) were plated approximately 5 h prior to transfection in 2 milliliters DMEM+5% fetal bovine serum. Per well, 1 microgram pISRE-Luciferase DNA (Stratagene), 1 microgram cytokine receptor DNA and 1 microgram pIRES2-EGFP DNA (Clontech) were added to 9 microliters Fugene 6 reagent (Roche Biochemicals) in a total of 100 microliters DMEM. Two micrograms pIRES2-EGFP DNA was used when cytokine receptor DNA was not included. This transfection mix was added 30 minutes later to the pre-plated BHK cells. Twenty-four hours later the transfected cells were removed from the plate using trypsin-EDTA and replated at approximately 25,000 cells/well in 96 well microtiter plates. Approximately 18 h prior to ligand stimulation, media was changed to DMEM 0.5% FBS.

Signal Transduction Reporter Assays

The signal transduction reporter assays were done as follows: Following an 18 h incubation at 37° C. in DMEM 0.5% FBS, transfected cells were stimulated with dilutions (in DMEM 0.5% FBS) of zcyto20, zcyto21, zcyto22, zcyto24, and zcyto25 ligands. Following a 4-hour incubation at 37 degrees, the cells were lysed, and the relative light units (RLU) were measured on a luminometer after addition of a luciferase substrate. The results obtained are shown as the fold induction of the RLU of the experimental samples over the medium alone control (RLU of experimental samples/RLU of medium alone=fold induction). Table 21 shows that zcyto20, zcyto21 and zcyto22 induce ISRE signaling in BHK cells transfected with ISRE-luciferase and zcytoR19 in a dose-dependent manner. The addition of IL10Rb (CRF2-4) DNA to the transfection mix results in a half-maximal induction of signaling at a 10-100 fold lower cytokine dose. No response was seen with ISRE transfection alone. These results show that the ability of zcyto20, zcyto21 and zcyto22 to signal through the interferon stimulated response element is enhanced by coexpression of zcytoR19 and IL10Rb (CRF2-4) indicating that the receptor for zcyto20, zcyto21 and zcyto22 is the heterdimeric combination of zcytoR19 and IL10Rb (CRF2-4).

Example 20

Construction of Mammalian Expression Vectors that Express Zcytor19 Soluble Receptors: Zcytor19CEE, Zcytor19CFLG, Zcytor19CHIS and Zcytor19-Fc4

An expression vector is prepared for the expression of the soluble, extracellular domain of the zcytor19 polypeptide, pC4zcytor19CEE, wherein the construct is designed to express a zcytor19 polypeptide comprised of the predicted initiating methionine and truncated adjacent to the predicted transmembrane domain, and with a C-terminal Glu-Glu tag (SEQ ID NO:16).

A zcytor19 DNA fragment comprising the zcytor19 extracellular or cytokine binding domain of zcytor19 described herein, is created using PCR, and purified using standard methods. The excised DNA is subcloned into a plasmid expression vector that has a signal peptide, e.g., the native zcytor19 signal peptide, and attaches a Glu-Glu tag (SEQ ID NO:16) to the C-terminus of the zcytor19 polypeptide-encoding polynucleotide sequence. Such a mammalian expression vector contains an expression cassette having a mammalian promoter, multiple restriction sites for insertion of coding sequences, a stop codon and a mammalian terminator. The plasmid can also have an E. coli origin of replication, a mammalian selectable marker expression unit having an SV40 promoter, enhancer and origin of replication, a DHFR gene and the SV40 terminator.

Restriction digested zcytor19 insert and previously digested vector are ligated using standard molecular biological techniques, and electroporated into competent cells such as DH10B competent cells (GIBCO BRL, Gaithersburg, Md.) according to manufacturer's direction and plated onto LB plates containing 50 mg/ml ampicillin, and incubated overnight. Colonies are screened by restriction analysis of DNA prepared from individual colonies. The insert sequence of positive clones is verified by sequence analysis. A large scale plasmid preparation is done using a QIAGEN® Maxi prep kit (Qiagen) according to manufacturer's instructions.

The same process is used to prepare the zcytor19 soluble receptors with a C-terminal his tag, composed of 6 His residues in a row; and a C-terminal FLAG® tag (SEQ ID NO:42), zcytor19CFLAG. To construct these constructs, the aforementioned vector has either the C-HIS or the FLAG® tag in place of the glu-glu tag (SEQ ID NO:16).

An expression vector, zcytor19/Fc4/pzmp20, was prepared to express a C-terminally Fc4 tagged soluble version of zcy-

TABLE 21

Interferon Stimulated Response Element (ISRE) Signaling of Transfected BHK Cells Following Class II Cytokine Stimulation (Fold Induction)

| Class II ligand Concentration (ng/ml) | zcyto20/cells transfected with zcytoR19 alone | zcyto20/cells transfected with zcytoR19 and IL10Rb (CRF2-4) | zcyto21/cells transfected with zcytoR19 alone | zeyto21/cells transfected with zcytoR19 and IL10Rb (CRF2-4) | zcyto22/cells transfected with zcytoR19 alone | zcyto22/cells transfected with zcytoR19 and IL10Rb (CRF2-4) |
|---|---|---|---|---|---|---|
| 1000 | 2.25 | 2.1 | 3.3 | 2.2 | 1.8 | 2.2 |
| 100 | 2.2 | 2.6 | 2.6 | 2.5 | 2 | 2.2 |
| 10 | 2.1 | 2.4 | 2.4 | 2.6 | 1.9 | 2.7 |
| 1 | 1.3 | 2.5 | 2 | 2.5 | 1.5 | 2.7 |
| 0.1 | 1.25 | 2.1 | 1.4 | 2.2 | 1.1 | 2.4 |
| 0.01 | 1.2 | 1.6 | 1.4 | 1.6 | 1.2 | 1.7 |
| 0.001 | 1.4 | 1.5 | 1.3 | 1.3 | 1.2 | 1.3 |
| 0 | 1 | 1 | 1 | 1 | 1 | 1 | tor19 (human zcytor19-Fc4) in BHK cells. A fragment of zcytor19 cDNA that includes the polynucleotide sequence from extracellular domain of the zcytor19 receptor was fused in frame to the Fc4 polynucleotide sequence (SEQ ID NO:43) to generate a zcytor19-Fc4 fusion. The pzmp20 vector is a mammalian expression vector that contains the Fc4 polynucleotide sequence and a cloning site that allows rapid construction of C-terminal Fc4 fusions using standard molecular biology techniques.

A 630 base pair fragment was generated by PCR, containing the extracellular domain of human zcytor19 with BamHI and Bgl2 sites coded on the 5' and 3' ends, respectively. This PCR fragment was generated using primers ZC37967 (SEQ ID NO:44) and ZC37972 (SEQ ID NO:45) by amplification from human brain cDNA library. The PCR reaction conditions were as follows: 30 cycles of 94° C. for 20 seconds, and 68° C. for 2 minutes; 1 cycle at 68° C. for 4 minutes; followed by a 10° C. soak. The fragment was digested with BamHI and Bgl2 restriction endonucleases and subsequently purified by 1% gel electrophoresis and band purification using QIAQUICK® gel extraction kit (Qiagen). The resulting purified DNA was ligated for 5 hours at room temperature into a pzmp20 vector previously digested with Bgl2 containing Fc4 3' of the Bgl2 sites.

One µl of the ligation mix was electroporated in 37 pd. DH10B electrocompetent *E. coli* (Gibco) according to the manufacturer's directions. The transformed cells were diluted in 400 pd. of LB media and plated onto LB plates containing 100 µg/ml ampicillin. Clones were analyzed by restriction digests and positive clones were sent for DNA sequencing to confirm the sequence of the fusion construct.

Example 21

Mammalian Expression Human Zcytor19 Soluble Receptor: Zcytor19/Fc4

BHK 570 cells (ATCC NO: CRL-10314) were plated in T-75 tissue culture flasks and allowed to grow to approximately 50 to 70% confluence at 37° C., 5% $CO_2$, in DMEM/FBS media (DMEM, Gibco/BRL High Glucose, (Gibco BRL, Gaithersburg, Md.), 5% fetal bovine serum, 1 mM L-glutamine (JRH Biosciences, Lenea, Kans.), 1 mM sodium pyruvate (Gibco BRL)). The cells were then transfected with the plasmid zcytor19/Fc4/pzmp20 (Example 4B) using LIPOFECTAMINE® (Gibco BRL), in serum free (SF) media formulation (DMEM, 10 mg/ml transferrin, 5 mg/ml insulin, 2 mg/ml fetuin, 1% L-glutamine and 1% sodium pyruvate). Ten µg of the plasmid DNA zcytor19/Fc4/pzmp20 (Example 4B) was diluted into a 15 ml tube to a total final volume of 500 with SF media. 50 µl of LIPOFECTAMINE® was mixed with 450 µl of SF medium. The LIPOFECTAMINE® mix was added to the DNA mix and allowed to incubate approximately 30 minutes at room temperature. Four ml of SF media was added to the DNA:LIPOFECTAMINE® mixture. The cells were rinsed once with 5 ml of SF media, aspirated, and the DNA:LIPOFECTAMINE® mixture was added. The cells were incubated at 37° C. for five hours, and then 5 ml of DMEM/10% FBS media was added. The flask was incubated at 37° C. overnight after which time the cells were split into the selection media (DMEM/FBS media from above with the addition of 1 µM methotrexate (Sigma Chemical Co., St. Louis, Mo.) in 150 mm plates at 1:2, 1:10, and 1:50. Approximately 10 days post-transfection, one 150 mm plate of 1 µM methotrexate resistant colonies was trypsinized, the cells were pooled, and one-half of the cells were replated in 10 µM methotrexate; to further amplify expression of the zcytor19/Fc4 protein. A conditioned-media sample from this pool of amplified cells was tested for expression levels using SDS-PAGE and Western analysis.

Single clones expressing the soluble receptors can also be isolated, screened and grown up in cell culture media, and purified using standard techniques. Moreover, CHO cells are also suitable cells for such purposes.

Example 22

Assessing Zcytor19 Receptor Heterodimerization Using ORIGEN Assay

Soluble zcytor19 receptor is biotinylated by reaction with a five-fold molar excess of sulfo-NHS-LC-Biotin (Pierce, Inc., Rockford, Ill.) according to the manufacturer's protocol. Soluble zcytor19 receptor and another soluble receptor subunit, for example, soluble class II cytokine receptors, for example, CRF2-4 (SEQ ID NO:40), are labeled with a five fold molar excess of Ru-BPY-NHS (Igen, Inc., Gaithersburg, Md.) according to manufacturer's protocol. The biotinylated and Ru-BPY-NHS-labeled forms of the soluble zcytor19 receptor can be respectively designated Bio-zcytor19 receptor and Ru-zcytor19; the biotinylated and Ru-BPY-NHS-labeled forms of the other soluble receptor subunit can be similarly designated. Assays are carried out using conditioned media or using purified ligands.

For initial soluble receptor binding characterization, the cytokines mentioned above, or conditioned medium, are tested to determine whether they can mediate homodimerization of zcytor19 receptor and if they can mediate the heterodimerization of zcytor19 receptor with the soluble receptor subunits described above. To do this, 50 µl of conditioned media or TBS-B containing purified cytokine, is combined with 50 µl of TBS-B (20 mM Tris, 150 mM NaCl, 1 mg/ml BSA, pH 7.2) containing e.g., 400 ng/ml of Ru-zcytor19 receptor and Bio-zcytor19, or 400 ng/ml of Ru-zcytor19 receptor and e.g., Bio-CRF2-4, or 400 ng/ml of e.g., Ru-CRF2-4 and Bio-zcytor19. Following incubation for one hour at room temperature, 30 µg of streptavidin coated, 2.8 mm magnetic beads (Dynal, Inc., Oslo, Norway) are added and the reaction incubated an additional hour at room temperature. 200 µl ORIGEN assay buffer (Igen, Inc., Gaithersburg, Md.) is then added and the extent of receptor association measured using an M8 ORIGEN analyzer (Igen, Inc.).

Example 23

Construct for Generating a Zcytor19 Receptor Heterodimer

A vector expressing a secreted human zcytor19 heterodimer is constructed by fusing the extracellular cytokine-binding domain of zcytor19 to the heavy chain of IgG gamma 1 (IgGγ1), and the extracellular portion of the heteromeric cytokine receptor subunit (E.g., class II cytokine receptors, for example, CRF2-4) is fused to a human kappa light chain (human κ light chain).

a. Construction of IgG Gamma 1 and Human κ Light Chain Fusion Vectors

The heavy chain of IgGγ1 is cloned into the Zem229R mammalian expression vector (ATCC deposit No. 69447) such that any desired cytokine receptor extracellular domain having a 5' EcoRI and 3' NheI site can be cloned in resulting in an N-terminal extracellular domain-C-terminal IgGγ1 fusion. The IgGγ1 fragment used in this construct is made by using PCR to isolate the IgGγ1 sequence from a Clontech human Fetal Liver cDNA library as a template. PCR products are purified using methods described herein and digested with MluI and EcoRI (Boerhinger-Mannheim), ethanol precipitated and ligated with oligos that comprise an MluI/EcoRI linker, into Zem229R previously digested with and EcoRI using standard molecular biology techniques disclosed herein.

The human κ light chain is cloned in the Zem228R mammalian expression vector (ATCC deposit No. 69446) such that any desired cytokine receptor extracellular domain having a 5' EcoRI site and a 3' KpnI site can be cloned in resulting in a N-terminal cytokine extracellular domain-C-terminal human κ light chain fusion. As a KpnI site is located within the human κ light chain sequence, a special primer is designed to clone the 3' end of the desired extracellular domain of a cytokine receptor into this KpnI site: The primer is designed so that the resulting PCR product contains the desired cytokine receptor extracellular domain with a segment of the human κ light chain up to the KpnI site. This primer preferably comprises a portion of at least 10 nucleotides of the 3' end of the desired cytokine receptor extracellular domain fused in frame 5' to the human kappa light chain. The human κ light chain fragment used in this construct is made by using PCR to isolate the human κ light chain sequence from the same Clontech human Fetal Liver cDNA library used above. PCR products are purified using methods described herein and digested with Mini and EcoRI (Boerhinger-Mannheim), ethanol precipitated and ligated with the MluI/EcoRI linker described above, into Zem228R previously digested with and EcoRI using standard molecular biology techniques disclosed herein.

b. Insertion of Zcytor19 Receptor or Heterodimeric Subunit Extracellular Domains into Fusion Vector Constructs Using the construction vectors above, a construct having zcytor19 fused to IgGγ1 is made. This construction is done by PCRing the extracellular domain or cytokine-binding domain of zcytor19 receptor described herein from a prostate cDNA library (Clontech) or activated lymphocyte cDNA library using standard methods, and oligos that provide EcoRI and NheI restriction sites. The resulting PCR product is digested with EcoRI and NheI, gel purified, as described herein, and ligated into a previously EcoRI and NheI digested and band-purified Zem229R/IgGγ1 described above. The resulting vector is sequenced to confirm that the zcytor19/IgG gamma 1 fusion (zcytor19/Ch1 IgG) is correct.

A separate construct having a heterodimeric cytokine receptor subunit, i.e., CRF2-4, extracellular domain fused to κ light is also constructed as above. The cytokine receptor/human κ light chain construction is performed as above by PCRing from, e.g., a lymphocyte cDNA library (Clontech) using standard methods, and oligos that provide EcoRI and KpnI restriction sites. The resulting PCR product is digested with EcoRI and KpnI and then this product is ligated into a previously EcoRI and KpnI digested and band-purified Zem228R/human κ light chain vector described above. The resulting vector is sequenced to confirm that the cytokine receptor subunit/human κ light chain fusion is correct.

c. Co-Expression of the Zcytor19 and Heterodimeric Cytokine Receptor Subunit Extracellular Domain Approximately 15 μg of each of vectors above, are co-transfected into mammalian cells, e.g., BHK-570 cells (ATCC No. CRL-10314) using LIPOFECTAMINEPLUS® reagent (Gibco/BRL), as per manufacturer's instructions. The transfected cells are selected for 10 days in DMEM 5% FBS (Gibco/BRL) containing 1 μM of methotrexate (MTX) (Sigma, St. Louis, Mo.) and 0.5 mg/ml G418 (Gibco/BRL) for 10 days. The resulting pool of transfectants is selected again in 10 μm of MTX and 0.5 mg/ml G418 for 10 days.

The resulting pool of doubly selected cells is used to generate protein. Three Factories (Nunc, Denmark) of this pool are used to generate 10 L of serum free conditioned medium. This conditioned media is passed over a 1 ml protein-A column and eluted in about 10, 750 microliter fractions. The fractions having the highest protein concentration are pooled and dialyzed (10 kD MW cutoff) against PBS. Finally the dialyzed material is submitted for amino acid analysis (AAA) using routine methods.

d. Reconstitution of Zcytor19 Receptor In Vitro

To identify components involved in the zcytor19-signaling complex, receptor reconstitution studies are performed as follows. For example, BHK 570 cells (ATCC No. CRL-10314) transfected, using standard methods described herein, with a luciferase reporter mammalian expression vector plasmid serve as a bioassay cell line to measure signal transduction response from a transfected zcytor19 receptor complex to the luciferase reporter in the presence of zcytor19 Ligand. BHK cells would be used in the event that BHK cells do not endogenously express the zcytor19 receptor. Other cell lines can be used. An exemplary luciferase reporter mammalian expression vector is the KZ134 plasmid which is constructed with complementary oligonucleotides that contain STAT transcription factor binding elements from 4 genes. A modified c-fos S is inducible element (m67SIE, or hSIE) (Sadowski, H. et al., Science 261:1739-1744, 1993), the p21 SIE1 from the p21 WAF1 gene (Chin, Y. et al., Science 272:719-722, 1996), the mammary gland response element of the β-casein gene (Schmitt-Ney, M. et al., Mol. Cell. Biol. 11:3745-3755, 1991), and a STAT inducible element of the Fcg R1 gene, (Seidel, H. et al., Proc. Natl. Acad. Sci. 92:3041-3045, 1995). These oligonucleotides contain Asp718-XhoI compatible ends and are ligated, using standard methods, into a recipient firefly luciferase reporter vector with a c-Fos promoter (Poulsen, L. K. et al., J. Biol. Chem. 273:6229-6232, 1998) digested with the same enzymes and containing a neomycin selectable marker. The KZ134 plasmid is used to stably transfect BHK, or BaF3 cells, using standard transfection and selection methods, to make a BHK/KZ134 or BaF3/KZ134 cell line respectively.

The bioassay cell line is transfected with zcytor19 receptor alone, or co-transfected with zcytor19 receptor along with one of a variety of other known receptor subunits. Receptor complexes include but are not limited to zcytor19 receptor only, various combinations of zcytor19 receptor with class II cytokine receptors, for example, interferon-gamma, alpha and beta chains and the interferon-alpha/beta receptor alpha and beta chains, zcytor11 (commonly owned U.S. Pat. No. 5,965,704), CRF2-4, DIRS1, zcytor7 (commonly owned U.S. Pat. No. 5,945,511) receptors. Each independent receptor complex cell line is then assayed in the presence of cytokine-conditioned media or purified cytokines and luciferase activity measured using routine methods. The untransfected bioassay cell line serves as a control for the background luciferase activity, and is thus used as a baseline to compare signaling by the various receptor complex combinations. The conditioned medium or cytokine that binds the zcytor19 receptor in the presence of the correct receptor complex, is expected to give a luciferase readout of approximately 5 fold over background or greater.

As an alternative, a similar assay can be performed wherein the a Baf3/zcytor19 cell line isco-transfected as described

Example 24

Binding of Ligands to Soluble Receptors

The binding of the ligands (zcyto20, zcyto21, zcyto22, zcyto24, and zcyto25) to soluble receptors can be assayed using an iodo-bead labeling method. For example, $^{125}$I labeled zcyto2'-CEE is labeled ($1.2 \times 10^7$ CPM/ml; 1.5 ng/ul; and $8.6 \times 10^6$ CPM/ug).

Fifty nanograms of the $^{125}$I labeled zcyto21-cEE (See Example 3) (399,600 CPM) is combined with 1000 ng of cold zcytor19/Fc4 homodimer receptor, 1000 ng cold zcytor19/CRF2-4 heterodimer receptor, or 1000 ng of a control Class II cytokine receptor/Fc4 receptor as a control with about 10,000 ng of cold zcyto21 as a competitor. Samples are incubated for 2 hours at 4° C., after which 30 ul protein-G (Zymed San Francisco, Calif.) is added to each sample. Samples are incubated for 1 hour at 4° C., and washed 3 times with PBS. Radioactivity of the washed protein-G is measured in a gamma counter (Packard Instruments, Downers Grove, Ill.).

Example 25

Flow Cytometry Staining of Human Monocytes with Zcyto20 and Zcyto21-Biotin

Peripheral blood leukocytes (PBLs) were isolated by Ficoll Hypaque (Amersham, Sweden) separation from heparinized human blood. The PBLs were cultured at 37° C. in standard media at a density of $1 \times 10^e6$ cells per milliliter in 6-well tissue culture plates. Following overnight incubation, the PBLs were harvested and stained with biotinylated zcyto20-cee and zcyto21-cee (See Example 18) at a concentration of 10 ug/ml. Staining was detected with Phycoerythrin-labeled streptavidin (Pharmingen, CA, USA) that was prepared at a dilution of 1:1000. Following staining the PBLs were fixed in 2% Paraformaldehyde, and read on a Facscaliber (Becton Dickinson, San Diego, Calif.). The data was analyzed using Cellquest software (Becton Dickinson). Results indicate that both biotinylated zcyto20-cee and zcyto2'-cee stain cells in the myeloid gate of peripheral blood leukocytes. Cells in the lymphoid gate do not bind zcyto20-cee and zcyto21-cee.

Example 26

Zcyto21-CEE Effects on Expression of Activation Markers on PBLs

Peripheral blood leukocytes (PBLs) were isolated by Ficoll Hypaque separation from heparinized human blood. The PBLs were then stimulated with purified protein or media controls from the following: 1) zcyto21-CEE (2 ug/ml); 2) zcyto21-cee (1 ug/ml); 3) Media alone; 4) A141F negative control protein (2 ug/ml); or 5) IFN-alpha-A (1 ng/ml) (PBL Biomedical NJ, USA.). The stimulated PBLs were incubated at a cell density of $1 \times 10^e6$ cells per milliliter in at 37° C. with 5% $CO_2$. Cultures were harvested at 24 and 48 hours and stained for activation markers.

The PBLs were washed with PBS and then blocked with normal mouse IgG in Facs buffer (HBSS+2% normal goat serum, 2% BSA, 0.2% NaN3), followed by staining with antibodies for the following markers: CD19, CD14, CD3, HLA-DR, CD54, HLA-ABC (Pharmingen, CA, USA and Immunotech, France). Cells were washed and then fixed in 2% Paraformaldehyde before being analyzed on a Facscaliber (Becton Dickinson, Calif., USA). The resulting data were analyzed using Cellquest software (Becton Dickinson, Calif., USA).

Results indicated an increase in surface CD54 (ICAM) expression on monocytes at 24 and 48 hours with zcyto21-cee stimulation, compared to the media alone control. Stimulation with zcyto21-cee also resulted in an increase in Major histocompatibility complex I expression on B-cells at 24 hours and an increase in MHCI on both B-cells and Monocytes at 48 hours.

Example 27

Biotinylation of Ligands

Zcyto210EE were biotinylated by following a modified protocol by Pierce Chemical Company for sulfo-NHS-LC-Biotin. Two hundred and fifty micrograms of zcyto21CEE (in 0.5 ml PBS) was added to 8.4 ul of S-NHS-biotin stock (84 ug), and incubated at room temperature for 2 hours with rocking. Following the incubation step, 20 ul 2M TrisHCl (pH8) was added, and the mixture was incubated for 20 minutes at room temperature with rocking. The biotinylated ligand mixtures were then stored at 4° C. Zcyto20CEE, zcyto22CEE and zcyto24CEE were prepared in essentially the same manner.

Example 28

Expression of Zcytor19 by Northern Analysis

Northern blots were probed to determine the tissue distribution of zcytor19. A human zcytor19 cDNA fragment was obtained using PCR with gene specific primers, 5' ZC40285 as shown in SEQ ID NO: 21; and 3' ZC 40286, as shown in SEQ ID NO: 22. The template was cloned human zcytor19 cDNA. (SEQ ID NO: 23) The PCR fragment was gel purified, and ~25 ng was labeled with $P^{32}$ α-dCTP using the Prime-It® RmT random prime labeling kit (Stratagene, LaJolla, Calif.).

The following Northern blots (Clontech, Palo Alto, Calif.) were probed for mRNA expression of zcytor19: (1) a human cancer cell line blot C, which contains RNA samples from each of the following cancer cell lines: promyelocytic leukemia HL-60, HELA S3, chronic myelogenous leukemia k-562, lymphoblastic leukemia MOLT-4, Burkitt's lymphoma RAJI, colorectal adenocarcinoma SW480, lung carcinoma A549, and melanoma G-361; (2) a human MTN H blot, which contains mRNA from the following tissues: heart, whole brain, placenta, lung, liver, skeletal muscle, kidney, and pancreas; (3) a human MTN H3 which contains mRNA from the following tissues: stomach, thyroid, spinal cord, lymph node, trachea, adrenal gland, and bone marrow; and (4) a human MTN H4, which contains mRNA from the following tissues: spleen, thymus, prostate testis, uterus, small intestine, colon, and peripheral blood leukocytes. Hybridizations were all performed in ULTRAhyb™ Ultrasensitive Hybridization Buffer (Ambion, Austin, Tex.) according the manufacturer's recommendations, which the exception that an additional 0.2 mg/ml salmon sperm DNA was added to the hybridization and prehybridization buffers to lower non-specific hybridization. Following hybridization, non-specific radioactive signal was removed by treating the blots with 0.1×SSC/0.5% SDS at 50° C. The blots were exposed using BioMax MR Film and intensifying screens (Eastman Kodak, Rochester, N.Y.), per the manufacturer's recommendations for 3 days.

Expression of a ~4.5 kb transcript was in greatest in heart, skeletal muscle, pancreas and prostate tissue, in addition to in the Burkitt's lymphoma (RAJI) cell line. Lower levels were seen in multiple other tissues. In addition, there was an ~2 kb transcript which was generally less abundant than the larger transcript, but also present in many of the tissues and cell lines. Testis tissue, in addition to having the 2 and 4.5 kb transcripts, may also have ~0.4 kb and 1.4 kb transcripts. Adrenal gland demonstrated equal levels of expression of the 4.5 kb and 2 kb transcripts.

Example 29

Expression of Zcytor19 by In Situ Analysis

Specific human tissues were isolated and screened for zcytor19 expression by in situ hybridization. Various human tissues prepared, sectioned and subjected to in situ hybridization included normal and carcinoma colon, cervical carcinoma, endometrial carcinoma, normal and carcinoma ovary, normal and neoplasmic skin, fetal liver, lung, heart and MFH (muscle sarcoma). The tissues were fixed in 10% buffered formalin and blocked in paraffin using standard techniques. Tissues were sectioned at 4 to 8 microns. Tissues were prepared using a standard protocol. Briefly, tissue sections were deparaffinized with Histo-Clear® (National Diagnostics, Atlanta, Ga.) and then dehydrated with ethanol. Next they were digested with Proteinase K (50 µg/ml) (Boehringer Diagnostics, Indianapolis, Ind.) at 37° C. for 2 to 7 minutes. This step was followed by acetylation and re-hydration of the tissues.

One in situ probe was designed against the human zcytor19 (variant x1) sequence (INC7128744, as shown in SEQ ID NO: 25), containing the 3'UTR of zcytor19 using standard methods. T7 RNA polymerase was used to generate an anti-sense probe. The probe was labeled using an In Vitro transcription System (Riboprobe® in vitro Transcription System, Promega, Madison, Wis.) as per manufacturer's instruction, except that the probes digoxigenin was used instead of radiolabeled rCTP and that the water was adjusted to accommodate the reduced volume of the rNTP's. In situ hybridization was performed with a digoxigenin-labeled zcytor19 probe (above). The probe was added to the slides at a concentration of 1 to 5 pmol/ml for 12 to 16 hours at 60° C. Slides were subsequently washed in 2×SSC and 0.1×SSC at 55° C. The signals were amplified using TSA™ (Tyramide Signal Amplification; PerkinElmer Life Sciences Inc., Boston, Mass.) and visualized with VECTOR Red substrate kit (Vector Laboratories, Burlingame, Calif.) as per manufacturer's instructions. The slides were then counter-stained with hematoxylin.

Signals were observed in several tissues tested: In colon carcinoma tissues, weak signal was observed in carcinoma cells and a few immune infiltrations. However, there was no positive signal observed in the normal colon and intestine, including cells in lamina propria, epithelium, immune nodules and peripheral ganglia nerve cells. In cervical carcinoma tissues, there is weak signal in carcinoma cells and some cells in the immune nodules. In endometrial carcinoma tissues, weak signals present in the carcinoma cells. In normal uterus tissues, no positive signal was observed. In ovarian carcinoma samples, some carcinoma cells are weakly positive. In normal ovary samples, some endothelium of capillaries and epithelium of large follicles may be weakly positive. In the skin carcinoma sample, the cancerous granular epithelium is strongly positive, while no positive signal is observed in the normal skin. In fetal liver, signal is observed in a mixed population of mononuclear cells in sinusoid spaces. In lung, zcytor19 appears to be positive in type II alveolar epithelium. Occasionally bronchial epithelium may also be weakly positive. Macrophage-like mononuclear cells in the interstitial tissue are also positive. In heart, myocytes are negative while some circulating mononuclear cells are positive for zcytor19. In one of the samples, endothelium of the vessels may be weakly positive. Other tissues tested including a MFH (muscle sarcoma) sample and a Kaposi's sarcoma skin sample. There is no conclusive positive signal in these tissues.

Example 30

Human Zcytor19 Expression Based on RT-PCR Analysis of Stimulated Versus Non-Stimulated Cells Gene expression of zcytor19 was examined using RT-PCR analysis of the following cell types: Hela, 293, Daudi, CD14+, U937, and HL-60.

First-strand cDNA synthesis from total RNA was carried out using a commercially available first-strand synthesis system for RT-PCR (Invitrogen life technologies, Carlsbad, Calif.). The subsequent PCR reactions were set up using zcytor19×1 (SEQ ID NO:23) and zcytor19×2 (SEQ ID NO:28) specific oligo primers ZC40288 (SEQ ID NO:58) and ZC40291 (SEQ ID NO:59) which yield a 806 bp and 892 bp product, respectively, Qiagen HotStarTaq DNA Polymerase and Buffer, (Qiagen, Inc., Valencia, Calif.), GeneAmp dNTPs (Applied Biosystems, Foster City, Calif.), RediLoad™ dye (Research Genetics, Inc., Huntville, Ala.) and 2 µl first-strand cDNA (10% of the first-strand reaction) from the respective cell types. The PCR cycler conditions were as follows: an initial 1 cycle 15 minute denaturation at 95° C., 35 cycles of a 45 second denaturation at 94° C., 1 minute annealing at 63° C. and 1 minute and 15 second extension at 72° C., followed by a final 1 cycle extension of 7 minutes at 72° C. The reactions were separated by electrophoresis on a 2% agarose gel (EM Science, Gibbstown, N.J.) and visualized by staining with ethidium bromide.

Bands of the correct size were seen in Hela±IFN-beta (only the 892 bp band), 293+Parental Adv, Daudi IFN-beta, Daudi±IFN-alpha, CD14+ activated, HL-60 activated. No band was observed in CD14+ resting, U937 resting and activated, and HL-60 resting. These results show induction of zcytoR19 expression upon activation or differentiation of monocytes or monocyte cell lines.

Example 31

Stimulation of an NFKB Reporter in Raw Cells

The ability of zcyto20, zcyto21, zcyto22, zcyto24 and zcyto25 to signal through the NF kappa beta signal transduction pathway was tested using a mouse monocyte/macrophage reporter cell line. This cell line was generated by transducing RAW264.7 cells with the KZ170 retroviral reporter containing NF kappa beta response elements driving transcription of a luciferase reporter gene.

Initial reporter assays testing zcyto20, zcyto21, zcyto22, zcyto24 and zcyto25 activity were done using the 293 transient transfected conditioned media described for use in the antiviral assays. RAW264.7/KZ170 cells were harvested and plated at a density of 50,000 cells per well in 96-well plates. The cells were incubated overnight at 37° C. in RPMI+10% FBS. On the following day, media was removed from the adherent cells and undiluted zcyto20-25 conditioned media or dilutions of zcyto20-25 conditioned media (diluted into RPMI+0.1% BSA) were added to the cells. Following a 5-hour incubation at 37° C. the cells were lysed, and read on a luminometer, after addition of a luciferase substrate. The results were analyzed by comparing relative light units (RLU) of zcyto20-25 conditioned media to relative light units of non-transfected cell conditioned media. Undiluted zcyto20-25 conditioned media induced luciferase expression 4-9 fold higher than undiluted non-transfected cell conditioned media. These results indicate that zcyto20-25 are able to signal via the NF kappa beta signaling pathway in a mouse monocyte/macrophage cell line.

As a follow up, conditioned media from Sf9 cells infected with baculovirus expressing zcyto20, zcyto21 or zcyto22 were used in the reporter assays. Wild type baculovirus was used as a negative control. The production of the baculovirus constructs and conditioned media was described above.

The results of the RAW264.7 NFkb-reporter assay using the baculovirus-derived conditioned media were similar to that using the 293 transient transfected conditioned media. Baculovirus-derived conditioned media containing zcyto20-22 induced luciferase expression in a dose dependent manner, while the corresponding control conditioned medium did not.

Example 32

In Vivo Results

The toxicity and biological activity of zcyto24 was compared to another Class II cytokine, and a parental adenovirus vector, as well as in non-injected mice. Four groups of 8 C57B16 mice (female, 9 weeks of age) were injected as follows:

Group 1: Injected with Adzcyto24 at $1 \times 10^{11}$ particles per mouse;

Group 2: Injected with a Class II cytokine (Adzcyto) at $1 \times 10^{11}$ particles;

Group 3: Parental adenovirus vector (Adzpar) at $1 \times 10^{11}$ particles; and Group 4: Untreated Temperature transponders were placed on the mice on Day −1, and virus was injected Day 0. Cage-wise food intake and body weight were monitored every 5 Days, and blood was sampled on Day 10 (0.25 ml max) for assays including CBC and Abbot blood analyzer. All mice were sacrificed on Day 20.

Adzcyto24 (Group 1) treated mice were bled at Day 10 and the sera were tested for the presence of zcyto24 bioactivity. A viral assay demonstrated significant antiviral activity at a maximal dilution of 1:500 for each and every mouse in the Adzcyto24 group. This corresponds to approximately 160 ng/ml of purified zcyto24CEE. An antiviral assay to detect mouse interferons detected no activity in the Adzcyto24 group. A bioassay using a reporter with an ISRE also detected significant zcyto24 activity in the sera of the Adzcyto24 injected mice but not the other groups.

Temperature probes revealed that the mean body temperature for Group 2 decreased by more than 5 degrees C. by Day 10 while the mean temp for the Adzcyto24 (Group 1) group had decreased by more than 2 degrees C. Control groups displayed less than a 1 degree change in temperature throughout the experiment.

The Adzcyto24 (Group 1) mice displayed a slight increase in weight during the 20 Day experiment, equivalent to the control groups (Groups 3 and 4). Group 2 mice lost weight: The mean weight for Group 2 decreased by ~8% by Day 10.

Abbot blood analyzer analysis of blood obtained on Day 10 and Day 20 revealed significant changes in the leukocyte counts in Groups 1 and 2. Group 1 shows a pronounced increase in monocyte counts in Adzcyto24 treated mice relative to the other groups. Monocyte counts are 2.77 times higher in Adzcyto24 injected mice versus parental vector (Adzpar) injected mice. By Day 20 monocyte counts decreased somewhat, but were still significantly elevated relative to the parental vector injected mice. Group 2 shows that injection with adenovirus encoding a Class II cytokine (Adzcyto) but not with an adenovirus encoding zcyto24 leads to increased neutrophil counts on Day 10.

To verify the identity of the cell types detected by the Abbot blood analyzer flow cytometry was performed with lineage-specific MAbs on blood from Day 20 of the experiment. Figure 3 shows the % of CD11b positive cells, i.e. monocytes in the peripheral blood of each mouse. Plotting the mean values for each group, Figure 4 reveals a significant increase in the percent of monocytes in the group injected with adenovirus infected with Zycyto24 versus the group infected with parental vector ($p=0.05$) This correlates with the changes previously observed with the Abbot blood analyzer.

Analysis of the same blood samples with a MAb specific for granulocytes (GR-1) revealed no significant increase in the percentage of granulocytes (i.e. primarily neutrophils) for the Adzcyto24 injected mice. The PBL were also stained with MAbs specific to B cells (B220) and no significant differences were observed in the Adzcyto24 injected mice relative to the other groups.

Notably the chills and weight loss associated with Adzcyto injection were not evident with Adzcyto24. The apparent elevation in monocytes detected by the Abbot blood analyzer at Days 10 and 20 were confirmed by flow cytometry of Day 20 blood with lineage-specific MAbs. A distinct increase in the percentage of monocytes in the PBL of mice injected with Adzcyto24 appears to be a unique activity either directly or indirectly mediated by zcyto24 in the context of an adenoviral infection. Zcyto24 expressed at significant levels in the Adzcyto24 injected mice is likely promoting an antiviral response by either recruiting and mobilizing monocytes from peripheral tissues or by stimulating production of monocytes from bone marrow or liver derived progenitor cells. This evidence suggests that monocytes/macrophages are activated by zcyto24 and zcyto21.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of inducing 2-5 oligoadenylate synthetase in a mammal comprising administering to the mammal an effective amount of a polypeptide comprising an amino acid sequence having at least 95% sequence identity with amino acid residues 20-200 of SEQ ID NO:5, wherein the polypeptide induces 2-5 oligoadenylate synthetase expression in the mammal.

2. The method of claim 1, wherein the polypeptide is pegylated.

3. A method of inducing 2-5 oligoadenylate synthetase in a mammal comprising administering to the mammal an effective amount of a composition comprising a polypeptide comprising an amino acid sequence having at least 95% sequence identity with amino acid residues 20-200 of SEQ ID NO:5 and a pharmaceutically acceptable vehicle, wherein the composition induces 2-5 oligoadenylate synthetase expression in the mammal.

4. The method of claim 3, wherein the polypeptide is pegylated.

* * * * *

UNITED STATES PATENT AND TRADEMARK OFFICE
CERTIFICATE OF CORRECTION

PATENT NO. : 8,231,866 B2
APPLICATION NO. : 13/353524
DATED : July 31, 2012
INVENTOR(S) : Paul Sheppard et al.

Page 1 of 1

It is certified that error appears in the above-identified patent and that said Letters Patent is hereby corrected as shown below:

First Page

In the Abstract, column 2, line 2, delete "zycto24", and insert --zcyto24--, therefor.

Signed and Sealed this
Fourth Day of December, 2012

David J. Kappos
*Director of the United States Patent and Trademark Office*

SEQUENCE LISTING

<160> NUMBER OF SEQ ID NOS: 59

<210> SEQ ID NO 1
<211> LENGTH: 618
<212> TYPE: DNA
<213> ORGANISM: Homo sapiens
<220> FEATURE:

<221> NAME/KEY: CDS
<222> LOCATION: (1)...(618)

<400> SEQUENCE: 1

| | | | | | | | | | | | | | | | | |
|---|---|---|---|---|---|---|---|---|---|---|---|---|---|---|---|---|
| atg | act | ggg | gac | tgc | acg | cca | gtg | ctg | gtg | ctg | atg | gcc | gca | gtg | ctg | 48 |
| Met | Thr | Gly | Asp | Cys | Thr | Pro | Val | Leu | Val | Leu | Met | Ala | Ala | Val | Leu | |
| 1 | | | | 5 | | | | | 10 | | | | | 15 | | |
| acc | gtg | act | gga | gca | gtt | cct | gtc | gcc | agg | ctc | cac | ggg | gct | ctc | ccg | 96 |
| Thr | Val | Thr | Gly | Ala | Val | Pro | Val | Ala | Arg | Leu | His | Gly | Ala | Leu | Pro | |
| | | 20 | | | | | 25 | | | | | 30 | | | | |
| gat | gca | agg | ggc | tgc | cac | ata | gcc | cag | ttc | aag | tcc | ctg | tct | cca | cag | 144 |
| Asp | Ala | Arg | Gly | Cys | His | Ile | Ala | Gln | Phe | Lys | Ser | Leu | Ser | Pro | Gln | |
| | 35 | | | | | 40 | | | | | 45 | | | | | |
| gag | ctg | cag | gcc | ttt | aag | agg | gcc | aaa | gat | gcc | tta | gaa | gag | tcg | ctt | 192 |
| Glu | Leu | Gln | Ala | Phe | Lys | Arg | Ala | Lys | Asp | Ala | Leu | Glu | Glu | Ser | Leu | |
| 50 | | | | | 55 | | | | | 60 | | | | | | |
| ctg | ctg | aag | gac | tgc | agg | tgc | cac | tcc | cgc | ctc | ttc | ccc | agg | acc | tgg | 240 |
| Leu | Leu | Lys | Asp | Cys | Arg | Cys | His | Ser | Arg | Leu | Phe | Pro | Arg | Thr | Trp | |
| 65 | | | | 70 | | | | | 75 | | | | | 80 | | |
| gac | ctg | agg | cag | ctg | cag | gtg | agg | gag | cgc | ccc | atg | gct | ttg | gag | gct | 288 |
| Asp | Leu | Arg | Gln | Leu | Gln | Val | Arg | Glu | Arg | Pro | Met | Ala | Leu | Glu | Ala | |
| | | | | 85 | | | | | 90 | | | | | 95 | | |
| gag | ctg | gcc | ctg | acg | ctg | aag | gtt | ctg | gag | gcc | acc | gct | gac | act | gac | 336 |
| Glu | Leu | Ala | Leu | Thr | Leu | Lys | Val | Leu | Glu | Ala | Thr | Ala | Asp | Thr | Asp | |
| | | | 100 | | | | | 105 | | | | | 110 | | | |
| cca | gcc | ctg | gtg | gac | gtc | ttg | gac | cag | ccc | ctt | cac | acc | ctg | cac | cat | 384 |
| Pro | Ala | Leu | Val | Asp | Val | Leu | Asp | Gln | Pro | Leu | His | Thr | Leu | His | His | |
| | | 115 | | | | | 120 | | | | | 125 | | | | |
| atc | ctc | tcc | cag | ttc | cgg | gcc | tgt | gtg | agt | cgt | cag | ggc | ctg | ggc | acc | 432 |
| Ile | Leu | Ser | Gln | Phe | Arg | Ala | Cys | Val | Ser | Arg | Gln | Gly | Leu | Gly | Thr | |
| | 130 | | | | | 135 | | | | | 140 | | | | | |
| cag | atc | cag | cct | cag | ccc | acg | gca | ggg | ccc | agg | acc | cgg | ggc | cgc | ctc | 480 |
| Gln | Ile | Gln | Pro | Gln | Pro | Thr | Ala | Gly | Pro | Arg | Thr | Arg | Gly | Arg | Leu | |
| 145 | | | | | 150 | | | | | 155 | | | | | 160 | |
| cac | cat | tgg | ctg | tac | cgg | ctc | cag | gag | gcc | cca | aaa | aag | gag | tcc | cct | 528 |
| His | His | Trp | Leu | Tyr | Arg | Leu | Gln | Glu | Ala | Pro | Lys | Lys | Glu | Ser | Pro | |
| | | | | 165 | | | | | 170 | | | | | 175 | | |
| ggc | tgc | ctc | gag | gcc | tct | gtc | acc | ttc | aac | ctc | ttc | cgc | ctc | ctc | acg | 576 |
| Gly | Cys | Leu | Glu | Ala | Ser | Val | Thr | Phe | Asn | Leu | Phe | Arg | Leu | Leu | Thr | |
| | | | 180 | | | | | 185 | | | | | 190 | | | |
| cga | gac | ctg | aat | tgt | gtt | gcc | agt | ggg | gac | ctg | tgt | gtc | tga | | | 618 |
| Arg | Asp | Leu | Asn | Cys | Val | Ala | Ser | Gly | Asp | Leu | Cys | Val | * | | | |
| | | | 195 | | | | | 200 | | | | | 205 | | | |

<210> SEQ ID NO 2
<211> LENGTH: 205
<212> TYPE: PRT
<213> ORGANISM: Homo sapiens

<400> SEQUENCE: 2

Met Thr Gly Asp Cys Thr Pro Val Leu Val Leu Met Ala Ala Val Leu
1               5                   10                  15

Thr Val Thr Gly Ala Val Pro Val Ala Arg Leu His Gly Ala Leu Pro
            20                  25                  30

Asp Ala Arg Gly Cys His Ile Ala Gln Phe Lys Ser Leu Ser Pro Gln
        35                  40                  45

Glu Leu Gln Ala Phe Lys Arg Ala Lys Asp Ala Leu Glu Glu Ser Leu
    50                  55                  60

Leu Leu Lys Asp Cys Arg Cys His Ser Arg Leu Phe Pro Arg Thr Trp
65                  70                  75                  80

```
Asp Leu Arg Gln Leu Gln Val Arg Glu Arg Pro Met Ala Leu Glu Ala
                85                  90                  95

Glu Leu Ala Leu Thr Leu Lys Val Leu Glu Ala Thr Ala Asp Thr Asp
            100                 105                 110

Pro Ala Leu Val Asp Val Leu Asp Gln Pro Leu His Thr Leu His His
        115                 120                 125

Ile Leu Ser Gln Phe Arg Ala Cys Val Ser Arg Gln Gly Leu Gly Thr
    130                 135                 140

Gln Ile Gln Pro Gln Pro Thr Ala Gly Pro Arg Thr Arg Gly Arg Leu
145                 150                 155                 160

His His Trp Leu Tyr Arg Leu Gln Glu Ala Pro Lys Lys Glu Ser Pro
                165                 170                 175

Gly Cys Leu Glu Ala Ser Val Thr Phe Asn Leu Phe Arg Leu Leu Thr
            180                 185                 190

Arg Asp Leu Asn Cys Val Ala Ser Gly Asp Leu Cys Val
        195                 200                 205

<210> SEQ ID NO 3
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A, T, C or G

<400> SEQUENCE: 3
atgacngghg aytgyacncc ngtnytngtn ytnatggcng cngtnytnac ngtnacnggn     60
gcngtnccng tngcnmgnyt ncayggngcn ytnccngayg cnmgnggntg ycayathgcn    120
carttyaarw snytnwsncc ncargarytn cargcnttya armgncnaaa rgaygcnytn    180
gargarwsny tnytnytnaa rgaytgymgn tgycaywsnm gnytnttycc nmgnacntgg    240
gayytnmgnc arytncargt nmgngarmgn ccnatggcny tngargcnga rytngcnytn    300
acnytnaarg tnytngargc nacngcngay acngayccng cnytngtnga ygtnytngay    360
carccnytnc ayacnytnca ycayathytn wsncarttym gngcntgygt nwsnmgncar    420
ggnytnggna cncarathca rccncarccn acngcnggnc cnmgnacnmg nggnmgnytn    480
caycaytggy tntaymgnyt ncargargcn ccnaaraarg arwsnccngg ntgyytngar    540
gcnwsngtna cnttyaayyt nttymgnytn ytnacnmgng ayytnaaytg ygtngcnwsn    600
ggngayytnt gygtn                                                     615

<210> SEQ ID NO 4
<211> LENGTH: 603
<212> TYPE: DNA
<213> ORGANISM: Homo sapiens
<220> FEATURE:
<221> NAME/KEY: CDS
<222> LOCATION: (1)...(603)

<400> SEQUENCE: 4 atg gct gca gct tgg acc gtg gtg ctg gtg act ttg gtg cta ggc ttg      48
Met Ala Ala Ala Trp Thr Val Val Leu Val Thr Leu Val Leu Gly Leu
 1               5                  10                  15 gcc gtg gca ggc cct gtc ccc act tcc aag ccc acc aca act ggg aag      96
Ala Val Ala Gly Pro Val Pro Thr Ser Lys Pro Thr Thr Thr Gly Lys
             20                  25                  30 ggc tgc cac att ggc agg ttc aaa tct ctg tca cca cag gag cta gcg     144
Gly Cys His Ile Gly Arg Phe Lys Ser Leu Ser Pro Gln Glu Leu Ala
         35                  40                  45
```

```
agc ttc aag aag gcc agg gac gcc ttg gaa gag tca ctc aag ctg aaa    192
Ser Phe Lys Lys Ala Arg Asp Ala Leu Glu Glu Ser Leu Lys Leu Lys
    50                  55                  60 aac tgg agt tgc agc tct cct gtc ttc ccc ggg aat tgg gac ctg agg    240
Asn Trp Ser Cys Ser Ser Pro Val Phe Pro Gly Asn Trp Asp Leu Arg
65                  70                  75                  80 ctt ctc cag gtg agg gag cgc cct gtg gcc ttg gag gct gag ctg gcc    288
Leu Leu Gln Val Arg Glu Arg Pro Val Ala Leu Glu Ala Glu Leu Ala
                85                  90                  95 ctg acg ctg aag gtc ctg gag gcc gct gct ggc cca gcc ctg gag gac    336
Leu Thr Leu Lys Val Leu Glu Ala Ala Ala Gly Pro Ala Leu Glu Asp
            100                 105                 110 gtc cta gac cag ccc ctt cac acc ctg cac cac atc ctc tcc cag ctc    384
Val Leu Asp Gln Pro Leu His Thr Leu His His Ile Leu Ser Gln Leu
        115                 120                 125 cag gcc tgt atc cag cct cag ccc aca gca ggg ccc agg ccc cgg ggc    432
Gln Ala Cys Ile Gln Pro Gln Pro Thr Ala Gly Pro Arg Pro Arg Gly
    130                 135                 140 cgc ctc cac cac tgg ctg cac cgg ctc cag gag gcc ccc aaa aag gag    480
Arg Leu His His Trp Leu His Arg Leu Gln Glu Ala Pro Lys Lys Glu
145                 150                 155                 160 tcc gct ggc tgc ctg gag gca tct gtc acc ttc aac ctc ttc cgc ctc    528
Ser Ala Gly Cys Leu Glu Ala Ser Val Thr Phe Asn Leu Phe Arg Leu
                165                 170                 175 ctc acg cga gac ctc aaa tat gtg gcc gat ggg gac ctg tgt ctg aga    576
Leu Thr Arg Asp Leu Lys Tyr Val Ala Asp Gly Asp Leu Cys Leu Arg
            180                 185                 190 acg tca acc cac cct gag tcc acc tga                                603
Thr Ser Thr His Pro Glu Ser Thr *
        195                 200

<210> SEQ ID NO 5
<211> LENGTH: 200
<212> TYPE: PRT
<213> ORGANISM: Homo sapiens

<400> SEQUENCE: 5

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
        115                 120                 125

Gln Ala Cys Ile Gln Pro Gln Pro Thr Ala Gly Pro Arg Pro Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
```

```
                        165                 170                 175
Leu Thr Arg Asp Leu Lys Tyr Val Ala Asp Gly Asp Leu Cys Leu Arg
        180                 185                 190

Thr Ser Thr His Pro Glu Ser Thr
        195                 200

<210> SEQ ID NO 6
<211> LENGTH: 615
<212> TYPE: DNA
<213> ORGANISM: Homo sapiens
<220> FEATURE:
<221> NAME/KEY: CDS
<222> LOCATION: (1)...(615)

<400> SEQUENCE: 6 atg acc ggg gac tgc atg cca gtg ctg gtg ctg atg gcc gca gtg ctg      48
Met Thr Gly Asp Cys Met Pro Val Leu Val Leu Met Ala Ala Val Leu
  1               5                  10                  15 acc gtg act gga gca gtt cct gtc gcc agg ctc cgc ggg gct ctc ccg      96
Thr Val Thr Gly Ala Val Pro Val Ala Arg Leu Arg Gly Ala Leu Pro
             20                  25                  30 gat gca agg ggc tgc cac ata gcc cag ttc aag tcc ctg tct cca cag     144
Asp Ala Arg Gly Cys His Ile Ala Gln Phe Lys Ser Leu Ser Pro Gln
         35                  40                  45 gag ctg cag gcc ttt aag agg gcc aaa gat gcc tta gaa gag tcg ctt     192
Glu Leu Gln Ala Phe Lys Arg Ala Lys Asp Ala Leu Glu Glu Ser Leu
     50                  55                  60 ctg ctg aag gac tgc aag tgc cgc tcc cgc ctc ttc ccc agg acc tgg     240
Leu Leu Lys Asp Cys Lys Cys Arg Ser Arg Leu Phe Pro Arg Thr Trp
 65                  70                  75                  80 gac ctg agg cag ctg cag gtg agg gag cgc ccc gtg gct ttg gag gct     288
Asp Leu Arg Gln Leu Gln Val Arg Glu Arg Pro Val Ala Leu Glu Ala
                 85                  90                  95 gag ctg gcc ctg acg ctg aag gtt ctg gag gcc acc gct gac act gac     336
Glu Leu Ala Leu Thr Leu Lys Val Leu Glu Ala Thr Ala Asp Thr Asp
            100                 105                 110 cca gcc ctg ggg gat gtc ttg gac cag ccc ctt cac acc ctg cac cat     384
Pro Ala Leu Gly Asp Val Leu Asp Gln Pro Leu His Thr Leu His His
        115                 120                 125 atc ctc tcc cag ctc cgg gcc tgt gtg agt cgt cag ggc ccg ggc acc     432
Ile Leu Ser Gln Leu Arg Ala Cys Val Ser Arg Gln Gly Pro Gly Thr
    130                 135                 140 cag atc cag cct cag ccc acg gca ggg ccc agg acc cgg ggc cgc ctc     480
Gln Ile Gln Pro Gln Pro Thr Ala Gly Pro Arg Thr Arg Gly Arg Leu
145                 150                 155                 160 cac cat tgg ctg cac cgg ctc cag gag gcc cca aaa aag gag tcc cct     528
His His Trp Leu His Arg Leu Gln Glu Ala Pro Lys Lys Glu Ser Pro
                165                 170                 175 ggc tgc ctc gag gcc tct gtc acc ttc aac ctc ttc cgc ctc ctc acg     576
Gly Cys Leu Glu Ala Ser Val Thr Phe Asn Leu Phe Arg Leu Leu Thr
            180                 185                 190 cga gac ctg aat tgt gtt gcc agc ggg gac ctg tgt gtc                 615
Arg Asp Leu Asn Cys Val Ala Ser Gly Asp Leu Cys Val
        195                 200                 205

<210> SEQ ID NO 7
<211> LENGTH: 205
<212> TYPE: PRT
<213> ORGANISM: Homo sapiens

<400> SEQUENCE: 7

Met Thr Gly Asp Cys Met Pro Val Leu Val Leu Met Ala Ala Val Leu
```

```
                1               5              10              15
        Thr Val Thr Gly Ala Val Pro Val Ala Arg Leu Arg Gly Ala Leu Pro
                        20                  25                  30

Asp Ala Arg Gly Cys His Ile Ala Gln Phe Lys Ser Leu Ser Pro Gln
                        35                  40                  45

Glu Leu Gln Ala Phe Lys Arg Ala Lys Asp Ala Leu Glu Glu Ser Leu
                    50                  55                  60

Leu Leu Lys Asp Cys Lys Cys Arg Ser Arg Leu Phe Pro Arg Thr Trp
        65                  70                  75                  80

Asp Leu Arg Gln Leu Gln Val Arg Glu Arg Pro Val Ala Leu Glu Ala
                        85                  90                  95

Glu Leu Ala Leu Thr Leu Lys Val Leu Glu Ala Thr Ala Asp Thr Asp
                        100                 105                 110

Pro Ala Leu Gly Asp Val Leu Asp Gln Pro Leu His Thr Leu His His
                    115                 120                 125

Ile Leu Ser Gln Leu Arg Ala Cys Val Ser Arg Gln Gly Pro Gly Thr
                    130                 135                 140

Gln Ile Gln Pro Gln Pro Thr Ala Gly Pro Arg Thr Arg Gly Arg Leu
        145                 150                 155                 160

His His Trp Leu His Arg Leu Gln Glu Ala Pro Lys Lys Glu Ser Pro
                        165                 170                 175

Gly Cys Leu Glu Ala Ser Val Thr Phe Asn Leu Phe Arg Leu Leu Thr
                        180                 185                 190

Arg Asp Leu Asn Cys Val Ala Ser Gly Asp Leu Cys Val
                    195                 200                 205

<210> SEQ ID NO 8
        <211> LENGTH: 633
        <212> TYPE: DNA
        <213> ORGANISM: Homo sapiens
        <220> FEATURE:
        <221> NAME/KEY: CDS
        <222> LOCATION: (22)...(630)

<400> SEQUENCE: 8
tcacagaccc cggagagcaa c atg aag cca gaa aca gct ggg ggc cac atg      51
                                Met Lys Pro Glu Thr Ala Gly Gly His Met
                                  1               5                  10 ctc ctc ctg ctg ttg cct ctg ctg ctg gcc gca gtg ctg aca aga acc     99
        Leu Leu Leu Leu Leu Pro Leu Leu Leu Ala Ala Val Leu Thr Arg Thr
                        15                  20                  25 caa gct gac cct gtc ccc agg gcc acc agg ctc cca gtg gaa gca aag    147
        Gln Ala Asp Pro Val Pro Arg Ala Thr Arg Leu Pro Val Glu Ala Lys
                    30                  35                  40 gat tgc cac att gct cag ttc aag tct ctg tcc cca aaa gag ctg cag    195
        Asp Cys His Ile Ala Gln Phe Lys Ser Leu Ser Pro Lys Glu Leu Gln
                    45                  50                  55 gcc ttc aaa aag gcc aag gat gcc atc gag aag agg ctg ctt gag aag    243
        Ala Phe Lys Lys Ala Lys Asp Ala Ile Glu Lys Arg Leu Leu Glu Lys
                60                  65                  70 gac ctg agg tgc agt tcc cac ctc ttc ccc agg gcc tgg gac ctg aag    291
        Asp Leu Arg Cys Ser Ser His Leu Phe Pro Arg Ala Trp Asp Leu Lys
        75                  80                  85                  90 cag ctg cag gtc caa gag cgc ccc aag gcc ttg cag gct gag gtg gcc    339
        Gln Leu Gln Val Gln Glu Arg Pro Lys Ala Leu Gln Ala Glu Val Ala
                        95                 100                 105 ctg acc ctg aag gtc tgg gag aac atg act gac tca gcc ctg gcc acc    387
        Leu Thr Leu Lys Val Trp Glu Asn Met Thr Asp Ser Ala Leu Ala Thr
                    110                 115                 120
```

```
atc ctg ggc cag cct ctt cat aca ctg agc cac att cac tcc cag ctg    435
Ile Leu Gly Gln Pro Leu His Thr Leu Ser His Ile His Ser Gln Leu
        125                 130                 135 cag acc tgt aca cag ctt cag gcc aca gca gag ccc agg tcc ccg agc    483
Gln Thr Cys Thr Gln Leu Gln Ala Thr Ala Glu Pro Arg Ser Pro Ser
140                 145                 150 cgc cgc ctc tcc cgc tgg ctg cac agg ctc cag gag gcc cag agc aag    531
Arg Arg Leu Ser Arg Trp Leu His Arg Leu Gln Glu Ala Gln Ser Lys
155                 160                 165                 170 gag acc cct ggc tgc ctg gag gcc tct gtc acc tcc aac ctg ttt cgc    579
Glu Thr Pro Gly Cys Leu Glu Ala Ser Val Thr Ser Asn Leu Phe Arg
            175                 180                 185 ctg ctc acc cgg gac ctc aag tgt gtg gcc aat gga gac cag tgt gtc    627
Leu Leu Thr Arg Asp Leu Lys Cys Val Ala Asn Gly Asp Gln Cys Val
        190                 195                 200 tga cct                                                              633
*
```

<210> SEQ ID NO 9
<211> LENGTH: 202
<212> TYPE: PRT
<213> ORGANISM: Homo sapiens

<400> SEQUENCE: 9

```
Met Lys Pro Glu Thr Ala Gly Gly His Met Leu Leu Leu Leu Pro
 1               5                  10                  15

Leu Leu Leu Ala Ala Val Leu Thr Arg Thr Gln Ala Asp Pro Val Pro
             20                  25                  30

Arg Ala Thr Arg Leu Pro Val Glu Ala Lys Asp Cys His Ile Ala Gln
         35                  40                  45

Phe Lys Ser Leu Ser Pro Lys Glu Leu Gln Ala Phe Lys Lys Ala Lys
     50                  55                  60

Asp Ala Ile Glu Lys Arg Leu Glu Lys Asp Leu Arg Cys Ser Ser
 65                  70                  75                  80

His Leu Phe Pro Arg Ala Trp Asp Leu Lys Gln Leu Gln Val Gln Glu
                 85                  90                  95

Arg Pro Lys Ala Leu Gln Ala Glu Val Ala Leu Thr Leu Lys Val Trp
             100                 105                 110

Glu Asn Met Thr Asp Ser Ala Leu Ala Thr Ile Leu Gly Gln Pro Leu
         115                 120                 125

His Thr Leu Ser His Ile His Ser Gln Leu Gln Thr Cys Thr Gln Leu
     130                 135                 140

Gln Ala Thr Ala Glu Pro Arg Ser Pro Ser Arg Arg Leu Ser Arg Trp
145                 150                 155                 160

Leu His Arg Leu Gln Glu Ala Gln Ser Lys Glu Thr Pro Gly Cys Leu
                 165                 170                 175

Glu Ala Ser Val Thr Ser Asn Leu Phe Arg Leu Leu Thr Arg Asp Leu
             180                 185                 190

Lys Cys Val Ala Asn Gly Asp Gln Cys Val
         195                 200
```

<210> SEQ ID NO 10
<211> LENGTH: 632
<212> TYPE: DNA
<213> ORGANISM: Homo sapiens
<220> FEATURE:
<221> NAME/KEY: CDS
<222> LOCATION: (22)...(630)

<400> SEQUENCE: 10

```
tcacagaccc cggagagcaa c atg aag cca gaa aca gct ggg ggc cac atg           51
                        Met Lys Pro Glu Thr Ala Gly Gly His Met
                         1               5                  10 ctc ctc ctg ctg ttg cct ctg ctg ctg gcc gca gtg ctg aca aga acc           99
Leu Leu Leu Leu Leu Pro Leu Leu Leu Ala Ala Val Leu Thr Arg Thr
                 15                  20                  25 caa gct gac cct gtc ccc agg gcc acc agg ctc cca gtg gaa gca aag          147
Gln Ala Asp Pro Val Pro Arg Ala Thr Arg Leu Pro Val Glu Ala Lys
             30                  35                  40 gat tgc cac att gct cag ttc aag tct ctg tcc cca aaa gag ctg cag          195
Asp Cys His Ile Ala Gln Phe Lys Ser Leu Ser Pro Lys Glu Leu Gln
         45                  50                  55 gcc ttc aaa aag gcc aag ggt gcc atc gag aag agg ctg ctt gag aag          243
Ala Phe Lys Lys Ala Lys Gly Ala Ile Glu Lys Arg Leu Leu Glu Lys
     60                  65                  70 gac atg agg tgc agt tcc cac ctc atc tcc agg gcc tgg gac ctg aag          291
Asp Met Arg Cys Ser Ser His Leu Ile Ser Arg Ala Trp Asp Leu Lys
 75                  80                  85                  90 cag ctg cag gtc caa gag cgc ccc aag gcc ttg cag gct gag gtg gcc          339
Gln Leu Gln Val Gln Glu Arg Pro Lys Ala Leu Gln Ala Glu Val Ala
                 95                 100                 105 ctg acc ctg aag gtc tgg gag aac ata aat gac tca gcc ctg acc acc          387
Leu Thr Leu Lys Val Trp Glu Asn Ile Asn Asp Ser Ala Leu Thr Thr
            110                 115                 120 atc ctg ggc cag cct ctt cat aca ctg agc cac att cac tcc cag ctg          435
Ile Leu Gly Gln Pro Leu His Thr Leu Ser His Ile His Ser Gln Leu
            125                 130                 135 cag acc tgt aca cag ctt cag gcc aca gca gag ccc aag ccc ccg agt          483
Gln Thr Cys Thr Gln Leu Gln Ala Thr Ala Glu Pro Lys Pro Pro Ser
        140                 145                 150 cgc cgc ctc tcc cgc tgg ctg cac agg ctc cag gag gcc cag agc aag          531
Arg Arg Leu Ser Arg Trp Leu His Arg Leu Gln Glu Ala Gln Ser Lys
155                 160                 165                 170 gag act cct ggc tgc ctg gag gac tct gtc acc tcc aac ctg ttt caa          579
Glu Thr Pro Gly Cys Leu Glu Asp Ser Val Thr Ser Asn Leu Phe Gln
                175                 180                 185 ctg ctc ctc cgg gac ctc aag tgt gtg gcc agt gga gac cag tgt gtc          627
Leu Leu Leu Arg Asp Leu Lys Cys Val Ala Ser Gly Asp Gln Cys Val
            190                 195                 200 tga cc                                                                   632
 *
```

<210> SEQ ID NO 11
<211> LENGTH: 202
<212> TYPE: PRT
<213> ORGANISM: Homo sapiens

<400> SEQUENCE: 11

```
Met Lys Pro Glu Thr Ala Gly Gly His Met Leu Leu Leu Leu Leu Pro
 1               5                  10                  15

Leu Leu Leu Ala Ala Val Leu Thr Arg Thr Gln Ala Asp Pro Val Pro
             20                  25                  30

Arg Ala Thr Arg Leu Pro Val Glu Ala Lys Asp Cys His Ile Ala Gln
         35                  40                  45

Phe Lys Ser Leu Ser Pro Lys Glu Leu Gln Ala Phe Lys Lys Ala Lys
     50                  55                  60

Gly Ala Ile Glu Lys Arg Leu Leu Glu Lys Asp Met Arg Cys Ser Ser
 65                  70                  75                  80
```

```
His Leu Ile Ser Arg Ala Trp Asp Leu Lys Gln Leu Gln Val Gln Glu
            85                  90                  95

Arg Pro Lys Ala Leu Gln Ala Glu Val Ala Leu Thr Leu Lys Val Trp
        100                 105                 110

Glu Asn Ile Asn Asp Ser Ala Leu Thr Thr Ile Leu Gly Gln Pro Leu
        115                 120                 125

His Thr Leu Ser His Ile His Ser Gln Leu Gln Thr Cys Thr Gln Leu
    130                 135                 140

Gln Ala Thr Ala Glu Pro Lys Pro Pro Ser Arg Arg Leu Ser Arg Trp
145                 150                 155                 160

Leu His Arg Leu Gln Glu Ala Gln Ser Lys Glu Thr Pro Gly Cys Leu
                165                 170                 175

Glu Asp Ser Val Thr Ser Asn Leu Phe Gln Leu Leu Leu Arg Asp Leu
            180                 185                 190

Lys Cys Val Ala Ser Gly Asp Gln Cys Val
            195                 200

<210> SEQ ID NO 12
<211> LENGTH: 49
<212> TYPE: DNA
<213> ORGANISM: Artificial Sequence
<220> FEATURE:
<223> OTHER INFORMATION: oligonucleotide primer ZC40923

<400> SEQUENCE: 12
tccagggaat tcatataggc cggccaccat gaaactagac atgactggg              49

<210> SEQ ID NO 13
<211> LENGTH: 88
<212> TYPE: DNA
<213> ORGANISM: Artificial Sequence
<220> FEATURE:
<223> OTHER INFORMATION: oligonucleotide primer ZC40927

<400> SEQUENCE: 13
caacccagga gctgttttaa ggcgcgcctc tagactattt ttagtccatc ggcatgtatt   60
ctccagagac acacaggtcc ccactggc                                      88

<210> SEQ ID NO 14
<211> LENGTH: 42
<212> TYPE: DNA
<213> ORGANISM: Artificial Sequence
<220> FEATURE:
<223> OTHER INFORMATION: oligonucleotide primer ZC41932

<400> SEQUENCE: 14
atgcattcta gactagacac acaggtcccc actggcaaca ca                      42

<210> SEQ ID NO 15
<211> LENGTH: 42
<212> TYPE: DNA
<213> ORGANISM: Artificial Sequence
<220> FEATURE:
<223> OTHER INFORMATION: oligonucleotide primer ZC41933

<400> SEQUENCE: 15
atgcattcta gactagacac acaggtcccc actggcaaca ca                      42

<210> SEQ ID NO 16
<211> LENGTH: 5
<212> TYPE: PRT
<213> ORGANISM: Artificial Sequence
<220> FEATURE:
```

<223> OTHER INFORMATION: glu glu tag

<400> SEQUENCE: 16

Glu Tyr Pro Met Glu
 1               5

<210> SEQ ID NO 17
<211> LENGTH: 36
<212> TYPE: DNA
<213> ORGANISM: Artificial Sequence
<220> FEATURE:
<223> OTHER INFORMATION: oligonucleotide primer ZC40240

<400> SEQUENCE: 17
atgcatggat ccatgaaact agacatgact ggggac                            36

<210> SEQ ID NO 18
<211> LENGTH: 36
<212> TYPE: DNA
<213> ORGANISM: Artificial Sequence
<220> FEATURE:
<223> OTHER INFORMATION: oligonucleotide primer ZC40241

<400> SEQUENCE: 18
atgcattcta gagcgacaca caggtcccca ctggca                            36

<210> SEQ ID NO 19
<211> LENGTH: 17
<212> TYPE: DNA
<213> ORGANISM: Artificial Sequence
<220> FEATURE:
<223> OTHER INFORMATION: oligonucleotide primer ZC447

<400> SEQUENCE: 19
taacaatttc acacagg                                                 17

<210> SEQ ID NO 20
<211> LENGTH: 18
<212> TYPE: DNA
<213> ORGANISM: Artificial Sequence
<220> FEATURE:
<223> OTHER INFORMATION: oligonucleotide primer ZC976

<400> SEQUENCE: 20
cgttgtaaaa cgacggcc                                                18

<210> SEQ ID NO 21
<211> LENGTH: 24
<212> TYPE: DNA
<213> ORGANISM: Artificial Sequence
<220> FEATURE:
<223> OTHER INFORMATION: oligonucleotide primer ZC40285

<400> SEQUENCE: 21
gccccagcca cccaacagac aaga                                         24

<210> SEQ ID NO 22
<211> LENGTH: 24
<212> TYPE: DNA
<213> ORGANISM: Artificial Sequence
<220> FEATURE:
<223> OTHER INFORMATION: oligonucleotide primer ZC40286

<400> SEQUENCE: 22
ccaggtggcc caggaggaga ggtt                                         24

<210> SEQ ID NO 23
<211> LENGTH: 1476
<212> TYPE: DNA
<213> ORGANISM: Homo sapiens
<220> FEATURE:
<221> NAME/KEY: CDS
<222> LOCATION: (1)...(1473)

<400> SEQUENCE: 23

| | | | | | | | | | | | | | | | | |
|---|---|---|---|---|---|---|---|---|---|---|---|---|---|---|---|---|
| atg | gcg | ggg | ccc | gag | cgc | tgg | ggc | ccc | ctg | ctc | ctg | tgc | ctg | ctg | cag | 48 |
| Met | Ala | Gly | Pro | Glu | Arg | Trp | Gly | Pro | Leu | Leu | Leu | Cys | Leu | Leu | Gln | |
| 1 | | | | 5 | | | | | 10 | | | | | 15 | | |
| gcc | gct | cca | ggg | agg | ccc | cgt | ctg | gcc | cct | ccc | cag | aat | gtg | acg | ctg | 96 |
| Ala | Ala | Pro | Gly | Arg | Pro | Arg | Leu | Ala | Pro | Pro | Gln | Asn | Val | Thr | Leu | |
| | | | 20 | | | | | 25 | | | | | 30 | | | |
| ctc | tcc | cag | aac | ttc | agc | gtg | tac | ctg | aca | tgg | ctc | cca | ggg | ctt | ggc | 144 |
| Leu | Ser | Gln | Asn | Phe | Ser | Val | Tyr | Leu | Thr | Trp | Leu | Pro | Gly | Leu | Gly | |
| | | 35 | | | | | 40 | | | | | 45 | | | | |
| aac | ccc | cag | gat | gtg | acc | tat | ttt | gtg | gcc | tat | cag | agc | tct | ccc | acc | 192 |
| Asn | Pro | Gln | Asp | Val | Thr | Tyr | Phe | Val | Ala | Tyr | Gln | Ser | Ser | Pro | Thr | |
| | 50 | | | | | 55 | | | | | 60 | | | | | |
| cgt | aga | cgg | tgg | cgc | gaa | gtg | gaa | gag | tgt | gcg | gga | acc | aag | gag | ctg | 240 |
| Arg | Arg | Arg | Trp | Arg | Glu | Val | Glu | Glu | Cys | Ala | Gly | Thr | Lys | Glu | Leu | |
| 65 | | | | 70 | | | | | 75 | | | | | 80 | | |
| cta | tgt | tct | atg | atg | tgc | ctg | aag | aaa | cag | gac | ctg | tac | aac | aag | ttc | 288 |
| Leu | Cys | Ser | Met | Met | Cys | Leu | Lys | Lys | Gln | Asp | Leu | Tyr | Asn | Lys | Phe | |
| | | | | 85 | | | | | 90 | | | | | 95 | | |
| aag | gga | cgc | gtg | cgg | acg | gtt | tct | ccc | agc | tcc | aag | tcc | ccc | tgg | gtg | 336 |
| Lys | Gly | Arg | Val | Arg | Thr | Val | Ser | Pro | Ser | Ser | Lys | Ser | Pro | Trp | Val | |
| | | | 100 | | | | | 105 | | | | | 110 | | | |
| gag | tcc | gaa | tac | ctg | gat | tac | ctt | ttt | gaa | gtg | gag | ccg | gcc | cca | cct | 384 |
| Glu | Ser | Glu | Tyr | Leu | Asp | Tyr | Leu | Phe | Glu | Val | Glu | Pro | Ala | Pro | Pro | |
| | | 115 | | | | | 120 | | | | | 125 | | | | |
| gtc | ctg | gtg | ctc | acc | cag | acg | gag | gag | atc | ctg | agt | gcc | aat | gcc | acg | 432 |
| Val | Leu | Val | Leu | Thr | Gln | Thr | Glu | Glu | Ile | Leu | Ser | Ala | Asn | Ala | Thr | |
| | 130 | | | | | 135 | | | | | 140 | | | | | |
| tac | cag | ctg | ccc | ccc | tgc | atg | ccc | cca | ctg | ttt | ctg | aag | tat | gag | gtg | 480 |
| Tyr | Gln | Leu | Pro | Pro | Cys | Met | Pro | Pro | Leu | Phe | Leu | Lys | Tyr | Glu | Val | |
| 145 | | | | | 150 | | | | | 155 | | | | | 160 | |
| gca | ttt | tgg | ggg | ggg | ggg | gcc | gga | acc | aag | acc | cta | ttt | cca | gtc | act | 528 |
| Ala | Phe | Trp | Gly | Gly | Gly | Ala | Gly | Thr | Lys | Thr | Leu | Phe | Pro | Val | Thr | |
| | | | | 165 | | | | | 170 | | | | | 175 | | |
| ccc | cat | ggc | cag | cca | gtc | cag | atc | act | ctc | cag | cca | gct | gcc | agc | gaa | 576 |
| Pro | His | Gly | Gln | Pro | Val | Gln | Ile | Thr | Leu | Gln | Pro | Ala | Ala | Ser | Glu | |
| | | | | 180 | | | | | 185 | | | | | 190 | | |
| cac | cac | tgc | ctc | agt | gcc | aga | acc | atc | tac | acg | ttc | agt | gtc | ccg | aaa | 624 |
| His | His | Cys | Leu | Ser | Ala | Arg | Thr | Ile | Tyr | Thr | Phe | Ser | Val | Pro | Lys | |
| | | | 195 | | | | | 200 | | | | | 205 | | | |
| tac | agc | aag | ttc | tct | aag | ccc | acc | tgc | ttc | ttg | ctg | gag | gtc | cca | gaa | 672 |
| Tyr | Ser | Lys | Phe | Ser | Lys | Pro | Thr | Cys | Phe | Leu | Leu | Glu | Val | Pro | Glu | |
| | | 210 | | | | | 215 | | | | | 220 | | | | |
| gcc | aac | tgg | gct | ttc | ctg | gtg | ctg | cca | tcg | ctt | ctg | ata | ctg | ctg | tta | 720 |
| Ala | Asn | Trp | Ala | Phe | Leu | Val | Leu | Pro | Ser | Leu | Leu | Ile | Leu | Leu | Leu | |
| 225 | | | | | 230 | | | | | 235 | | | | | 240 | |
| gta | att | gcc | gca | ggg | ggt | gtg | atc | tgg | aag | acc | ctc | atg | ggg | aac | ccc | 768 |
| Val | Ile | Ala | Ala | Gly | Gly | Val | Ile | Trp | Lys | Thr | Leu | Met | Gly | Asn | Pro | |
| | | | | 245 | | | | | 250 | | | | | 255 | | |
| tgg | ttt | cag | cgg | gca | aag | atg | cca | cgg | gcc | ctg | gaa | ctg | acc | aga | ggg | 816 |
| Trp | Phe | Gln | Arg | Ala | Lys | Met | Pro | Arg | Ala | Leu | Glu | Leu | Thr | Arg | Gly | |
| | | | | 260 | | | | | 265 | | | | | 270 | | |
| gtc | agg | ccg | acg | cct | cga | gtc | agg | gcc | cca | gcc | acc | caa | cag | aca | aga | 864 |
| Val | Arg | Pro | Thr | Pro | Arg | Val | Arg | Ala | Pro | Ala | Thr | Gln | Gln | Thr | Arg | |

-continued

```
                275                    280                    285
tgg aag aag gac ctt gca gag gac gaa gag gag gat gag gag gac       912
Trp Lys Lys Asp Leu Ala Glu Asp Glu Glu Glu Asp Glu Glu Asp
    290                    295                    300 aca gaa gat ggc gtc agc ttc cag ccc tac att gaa cca cct tct ttc   960
Thr Glu Asp Gly Val Ser Phe Gln Pro Tyr Ile Glu Pro Pro Ser Phe
305                    310                    315                    320 ctg ggg caa gag cac cag gct cca ggg cac tcg gag gct ggt ggg gtg  1008
Leu Gly Gln Glu His Gln Ala Pro Gly His Ser Glu Ala Gly Gly Val
                325                    330                    335 gac tca ggg agg ccc agg gct cct ctg gtc cca agc gaa ggc tcc tct  1056
Asp Ser Gly Arg Pro Arg Ala Pro Leu Val Pro Ser Glu Gly Ser Ser
            340                    345                    350 gct tgg gat tct tca gac aga agc tgg gcc agc act gtg gac tcc tcc  1104
Ala Trp Asp Ser Ser Asp Arg Ser Trp Ala Ser Thr Val Asp Ser Ser
        355                    360                    365 tgg gac agg gct ggg tcc tct ggc tat ttg gct gag aag ggg cca ggc  1152
Trp Asp Arg Ala Gly Ser Ser Gly Tyr Leu Ala Glu Lys Gly Pro Gly
    370                    375                    380 caa ggg ccg ggt ggg gat ggg cac caa gaa tct ctc cca cca cct gaa  1200
Gln Gly Pro Gly Gly Asp Gly His Gln Glu Ser Leu Pro Pro Pro Glu
385                    390                    395                    400 ttc tcc aag gac tcg ggt ttc ctg gaa gag ctc cca gaa gat aac ctc  1248
Phe Ser Lys Asp Ser Gly Phe Leu Glu Glu Leu Pro Glu Asp Asn Leu
                405                    410                    415 tcc tcc tgg gcc acc tgg ggc acc tta cca ccg gag ccg aat ctg gtc  1296
Ser Ser Trp Ala Thr Trp Gly Thr Leu Pro Pro Glu Pro Asn Leu Val
            420                    425                    430 cct ggg gga ccc cca gtt tct ctt cag aca ctg acc ttc tgc tgg gaa  1344
Pro Gly Gly Pro Pro Val Ser Leu Gln Thr Leu Thr Phe Cys Trp Glu
        435                    440                    445 agc agc cct gag gag gaa gag gag gcg agg gaa tca gaa att gag gac  1392
Ser Ser Pro Glu Glu Glu Glu Glu Ala Arg Glu Ser Glu Ile Glu Asp
    450                    455                    460 agc gat gcg ggc agc tgg ggg gct gag agc acc cag agg acc gag gac  1440
Ser Asp Ala Gly Ser Trp Gly Ala Glu Ser Thr Gln Arg Thr Glu Asp
465                    470                    475                    480 agg ggc cgg aca ttg ggg cat tac atg gcc agg tga                   1476
Arg Gly Arg Thr Leu Gly His Tyr Met Ala Arg
                485                    490
```

<210> SEQ ID NO 24
<211> LENGTH: 491
<212> TYPE: PRT
<213> ORGANISM: Homo sapiens

<400> SEQUENCE: 24

```
Met Ala Gly Pro Glu Arg Trp Gly Pro Leu Leu Leu Cys Leu Leu Gln
 1               5                  10                  15

Ala Ala Pro Gly Arg Pro Arg Leu Ala Pro Pro Gln Asn Val Thr Leu
                20                  25                  30

Leu Ser Gln Asn Phe Ser Val Tyr Leu Thr Trp Leu Pro Gly Leu Gly
            35                  40                  45

Asn Pro Gln Asp Val Thr Tyr Phe Val Ala Tyr Gln Ser Ser Pro Thr
        50                  55                  60

Arg Arg Arg Trp Arg Glu Val Glu Glu Cys Ala Gly Thr Lys Glu Leu
65                  70                  75                  80

Leu Cys Ser Met Met Cys Leu Lys Lys Gln Asp Leu Tyr Asn Lys Phe
                85                  90                  95
```

```
Lys Gly Arg Val Arg Thr Val Ser Pro Ser Lys Ser Pro Trp Val
            100                 105                 110

Glu Ser Glu Tyr Leu Asp Tyr Leu Phe Glu Val Glu Ala Pro Pro
            115                 120                 125

Val Leu Val Leu Thr Gln Thr Glu Glu Ile Leu Ser Ala Asn Ala Thr
130                 135                 140

Tyr Gln Leu Pro Pro Cys Met Pro Pro Leu Phe Leu Lys Tyr Glu Val
145                 150                 155                 160

Ala Phe Trp Gly Gly Gly Ala Gly Thr Lys Thr Leu Phe Pro Val Thr
                165                 170                 175

Pro His Gly Gln Pro Val Gln Ile Thr Leu Gln Pro Ala Ala Ser Glu
                180                 185                 190

His His Cys Leu Ser Ala Arg Thr Ile Tyr Thr Phe Ser Val Pro Lys
                195                 200                 205

Tyr Ser Lys Phe Ser Lys Pro Thr Cys Phe Leu Leu Glu Val Pro Glu
210                 215                 220

Ala Asn Trp Ala Phe Leu Val Leu Pro Ser Leu Ile Leu Leu Leu
225                 230                 235                 240

Val Ile Ala Ala Gly Gly Val Ile Trp Lys Thr Leu Met Gly Asn Pro
                245                 250                 255

Trp Phe Gln Arg Ala Lys Met Pro Arg Ala Leu Glu Leu Thr Arg Gly
                260                 265                 270

Val Arg Pro Thr Pro Arg Val Arg Ala Pro Ala Thr Gln Gln Thr Arg
                275                 280                 285

Trp Lys Lys Asp Leu Ala Glu Asp Glu Glu Glu Asp Glu Asp
                290                 295                 300

Thr Glu Asp Gly Val Ser Phe Gln Pro Tyr Ile Glu Pro Pro Ser Phe
305                 310                 315                 320

Leu Gly Gln Glu His Gln Ala Pro Gly His Ser Glu Ala Gly Gly Val
                325                 330                 335

Asp Ser Gly Arg Pro Arg Ala Pro Leu Val Pro Ser Glu Gly Ser Ser
                340                 345                 350

Ala Trp Asp Ser Ser Asp Arg Ser Trp Ala Ser Thr Val Asp Ser Ser
                355                 360                 365

Trp Asp Arg Ala Gly Ser Ser Gly Tyr Leu Ala Glu Lys Gly Pro Gly
                370                 375                 380

Gln Gly Pro Gly Gly Asp Gly His Gln Glu Ser Leu Pro Pro Pro Glu
385                 390                 395                 400

Phe Ser Lys Asp Ser Gly Phe Leu Glu Glu Leu Pro Glu Asp Asn Leu
                405                 410                 415

Ser Ser Trp Ala Thr Trp Gly Thr Leu Pro Pro Glu Pro Asn Leu Val
                420                 425                 430

Pro Gly Gly Pro Pro Val Ser Leu Gln Thr Leu Thr Phe Cys Trp Glu
                435                 440                 445

Ser Ser Pro Glu Glu Glu Glu Ala Arg Glu Ser Glu Ile Glu Asp
                450                 455                 460

Ser Asp Ala Gly Ser Trp Gly Ala Glu Ser Thr Gln Arg Thr Glu Asp
465                 470                 475                 480

Arg Gly Arg Thr Leu Gly His Tyr Met Ala Arg
                485                 490

<210> SEQ ID NO 25
<211> LENGTH: 611
<212> TYPE: DNA
<213> ORGANISM: Homo sapiens
```

<400> SEQUENCE: 25

```
catgggcta taggagcctc ccactttcac cagagcagcc tcactgtgcc ctgattcaca      60
tactgtggct ttccacgtga ggttttgttt agagggatcc actactcaag aaaaagttag     120
caaatcactc cttttgttgc aaaggagctg aggtcaaggg tggcaaaggc acttgtccaa     180
ggtcgcccag cagtgctgct ctgatgactt gtgcacatcc ccaagggtaa gagcttcgat     240
ctctgcacag ccgggccaac ctctgacccc ttgtccatgt cagtaaaata tgaaggtcac     300
agccaggatt tctaagggtc aggaggcctt caccgctgct ggggcacaca cacacatgca     360
tacacacata cgacacacac ctgtgtctcc ccaggggttt tccctgcagt gaggcttgtc     420
cagatgattg agcccaggag aggaagaaca aacaaactac ggagctgggg agggctgtgg     480
cttggggcca gctcccaggg aaattcccag acctgtaccg atgttctctc tggcaccagc     540
cgagctgctt cgtggaggta acttcaaaaa agtaaaagct atcatcagca tcaaaaaaaa     600
aaaaaaaggg c                                                         611
```

```
<210> SEQ ID NO 26
<211> LENGTH: 1563
<212> TYPE: DNA
<213> ORGANISM: Homo sapiens
<220> FEATURE:
<221> NAME/KEY: CDS
<222> LOCATION: (1)...(1563)
```

<400> SEQUENCE: 26

```
atg gcg ggg ccc gag cgc tgg ggc ccc ctg ctc ctg tgc ctg ctg cag        48
Met Ala Gly Pro Glu Arg Trp Gly Pro Leu Leu Leu Cys Leu Leu Gln
  1               5                  10                  15 gcc gct cca ggg agg ccc cgt ctg gcc cct ccc cag aat gtg acg ctg        96
Ala Ala Pro Gly Arg Pro Arg Leu Ala Pro Pro Gln Asn Val Thr Leu
             20                  25                  30 ctc tcc cag aac ttc agc gtg tac ctg aca tgg ctc cca ggg ctt ggc       144
Leu Ser Gln Asn Phe Ser Val Tyr Leu Thr Trp Leu Pro Gly Leu Gly
         35                  40                  45 aac ccc cag gat gtg acc tat ttt gtg gcc tat cag agc tct ccc acc       192
Asn Pro Gln Asp Val Thr Tyr Phe Val Ala Tyr Gln Ser Ser Pro Thr
     50                  55                  60 cgt aga cgg tgg cgc gaa gtg gaa gag tgt gcg gga acc aag gag ctg       240
Arg Arg Arg Trp Arg Glu Val Glu Glu Cys Ala Gly Thr Lys Glu Leu
 65                  70                  75                  80 cta tgt tct atg atg tgc ctg aag aaa cag gac ctg tac aac aag ttc       288
Leu Cys Ser Met Met Cys Leu Lys Lys Gln Asp Leu Tyr Asn Lys Phe
                 85                  90                  95 aag gga cgc gtg cgg acg gtt tct ccc agc tcc aag tcc ccc tgg gtg       336
Lys Gly Arg Val Arg Thr Val Ser Pro Ser Ser Lys Ser Pro Trp Val
            100                 105                 110 gag tcc gaa tac ctg gat tac ctt ttt gaa gtg gag ccg gcc cca cct       384
Glu Ser Glu Tyr Leu Asp Tyr Leu Phe Glu Val Glu Pro Ala Pro Pro
        115                 120                 125 gtc ctg gtg ctc acc cag acg gag gag atc ctg agt gcc aat gcc acg       432
Val Leu Val Leu Thr Gln Thr Glu Glu Ile Leu Ser Ala Asn Ala Thr
    130                 135                 140 tac cag ctg ccc ccc tgc atg ccc cca ctg gat ctg aag tat gag gtg       480
Tyr Gln Leu Pro Pro Cys Met Pro Pro Leu Asp Leu Lys Tyr Glu Val
145                 150                 155                 160 gca ttc tgg aag gag ggg gcc gga aac aag acc cta ttt cca gtc act       528
Ala Phe Trp Lys Glu Gly Ala Gly Asn Lys Thr Leu Phe Pro Val Thr
                165                 170                 175
```

-continued

| | |
|---|---|
| ccc cat ggc cag cca gtc cag atc act ctc cag cca gct gcc agc gaa<br>Pro His Gly Gln Pro Val Gln Ile Thr Leu Gln Pro Ala Ala Ser Glu<br>180 185 190 | 576 |
| cac cac tgc ctc agt gcc aga acc atc tac acg ttc agt gtc ccg aaa<br>His His Cys Leu Ser Ala Arg Thr Ile Tyr Thr Phe Ser Val Pro Lys<br>195 200 205 | 624 |
| tac agc aag ttc tct aag ccc acc tgc ttc ttg ctg gag gtc cca gaa<br>Tyr Ser Lys Phe Ser Lys Pro Thr Cys Phe Leu Leu Glu Val Pro Glu<br>210 215 220 | 672 |
| gcc aac tgg gct ttc ctg gtg ctg cca tcg ctt ctg ata ctg ctg tta<br>Ala Asn Trp Ala Phe Leu Val Leu Pro Ser Leu Leu Ile Leu Leu Leu<br>225 230 235 240 | 720 |
| gta att gcc gca ggg ggt gtg atc tgg aag acc ctc atg ggg aac ccc<br>Val Ile Ala Ala Gly Gly Val Ile Trp Lys Thr Leu Met Gly Asn Pro<br>245 250 255 | 768 |
| tgg ttt cag cgg gca aag atg cca cgg gcc ctg gac ttt tct gga cac<br>Trp Phe Gln Arg Ala Lys Met Pro Arg Ala Leu Asp Phe Ser Gly His<br>260 265 270 | 816 |
| aca cac cct gtg gca acc ttt cag ccc agc aga cca gag tcc gtg aat<br>Thr His Pro Val Ala Thr Phe Gln Pro Ser Arg Pro Glu Ser Val Asn<br>275 280 285 | 864 |
| gac ttg ttc ctc tgt ccc caa aag gaa ctg acc aga ggg gtc agg ccg<br>Asp Leu Phe Leu Cys Pro Gln Lys Glu Leu Thr Arg Gly Val Arg Pro<br>290 295 300 | 912 |
| acg cct cga gtc agg gcc cca gcc acc caa cag aca aga tgg aag aag<br>Thr Pro Arg Val Arg Ala Pro Ala Thr Gln Gln Thr Arg Trp Lys Lys<br>305 310 315 320 | 960 |
| gac ctt gca gag gac gaa gag gag gag gat gag gag gac aca gaa gat<br>Asp Leu Ala Glu Asp Glu Glu Glu Glu Asp Glu Glu Asp Thr Glu Asp<br>325 330 335 | 1008 |
| ggc gtc agc ttc cag ccc tac att gaa cca cct tct ttc ctg ggg caa<br>Gly Val Ser Phe Gln Pro Tyr Ile Glu Pro Pro Ser Phe Leu Gly Gln<br>340 345 350 | 1056 |
| gag cac cag gct cca ggg cac tcg gag gct ggt ggg gtg gac tca ggg<br>Glu His Gln Ala Pro Gly His Ser Glu Ala Gly Gly Val Asp Ser Gly<br>355 360 365 | 1104 |
| agg ccc agg gct cct ctg gtc cca agc gaa ggc tcc tct gct tgg gat<br>Arg Pro Arg Ala Pro Leu Val Pro Ser Glu Gly Ser Ser Ala Trp Asp<br>370 375 380 | 1152 |
| tct tca gac aga agc tgg gcc agc act gtg gac tcc tcc tgg gac agg<br>Ser Ser Asp Arg Ser Trp Ala Ser Thr Val Asp Ser Ser Trp Asp Arg<br>385 390 395 400 | 1200 |
| gct ggg tcc tct ggc tat ttg gct gag aag ggg cca ggc caa ggg ccg<br>Ala Gly Ser Ser Gly Tyr Leu Ala Glu Lys Gly Pro Gly Gln Gly Pro<br>405 410 415 | 1248 |
| ggt ggg gat ggg cac caa gaa tct ctc cca cca cct gaa ttc tcc aag<br>Gly Gly Asp Gly His Gln Glu Ser Leu Pro Pro Pro Glu Phe Ser Lys<br>420 425 430 | 1296 |
| gac tcg ggt ttc ctg gaa gag ctc cca gaa gat aac ctc tcc tcc tgg<br>Asp Ser Gly Phe Leu Glu Glu Leu Pro Glu Asp Asn Leu Ser Ser Trp<br>435 440 445 | 1344 |
| gcc acc tgg ggc acc tta cca ccg gag ccg aat ctg gtc cct ggg gga<br>Ala Thr Trp Gly Thr Leu Pro Pro Glu Pro Asn Leu Val Pro Gly Gly<br>450 455 460 | 1392 |
| ccc cca gtt tct ctt cag aca ctg acc ttc tgc tgg gaa agc agc cct<br>Pro Pro Val Ser Leu Gln Thr Leu Thr Phe Cys Trp Glu Ser Ser Pro<br>465 470 475 480 | 1440 |
| gag gag gaa gag gag gcg agg gaa tca gaa att gag gac agc gat gcg<br>Glu Glu Glu Glu Glu Ala Arg Glu Ser Glu Ile Glu Asp Ser Asp Ala<br>485 490 495 | 1488 |

-continued

```
ggc agc tgg ggg gct gag agc acc cag agg acc gag gac agg ggc cgg    1536
Gly Ser Trp Gly Ala Glu Ser Thr Gln Arg Thr Glu Asp Arg Gly Arg
        500                 505                 510 aca ttg ggg cat tac atg gcc agg tga                                1563
Thr Leu Gly His Tyr Met Ala Arg *
        515                 520

<210> SEQ ID NO 27
<211> LENGTH: 520
<212> TYPE: PRT
<213> ORGANISM: Homo sapiens

<400> SEQUENCE: 27

Met Ala Gly Pro Glu Arg Trp Gly Pro Leu Leu Cys Leu Leu Gln
  1               5                  10                  15

Ala Ala Pro Gly Arg Pro Arg Leu Ala Pro Pro Gln Asn Val Thr Leu
                 20                  25                  30

Leu Ser Gln Asn Phe Ser Val Tyr Leu Thr Trp Leu Pro Gly Leu Gly
                 35                  40                  45

Asn Pro Gln Asp Val Thr Tyr Phe Val Ala Tyr Gln Ser Ser Pro Thr
         50                  55                  60

Arg Arg Arg Trp Arg Glu Val Glu Glu Cys Ala Gly Thr Lys Glu Leu
 65                  70                  75                  80

Leu Cys Ser Met Met Cys Leu Lys Lys Gln Asp Leu Tyr Asn Lys Phe
                     85                  90                  95

Lys Gly Arg Val Arg Thr Val Ser Pro Ser Ser Lys Ser Pro Trp Val
                100                 105                 110

Glu Ser Glu Tyr Leu Asp Tyr Leu Phe Glu Val Glu Pro Ala Pro Pro
                115                 120                 125

Val Leu Val Leu Thr Gln Thr Glu Glu Ile Leu Ser Ala Asn Ala Thr
        130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Thr Leu Phe Pro Val Thr
                165                 170                 175

Pro His Gly Gln Pro Val Gln Ile Thr Leu Gln Pro Ala Ala Ser Glu
                180                 185                 190

His His Cys Leu Ser Ala Arg Thr Ile Tyr Thr Phe Ser Val Pro Lys
                195                 200                 205

Tyr Ser Lys Phe Ser Lys Pro Thr Cys Phe Leu Leu Glu Val Pro Glu
        210                 215                 220

Ala Asn Trp Ala Phe Leu Val Leu Pro Ser Leu Leu Ile Leu Leu Leu
225                 230                 235                 240

Val Ile Ala Ala Gly Gly Val Ile Trp Lys Thr Leu Met Gly Asn Pro
                245                 250                 255

Trp Phe Gln Arg Ala Lys Met Pro Arg Ala Leu Asp Phe Ser Gly His
                260                 265                 270

Thr His Pro Val Ala Thr Phe Gln Pro Ser Arg Pro Glu Ser Val Asn
                275                 280                 285

Asp Leu Phe Leu Cys Pro Gln Lys Glu Leu Thr Arg Gly Val Arg Pro
        290                 295                 300

Thr Pro Arg Val Arg Ala Pro Ala Thr Gln Gln Thr Arg Trp Lys Lys
305                 310                 315                 320

Asp Leu Ala Glu Asp Glu Glu Glu Asp Glu Glu Asp Thr Glu Asp
                325                 330                 335

Gly Val Ser Phe Gln Pro Tyr Ile Glu Pro Pro Ser Phe Leu Gly Gln
```

```
                340               345                350
Glu His Gln Ala Pro Gly His Ser Glu Ala Gly Gly Val Asp Ser Gly
            355                 360                 365

Arg Pro Arg Ala Pro Leu Val Pro Ser Glu Gly Ser Ser Ala Trp Asp
370                 375                 380

Ser Ser Asp Arg Ser Trp Ala Ser Thr Val Asp Ser Ser Trp Asp Arg
385                 390                 395                 400

Ala Gly Ser Ser Gly Tyr Leu Ala Glu Lys Gly Pro Gly Gln Gly Pro
                405                 410                 415

Gly Gly Asp Gly His Gln Glu Ser Leu Pro Pro Glu Phe Ser Lys
            420                 425                 430

Asp Ser Gly Phe Leu Glu Glu Leu Pro Glu Asp Asn Leu Ser Ser Trp
                435                 440                 445

Ala Thr Trp Gly Thr Leu Pro Pro Glu Pro Asn Leu Val Pro Gly Gly
            450                 455                 460

Pro Pro Val Ser Leu Gln Thr Leu Thr Phe Cys Trp Glu Ser Ser Pro
465                 470                 475                 480

Glu Glu Glu Glu Glu Ala Arg Glu Ser Glu Ile Glu Asp Ser Asp Ala
                485                 490                 495

Gly Ser Trp Gly Ala Glu Ser Thr Gln Arg Thr Glu Asp Arg Gly Arg
            500                 505                 510

Thr Leu Gly His Tyr Met Ala Arg
            515                 520

<210> SEQ ID NO 28
<211> LENGTH: 674
<212> TYPE: DNA
<213> ORGANISM: Homo sapiens
<220> FEATURE:
<221> NAME/KEY: CDS
<222> LOCATION: (1)...(633)

<400> SEQUENCE: 28 atg gcg ggg ccc gag cgc tgg ggc ccc ctg ctc ctg tgc ctg ctg cag      48
Met Ala Gly Pro Glu Arg Trp Gly Pro Leu Leu Leu Cys Leu Leu Gln
1               5                   10                  15 gcc gct cca ggg agg ccc cgt ctg gcc cct ccc cag aat gtg acg ctg      96
Ala Ala Pro Gly Arg Pro Arg Leu Ala Pro Pro Gln Asn Val Thr Leu
            20                  25                  30 ctc tcc cag aac ttc agc gtg tac ctg aca tgg ctc cca ggg ctt ggc     144
Leu Ser Gln Asn Phe Ser Val Tyr Leu Thr Trp Leu Pro Gly Leu Gly
        35                  40                  45 aac ccc cag gat gtg acc tat ttt gtg gcc tat cag agc tct ccc acc     192
Asn Pro Gln Asp Val Thr Tyr Phe Val Ala Tyr Gln Ser Ser Pro Thr
    50                  55                  60 cgt aga cgg tgg cgc gaa gtg gaa gag tgt gcg gga acc aag gag ctg     240
Arg Arg Arg Trp Arg Glu Val Glu Glu Cys Ala Gly Thr Lys Glu Leu
65                  70                  75                  80 cta tgt tct atg atg tgc ctg aag aaa cag gac ctg tac aac aag ttc     288
Leu Cys Ser Met Met Cys Leu Lys Lys Gln Asp Leu Tyr Asn Lys Phe
                85                  90                  95 aag gga cgc gtg cgg acg gtt tct ccc agc tcc aag tcc ccc tgg gtg     336
Lys Gly Arg Val Arg Thr Val Ser Pro Ser Ser Lys Ser Pro Trp Val
            100                 105                 110 gag tcc gaa tac ctg gat tac ctt ttt gaa gtg gag ccg gcc cca cct     384
Glu Ser Glu Tyr Leu Asp Tyr Leu Phe Glu Val Glu Pro Ala Pro Pro
        115                 120                 125 gtc ctg gtg ctc acc cag acg gag gag atc ctg agt gcc aat gcc acg     432
Val Leu Val Leu Thr Gln Thr Glu Glu Ile Leu Ser Ala Asn Ala Thr
```

```
              130                 135                 140
tac cag ctg ccc ccc tgc atg ccc cca ctg gat ctg aag tat gag gtg          480
Tyr Gln Leu Pro Pro Cys Met Pro Pro Leu Asp Leu Lys Tyr Glu Val
145                 150                 155                 160 gca ttc tgg aag gag ggg gcc gga aac aag gtg gga agc tcc ttt cct          528
Ala Phe Trp Lys Glu Gly Ala Gly Asn Lys Val Gly Ser Ser Phe Pro
                165                 170                 175 gcc ccc agg cta ggc ccg ctc ctc cac ccc tta ctc agg ttc ttc              576
Ala Pro Arg Leu Gly Pro Leu Leu His Pro Phe Leu Leu Arg Phe Phe
            180                 185                 190 tca ccc tcc cag cct gct cct gca ccc ctc ctc cag gaa gtc ttc cct          624
Ser Pro Ser Gln Pro Ala Pro Ala Pro Leu Leu Gln Glu Val Phe Pro
        195                 200                 205 gta cac tcc tgacttctgg cagtcagccc taataaaatc tgatcaaagt                  673
Val His Ser
    210 a                                                                        674

<210> SEQ ID NO 29
<211> LENGTH: 211
<212> TYPE: PRT
<213> ORGANISM: Homo sapiens

<400> SEQUENCE: 29

Met Ala Gly Pro Glu Arg Trp Gly Pro Leu Leu Leu Cys Leu Leu Gln
  1               5                  10                  15

Ala Ala Pro Gly Arg Pro Arg Leu Ala Pro Pro Gln Asn Val Thr Leu
                 20                  25                  30

Leu Ser Gln Asn Phe Ser Val Tyr Leu Thr Trp Leu Pro Gly Leu Gly
             35                  40                  45

Asn Pro Gln Asp Val Thr Tyr Phe Val Ala Tyr Gln Ser Ser Pro Thr
         50                  55                  60

Arg Arg Arg Trp Arg Glu Val Glu Glu Cys Ala Gly Thr Lys Glu Leu
 65                  70                  75                  80

Leu Cys Ser Met Met Cys Leu Lys Lys Gln Asp Leu Tyr Asn Lys Phe
                 85                  90                  95

Lys Gly Arg Val Arg Thr Val Ser Pro Ser Ser Lys Ser Pro Trp Val
                100                 105                 110

Glu Ser Glu Tyr Leu Asp Tyr Leu Phe Glu Val Glu Pro Ala Pro Pro
            115                 120                 125

Val Leu Val Leu Thr Gln Thr Glu Glu Ile Leu Ser Ala Asn Ala Thr
        130                 135                 140

Tyr Gln Leu Pro Pro Cys Met Pro Pro Leu Asp Leu Lys Tyr Glu Val
145                 150                 155                 160

Ala Phe Trp Lys Glu Gly Ala Gly Asn Lys Val Gly Ser Ser Phe Pro
                165                 170                 175

Ala Pro Arg Leu Gly Pro Leu Leu His Pro Phe Leu Leu Arg Phe Phe
            180                 185                 190

Ser Pro Ser Gln Pro Ala Pro Ala Pro Leu Leu Gln Glu Val Phe Pro
        195                 200                 205

Val His Ser
    210

<210> SEQ ID NO 30
<211> LENGTH: 23
<212> TYPE: DNA
<213> ORGANISM: Artificial Sequence
<220> FEATURE:
```

<223> OTHER INFORMATION: oligonucleotide primer ZC40134

<400> SEQUENCE: 30
cagttcctgt cgccaggctc cac                                                 23

<210> SEQ ID NO 31
<211> LENGTH: 32
<212> TYPE: DNA
<213> ORGANISM: Artificial Sequence
<220> FEATURE:
<223> OTHER INFORMATION: oligonucleotide primer ZC40214

<400> SEQUENCE: 31
ggcggcggcc gctcagacac acaggtcccc ac                                       32

<210> SEQ ID NO 32
<211> LENGTH: 30
<212> TYPE: DNA
<213> ORGANISM: Artificial Sequence
<220> FEATURE:
<223> OTHER INFORMATION: oligonucleotide primer ZC40209

<400> SEQUENCE: 32
ggcgaagctt atggctgcag cttggaccgt                                          30

<210> SEQ ID NO 33
<211> LENGTH: 32
<212> TYPE: DNA
<213> ORGANISM: Artificial Sequence
<220> FEATURE:
<223> OTHER INFORMATION: oligonucleotide primer ZC40213

<400> SEQUENCE: 33
ggcggcggcc gctcaggtgg actcagggtg gg                                       32

<210> SEQ ID NO 34
<211> LENGTH: 23
<212> TYPE: DNA
<213> ORGANISM: Artificial Sequence
<220> FEATURE:
<223> OTHER INFORMATION: oligonucleotide primer ZC39295

<400> SEQUENCE: 34
cagacatgac cggggactgc atg                                                 23

<210> SEQ ID NO 35
<211> LENGTH: 22
<212> TYPE: DNA
<213> ORGANISM: Artificial Sequence
<220> FEATURE:
<223> OTHER INFORMATION: oligonucleotide primer ZC39298

<400> SEQUENCE: 35
tcagacacac aggtccccgc tg                                                  22

<210> SEQ ID NO 36
<211> LENGTH: 18
<212> TYPE: DNA
<213> ORGANISM: Artificial Sequence
<220> FEATURE:
<223> OTHER INFORMATION: oligonucleotide primer ZC40632

<400> SEQUENCE: 36
tggggactgc acgccagt                                                       18

<210> SEQ ID NO 37

-continued

```
<211> LENGTH: 18
<212> TYPE: DNA
<213> ORGANISM: Artificial Sequence
<220> FEATURE:
<223> OTHER INFORMATION: oligonucleotide primer ZC40633

<400> SEQUENCE: 37
gctggtccaa gacgtcca                                                 18

<210> SEQ ID NO 38
<211> LENGTH: 18
<212> TYPE: DNA
<213> ORGANISM: Artificial Sequence
<220> FEATURE:
<223> OTHER INFORMATION: oligonucleotide primer ZC40638

<400> SEQUENCE: 38
cggggactgc atgccagt                                                 18

<210> SEQ ID NO 39
<211> LENGTH: 18
<212> TYPE: DNA
<213> ORGANISM: Artificial Sequence
<220> FEATURE:
<223> OTHER INFORMATION: oligonucleotide primer ZC40639

<400> SEQUENCE: 39
ggctggtcca agacatcc                                                 18

<210> SEQ ID NO 40
<211> LENGTH: 1013
<212> TYPE: DNA
<213> ORGANISM: Homo sapiens
<220> FEATURE:
<221> NAME/KEY: CDS
<222> LOCATION: (14)...(991)

<400> SEQUENCE: 40
ccagcgtccg tcc atg gcg tgg agc ctt ggg agc tgg ctg ggt ggc tgc       49
            Met Ala Trp Ser Leu Gly Ser Trp Leu Gly Gly Cys
              1               5                  10 ctg ctg gtg tca gca ttg gga atg gta cca cct ccc gaa aat gtc aga      97
Leu Leu Val Ser Ala Leu Gly Met Val Pro Pro Pro Glu Asn Val Arg
         15                  20                  25 atg aat tct gtt aat ttc aag aac att cta cag tgg gag tca cct gct     145
Met Asn Ser Val Asn Phe Lys Asn Ile Leu Gln Trp Glu Ser Pro Ala
 30                  35                  40 ttt gcc aaa ggg aac ctg act ttc aca gct cag tac cta agt tat agg     193
Phe Ala Lys Gly Asn Leu Thr Phe Thr Ala Gln Tyr Leu Ser Tyr Arg
     45                  50                  55                  60 ata ttc caa gat aaa tgc atg aat act acc ttg acg gaa tgt gat ttc     241
Ile Phe Gln Asp Lys Cys Met Asn Thr Thr Leu Thr Glu Cys Asp Phe
                 65                  70                  75 tca agt ctt tcc aag tat ggt gac cac acc ttg aga gtc agg gct gaa     289
Ser Ser Leu Ser Lys Tyr Gly Asp His Thr Leu Arg Val Arg Ala Glu
             80                  85                  90 ttt gca gat gag cat tca gac tgg gta aac atc acc ttc tgt cct gtg     337
Phe Ala Asp Glu His Ser Asp Trp Val Asn Ile Thr Phe Cys Pro Val
         95                 100                 105 gat gac acc att att gga ccc cct gga atg caa gta gaa gta ctt gct     385
Asp Asp Thr Ile Ile Gly Pro Pro Gly Met Gln Val Glu Val Leu Ala
    110                 115                 120 gat tct tta cat atg cgt ttc tta gcc cct aaa att gag aat gaa tac     433
Asp Ser Leu His Met Arg Phe Leu Ala Pro Lys Ile Glu Asn Glu Tyr
125                 130                 135                 140
```

```
gaa act tgg act atg aag aat gtg tat aac tca tgg act tat aat gtg      481
Glu Thr Trp Thr Met Lys Asn Val Tyr Asn Ser Trp Thr Tyr Asn Val
            145                 150                 155 caa tac tgg aaa aac ggt act gat gaa aag ttt caa att act ccc cag      529
Gln Tyr Trp Lys Asn Gly Thr Asp Glu Lys Phe Gln Ile Thr Pro Gln
            160                 165                 170 tat gac ttt gag gtc ctc aga aac ctg gag cca tgg aca act tat tgt      577
Tyr Asp Phe Glu Val Leu Arg Asn Leu Glu Pro Trp Thr Thr Tyr Cys
            175                 180                 185 gtt caa gtt cga ggg ttt ctt cct gat cgg aac aaa gct ggg gaa tgg      625
Val Gln Val Arg Gly Phe Leu Pro Asp Arg Asn Lys Ala Gly Glu Trp
            190                 195                 200 agt gag cct gtc tgt gag caa aca acc cat gac gaa acg gtc ccc tcc      673
Ser Glu Pro Val Cys Glu Gln Thr Thr His Asp Glu Thr Val Pro Ser
205                 210                 215                 220 tgg atg gtg gcc gtc atc ctc atg gcc tcg gtc ttc atg gtc tgc ctg      721
Trp Met Val Ala Val Ile Leu Met Ala Ser Val Phe Met Val Cys Leu
                    225                 230                 235 gca ctc ctc ggc tgc ttc tcc ttg ctg tgg tgc gtt tac aag aag aca      769
Ala Leu Leu Gly Cys Phe Ser Leu Leu Trp Cys Val Tyr Lys Lys Thr
                240                 245                 250 aag tac gcc ttc tcc cct agg aat tct ctt cca cag cac ctg aaa gag      817
Lys Tyr Ala Phe Ser Pro Arg Asn Ser Leu Pro Gln His Leu Lys Glu
            255                 260                 265 ttt ttg ggc cat cct cat cat aac aca ctt ctg ttt ttc tcc ttt cca      865
Phe Leu Gly His Pro His His Asn Thr Leu Leu Phe Phe Ser Phe Pro
            270                 275                 280 ttg tcg gat gag aat gat gtt ttt gac aag cta agt gtc att gca gaa      913
Leu Ser Asp Glu Asn Asp Val Phe Asp Lys Leu Ser Val Ile Ala Glu
285                 290                 295                 300 gac tct gag agc ggc aag cag aat cct ggt gac agc tgc agc ctc ggg      961
Asp Ser Glu Ser Gly Lys Gln Asn Pro Gly Asp Ser Cys Ser Leu Gly
                305                 310                 315 acc ccg cct ggg cag ggg ccc caa agc tag gctctgagaa ggaaacacac       1011
Thr Pro Pro Gly Gln Gly Pro Gln Ser *
                320                 325 tc                                                                  1013

<210> SEQ ID NO 41
<211> LENGTH: 325
<212> TYPE: PRT
<213> ORGANISM: Homo sapiens

<400> SEQUENCE: 41

Met Ala Trp Ser Leu Gly Ser Trp Leu Gly Gly Cys Leu Leu Val Ser
 1               5                  10                  15

Ala Leu Gly Met Val Pro Pro Glu Asn Val Arg Met Asn Ser Val
            20                  25                  30

Asn Phe Lys Asn Ile Leu Gln Trp Glu Ser Pro Ala Phe Ala Lys Gly
        35                  40                  45

Asn Leu Thr Phe Thr Ala Gln Tyr Leu Ser Tyr Arg Ile Phe Gln Asp
    50                  55                  60

Lys Cys Met Asn Thr Thr Leu Thr Glu Cys Asp Phe Ser Ser Leu Ser
65                  70                  75                  80

Lys Tyr Gly Asp His Thr Leu Arg Val Arg Ala Glu Phe Ala Asp Glu
                85                  90                  95

His Ser Asp Trp Val Asn Ile Thr Phe Cys Pro Val Asp Thr Ile
            100                 105                 110
```

Ile Gly Pro Pro Gly Met Gln Val Glu Val Leu Ala Asp Ser Leu His
115                 120                 125

Met Arg Phe Leu Ala Pro Lys Ile Glu Asn Glu Tyr Glu Thr Trp Thr
130                 135                 140

Met Lys Asn Val Tyr Asn Ser Trp Thr Tyr Asn Val Gln Tyr Trp Lys
145                 150                 155                 160

Asn Gly Thr Asp Glu Lys Phe Gln Ile Thr Pro Gln Tyr Asp Phe Glu
            165                 170                 175

Val Leu Arg Asn Leu Glu Pro Trp Thr Thr Tyr Cys Val Gln Val Arg
        180                 185                 190

Gly Phe Leu Pro Asp Arg Asn Lys Ala Gly Glu Trp Ser Glu Pro Val
    195                 200                 205

Cys Glu Gln Thr Thr His Asp Glu Thr Val Pro Ser Trp Met Val Ala
210                 215                 220

Val Ile Leu Met Ala Ser Val Phe Met Val Cys Leu Ala Leu Leu Gly
225                 230                 235                 240

Cys Phe Ser Leu Leu Trp Cys Val Tyr Lys Thr Lys Tyr Ala Phe
            245                 250                 255

Ser Pro Arg Asn Ser Leu Pro Gln His Leu Lys Glu Phe Leu Gly His
        260                 265                 270

Pro His His Asn Thr Leu Leu Phe Phe Ser Phe Pro Leu Ser Asp Glu
    275                 280                 285

Asn Asp Val Phe Asp Lys Leu Ser Val Ile Ala Glu Asp Ser Glu Ser
290                 295                 300

Gly Lys Gln Asn Pro Gly Asp Ser Cys Ser Leu Gly Thr Pro Pro Gly
305                 310                 315                 320

Gln Gly Pro Gln Ser
            325

<210> SEQ ID NO 42
<211> LENGTH: 8
<212> TYPE: PRT
<213> ORGANISM: Artificial Sequence
<220> FEATURE:
<223> OTHER INFORMATION: FLAG peptide tag

<400> SEQUENCE: 42

Asp Tyr Lys Asp Asp Asp Asp Lys
1               5

<210> SEQ ID NO 43
<211> LENGTH: 699
<212> TYPE: DNA
<213> ORGANISM: Homo sapiens

<400> SEQUENCE: 43
gagcccagat cttcagacaa aactcacaca tgcccaccgt gcccagcacc tgaagccgag      60
ggggcaccgt cagtcttcct cttccccca  aacccaagg  acaccctcat gatctcccgg     120 accctgagg  tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagcccctcc catcctccat cgagaaaacc    360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa  gaccacgcct     540

-continued

```
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaataa                           699

<210> SEQ ID NO 44
<211> LENGTH: 28
<212> TYPE: DNA
<213> ORGANISM: Artificial Sequence
<220> FEATURE:
<223> OTHER INFORMATION: oligonucleotide primer ZC37967

<400> SEQUENCE: 44
gcggatccag gccccgtctg gcccctcc                                        28

<210> SEQ ID NO 45
<211> LENGTH: 30
<212> TYPE: DNA
<213> ORGANISM: Artificial Sequence
<220> FEATURE:
<223> OTHER INFORMATION: oligonucleotide primer ZC37972

<400> SEQUENCE: 45
gcagatctcc agttggcttc tgggacctcc                                      30

<210> SEQ ID NO 46
<211> LENGTH: 615
<212> TYPE: DNA
<213> ORGANISM: Homo sapiens
<220> FEATURE:
<221> NAME/KEY: misc_feature
<222> LOCATION: (1)...(615)
<223> OTHER INFORMATION: n = A, T, C or G

<400> SEQUENCE: 46
atgacnggng aytgyatgcc ngtnytngtn ytnatggcng cngtnytnac ngtnacnggn     60
gcngtnccng tngcnmgnyt nmgnggngcn ytnccngayg cnmgnggntg ycayathgcn    120
carttyaarw snytnwsncc ncargarytn cargcnttya armgngcnaa rgaygcnytn    180
gargarwsny tnytnytnaa rgaytgyaar tgymgnwsnm gnytnttycc nmgnacntgg    240
gayytnmgnc arytncargt nmgngarmgn ccngtngcny tngargcnga rytngcnytn    300
acnytnaarg tnytngargc nacngcngay acngayccng cnytnggnga ygtnytngay    360
carccnytnc ayacnytnca ycayathytn wsncarytnm gngcntgygt nwsnmgncar    420
ggnccnggna cncarathca rccncarccn acngcnggnc cnmgnacnmg nggnmgnytn    480
caycaytggy tncaymgnyt ncargargcn ccnaaraarg arwsnccngg ntgyytngar    540
gcnwsngtna cnttyaayyt nttymgnytn ytnacnmgng ayytnaaytg ygtngcnwsn    600
ggngayytnt gygtn                                                     615

<210> SEQ ID NO 47
<211> LENGTH: 23
<212> TYPE: DNA
<213> ORGANISM: Artificial Sequence
<220> FEATURE:
<223> OTHER INFORMATION: oligonucleotide primer ZC39339

<400> SEQUENCE: 47
cagacatgac tggggactgc acg                                             23

<210> SEQ ID NO 48
<211> LENGTH: 22
```

```
<212> TYPE: DNA
<213> ORGANISM: Artificial Sequence
<220> FEATURE:
<223> OTHER INFORMATION: oligonucleotide primer ZC39393

<400> SEQUENCE: 48
tcagacacac aggtccccac tg                                            22

<210> SEQ ID NO 49
<211> LENGTH: 22
<212> TYPE: DNA
<213> ORGANISM: Artificial Sequence
<220> FEATURE:
<223> OTHER INFORMATION: oligonucleotide primer ZC39340

<400> SEQUENCE: 49
tgggtgacag cctcagagtg tt                                            22

<210> SEQ ID NO 50
<211> LENGTH: 22
<212> TYPE: DNA
<213> ORGANISM: Artificial Sequence
<220> FEATURE:
<223> OTHER INFORMATION: oligonucleotide primer ZC39341

<400> SEQUENCE: 50
atagcgactg ggtggcaata aa                                            22

<210> SEQ ID NO 51
<211> LENGTH: 23
<212> TYPE: DNA
<213> ORGANISM: Artificial Sequence
<220> FEATURE:
<223> OTHER INFORMATION: oligonucleotide primer ZC39295

<400> SEQUENCE: 51
cagacatgac cggggactgc atg                                           23

<210> SEQ ID NO 52
<211> LENGTH: 22
<212> TYPE: DNA
<213> ORGANISM: Artificial Sequence
<220> FEATURE:
<223> OTHER INFORMATION: oligonucleotide primer ZC39298

<400> SEQUENCE: 52
tcagacacac aggtccccgc tg                                            22

<210> SEQ ID NO 53
<211> LENGTH: 22
<212> TYPE: DNA
<213> ORGANISM: Artificial Sequence
<220> FEATURE:
<223> OTHER INFORMATION: oligonucleotide primer ZC39687

<400> SEQUENCE: 53
atgctcctcc tgctgttgcc tc                                            22

<210> SEQ ID NO 54
<211> LENGTH: 22
<212> TYPE: DNA
<213> ORGANISM: Artificial Sequence
<220> FEATURE:
<223> OTHER INFORMATION: oligonucleotide primer ZC39741

<400> SEQUENCE: 54
tgcttcaggt ccctggccct gg                                            22
```

```
<210> SEQ ID NO 55
<211> LENGTH: 22
<212> TYPE: DNA
<213> ORGANISM: Artificial Sequence
<220> FEATURE:
<223> OTHER INFORMATION: oligonucleotide primer ZC39732

<400> SEQUENCE: 55
tcacagaccc cggagagcaa ca                                              22

<210> SEQ ID NO 56
<211> LENGTH: 23
<212> TYPE: DNA
<213> ORGANISM: Artificial Sequence
<220> FEATURE:
<223> OTHER INFORMATION: oligonucleotide primer ZC39701

<400> SEQUENCE: 56
aggtcagaca cactggtctc cat                                             23

<210> SEQ ID NO 57
<211> LENGTH: 22
<212> TYPE: DNA
<213> ORGANISM: Artificial Sequence
<220> FEATURE:
<223> OTHER INFORMATION: oligonucleotide primer ZC39688

<400> SEQUENCE: 57
ggtcagacac actggtctcc ac                                              22

<210> SEQ ID NO 58
<211> LENGTH: 24
<212> TYPE: DNA
<213> ORGANISM: Artificial Sequence
<220> FEATURE:
<223> OTHER INFORMATION: oligonucleotide primer ZC40288

<400> SEQUENCE: 58
gaaggagggg gccggaaaca agac                                            24

<210> SEQ ID NO 59
<211> LENGTH: 24
<212> TYPE: DNA
<213> ORGANISM: Artificial Sequence
<220> FEATURE:
<223> OTHER INFORMATION: oligonucleotide primer ZC40291

<400> SEQUENCE: 59
cagattcggc tccggtggta aggt                                            24
```